US011505551B2

(12) United States Patent
Chen et al.

(10) Patent No.: US 11,505,551 B2
(45) Date of Patent: Nov. 22, 2022

(54) METHODS FOR PREPARING SUBSTITUTED PYRIDINONE-CONTAINING TRICYCLIC COMPOUNDS

(71) Applicant: Arbutus Biopharma Corporation, Burnaby (CA)

(72) Inventors: Shuai Chen, Warrington, PA (US); Bruce D. Dorsey, Ambler, PA (US); Dimitar B. Gotchev, Hatboro, PA (US); Duyan Nguyen, Ambler, PA (US); Mahesh Kumar Pallerla, Chalfont, PA (US); Ganapati Reddy Pamulapati, Warrington, PA (US)

(73) Assignee: Arbutus Biopharma Corporation, Burnaby (CA)

( * ) Notice: Subject to any disclaimer, the term of this patent is extended or adjusted under 35 U.S.C. 154(b) by 133 days.

(21) Appl. No.: 17/046,139

(22) PCT Filed: Apr. 11, 2019

(86) PCT No.: PCT/US2019/027004
§ 371 (c)(1),
(2) Date: Oct. 8, 2020

(87) PCT Pub. No.: WO2019/200109
PCT Pub. Date: Oct. 17, 2019

(65) Prior Publication Data
US 2021/0032246 A1  Feb. 4, 2021

Related U.S. Application Data

(60) Provisional application No. 62/700,048, filed on Jul. 18, 2018, provisional application No. 62/656,605, filed on Apr. 12, 2018.

(51) Int. Cl.
C07D 471/14  (2006.01)
C07B 49/00  (2006.01)
C07B 51/00  (2006.01)

(52) U.S. Cl.
CPC ............ C07D 471/14 (2013.01); C07B 49/00 (2013.01); C07B 51/00 (2013.01)

(58) Field of Classification Search
CPC .......................... C07D 471/14; C07D 471/16
USPC ..................................... 546/88, 81
See application file for complete search history.

(56) References Cited

U.S. PATENT DOCUMENTS

| 6,514,912 | B1 | 2/2003 | Guarna et al. |
| 7,307,073 | B2 | 12/2007 | Grove et al. |
| 8,063,037 | B2 | 11/2011 | Rewinkel et al. |
| 9,458,153 | B2 | 10/2016 | Han et al. |
| 2015/0210682 | A1 | 7/2015 | Wang et al. |
| 2016/0122344 | A1 | 5/2016 | Han et al. |
| 2016/0296515 | A1 | 10/2016 | Han et al. |
| 2017/0057952 | A1 | 3/2017 | Yang et al. |
| 2019/0314347 | A1 | 10/2019 | Bailey et al. |
| 2019/0381014 | A1 | 12/2019 | Chen et al. |
| 2020/0261432 | A1 | 8/2020 | Bailey et al. |

FOREIGN PATENT DOCUMENTS

| EP | 0093498 A2 | 11/1983 |
| JP | 60-197684 A | 10/1985 |
| JP | H04-77 B2 | 1/1992 |
| TW | 201811788 A | 4/2018 |
| WO | 2015113990 A1 | 8/2015 |
| WO | 2015173164 A1 | 11/2015 |
| WO | 2016054421 A1 | 4/2016 |
| WO | 2016071215 A1 | 5/2016 |
| WO | 2017013046 A1 | 1/2017 |
| WO | 2017016960 A1 | 2/2017 |
| WO | 2017140821 A1 | 8/2017 |
| WO | 2017216685 A1 | 12/2017 |
| WO | 2017216686 A1 | 12/2017 |
| WO | 2018019297 A1 | 2/2018 |
| WO | 2018022282 A1 | 2/2018 |
| WO | 2018047109 A1 | 3/2018 |
| WO | 2018085619 A1 | 5/2018 |
| WO | 2018130152 A1 | 7/2018 |

OTHER PUBLICATIONS

Pub Chem CID 8071, 1,2-Dimethoxyethane, Create date: Mar. 26, 2005.
Amii, et al., "Difluorinated Danishefsky's Diene: A Versatile C4 Building Block for the Fluorinated Six-Membered Rings", Organic Letters, vol. 3, No. 20, 2001, pp. 3103-3105.
El-Essawy, F.A., et al., "Anti-Hepatitis B Virus Activity of New 1,2,4-Triazol-2-yl- and 1,3,4-Oxadiazol-2-yl-2-pyridinone Derivatives", Zeitschrift fur Naturforschung C, vol. 63, Nos. 9-10, 2008, pp. 667-674.
Fecik, et al., "Chiral DNA Gyrase Inhibitors. 3. Probing the Chiral Preference of the Active Site of DNA Gyrase. Synthesis of 10-fluoro-6-methyl-6,7-dihydro-9-piperazinyl-2H-benzo[a]quinolizin-20-one-3-carboxylic Acid Analogues", J Med Chem, vol. 48, No. 4, Jan. 1, 2005, pp. 1229-1236.
Georgopapadakou, et al., "Monocyclic and Tricyclic Analos of Quinolones: Mechanism of Action", Antimicrobial Agents and Chemotherapy, vol. 31, No. 4, Apr. 1987, pp. 614-616.
Kaneko, M., et al., "A Novel Tricyclic Polyketide, Vanitaracin A, Specifically Inhibits the Entry of Hepatitis B and D Viruses by Targeting Sodium Taurocholate Cotransporting Polypeptide", J of Virol, vol. 89, No. 23, 2015, pp. 11945-11953.
Xu, B., et al., "A Facile Synthesis of Novel Tricyclic 4-Pyridones", Tetrahedron Letters, vol. 55, Issue 52, 2014, pp. 7194-7197.
International Search Report & Written Opinion dated Jul. 1, 2019 for corresponding PCT International Application PCT/US2019/027004.
International Search Report & Written Opinion dated Mar. 30, 2018 for PCT International Application PCT/US2017/059854.

Primary Examiner — Charanjit Aulakh
(74) Attorney, Agent, or Firm — Saul Ewing Arnstein & Lehr LLP; Domingos J. Silva; Kevin T. O'Brien

(57) ABSTRACT

The present disclosure relates to novel, scalable methods of making substituted tricyclic compounds that are useful to treat and/or prevent HBV and/or HBV-HDV infection and related conditions in a subject.

31 Claims, No Drawings

METHODS FOR PREPARING SUBSTITUTED PYRIDINONE-CONTAINING TRICYCLIC COMPOUNDS

CROSS-REFERENCE TO RELATED APPLICATIONS

The present application is a 35 U.S.C. § 371 national phase application from, and claims priority to, PCT International Patent Application No. PCT/US2019/027004, filed Apr. 11, 2019, which claims priority under 35 U.S.C. § 119(e) to U.S. Provisional Applications No. 62/656,605, filed Apr. 12, 2018, and No. 62/700,048, filed Jul. 18, 2018, all of which are hereby incorporated by reference herein in their entireties.

BACKGROUND OF THE INVENTION

Hepatitis B is one of the world's most prevalent diseases. Although most individuals resolve the infection following acute symptoms, approximately 30% of cases become chronic. 350-400 million people worldwide are estimated to have chronic hepatitis B, leading to 0.5-1 million deaths per year, due largely to the development of hepatocellular carcinoma, cirrhosis, and/or other complications. Hepatitis B is caused by hepatitis B virus (HBV), a noncytopathic, liver tropic DNA virus belonging to Hepadnaviridae family.

A limited number of drugs are currently approved for the management of chronic hepatitis B, including two formulations of alpha-interferon (standard and pegylated) and five nucleoside/nucleotide analogues (lamivudine, adefovir, entecavir, telbivudine, and tenofovir) that inhibit HBV DNA polymerase. At present, the first-line treatment choices are entecavir, tenofovir, or peg-interferon alfa-2a. However, peg-interferon alfa-2a achieves desirable serological milestones in only one third of treated patients, and is frequently associated with severe side effects. Entecavir and tenofovir require long-term or possibly lifetime administration to continuously suppress HBV replication, and may eventually fail due to emergence of drug-resistant viruses.

Hepatitis D virus (HDV) is a small circular enveloped RNA virus that can propagate only in the presence of HBV. In particular, HDV requires the HBV surface antigen protein to propagate itself. Infection with both HBV and HDV results in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B, hepatitis D has the highest mortality rate of all the hepatitis infections. The routes of transmission of HDV are similar to those for HBV. Infection is largely restricted to persons at high risk of HBV infection, particularly injecting drug users and persons receiving clotting factor concentrates.

Currently, there is no effective antiviral therapy available for the treatment of acute or chronic type D hepatitis. Interferon-alfa given weekly for 12 to 18 months is the only licensed treatment for hepatitis D. Response to this therapy is limited, as only about one-quarter of patients is serum HDV RNA undetectable 6 months post therapy.

Much research has been dedicated to the identification of novel agents that can be used to effectively treat and/or prevent HBV and/or HDV infection in a subject. Such agents should be easily and reproducibly prepared in large scale, so that they can be used to treat large number of patients infected with, or at risk on being infected with, HBV and/or HDV. There is thus a need to identify scalable synthetic routes for those anti-HBV and/or anti-HDV antiviral agents (as well as certain intermediates useful for preparing the same). The present invention addresses this need.

BRIEF SUMMARY OF INVENTION

The present invention relates, in part, to methods of preparing compound [I], or a salt or solvate thereof, wherein X is CH or N:

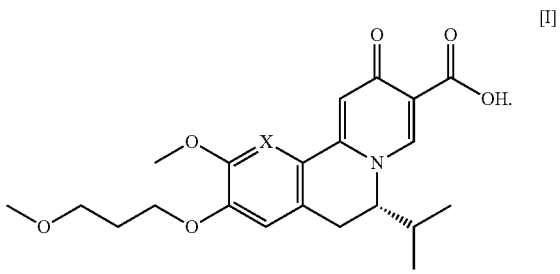

The present invention further relates, in part, to methods of preparing (S)-6-isopropyl-2-methoxy-3-(3-methoxypropoxy)-10-oxo-5,10-dihydro-6H-pyrido[1,2-h][1,7]naphthyridine-9-carboxylic acid [26], or a salt or solvate thereof:

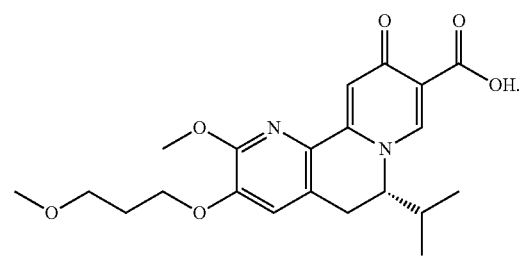

The present invention further relates, in part, to methods of preparing certain compounds that can be useful intermediates in preparing [I], [26], or any salt or solvate thereof.

DETAILED DESCRIPTION OF THE INVENTION

The invention relates, in certain aspects, to synthetic routes that allow for reproducible preparation of certain substituted tricyclic compounds. In certain embodiments, certain compounds contemplated within the invention are useful to treat and/or prevent HBV and/or HBV-HDV infection and related conditions in a subject. In other embodiments, the methods of the invention allow for large scale (i.e., multigram and/or multikilo) synthesis of [I], [IA], [IB], and related compounds. In yet other embodiments, the methods of the invention allow for enantiospecific synthesis of [I], [IA], [IB], and related compounds. In other embodiments, the methods of the invention allow for isolation of [I], [IA], [IB], and related compounds in high purity (i.e., ≥90%, ≥91%, ≥92%, ≥93%, ≥94%, ≥95%, ≥96%, ≥97%, ≥97.5%, ≥98%, ≥98.5%, ≥99%, ≥99.5%, ≥99.75%, ≥99.9%, or ≥99.5% purity, as determined by an analytical method, such as high-performance liquid chromatography (HPLC) or any other chromatographic method, IR, UV, NMR, and the like).

Certain compounds of interest were originally described in PCT Patent Application No. WO 2018/085619 (corresponding to PCT Application No. PCT/US2017/059854), which is incorporated herein in its entirety by reference.

Synthetic Methods

In certain embodiments, the present invention provides methods of preparing compound [I], or a salt or solvate thereof, wherein X is CH or N:

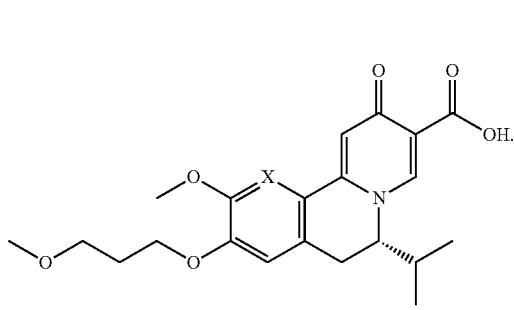

In certain embodiments, the compound is [(S)-6-isopropyl-2-methoxy-3-(3-methoxypropoxy)-10-oxo-5,10-dihydro-6H-pyrido[1,2-h][1,7]naphthyridine-9-carboxylic acid], [IA] or [26], or a salt or solvate thereof (X=N):

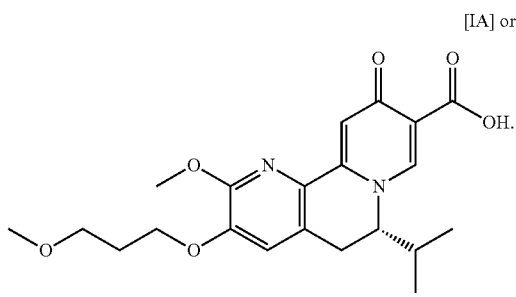

In certain embodiments, the compound is (S)-6-isopropyl-10-methoxy-9-(3-methoxypropoxy)-2-oxo-6,7-dihydro-2H-pyrido[2,1-a]isoquinoline-3-carboxylic acid [IB], or a salt or solvate thereof (X=CH):

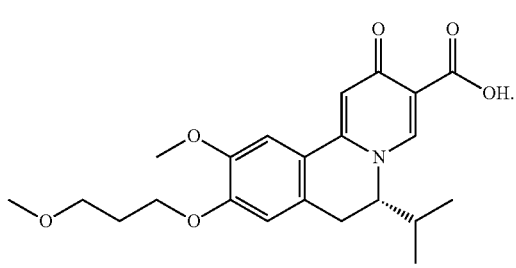

The following description exemplifies aspects of the invention for the instance where X=N, but the procedures and steps described herein are equally applicable to the corresponding intermediates and final product where X=CH.

In certain embodiments, any of the alkyl, cycloalkyl, phenyl, and/or benzyl groups recited herein are independently optionally substituted.

a. Synthesis of (S)-6-isopropyl-2-methoxy-3-(3-methoxypropoxy)-10-oxo-5,10-dihydro-6H-pyrido[1,2-h][1,7]naphthyridine-9-carboxylic acid [26]

In one aspect, the invention provides methods of preparing [26] from (S)-6-isopropyl-2-methoxy-3-(3-methoxypropoxy)-10-oxo-5,10-dihydro-6H-pyrido[1,2-h][1,7]naphthyridine-9-carboxylic ester [25], or a salt or solvate thereof:

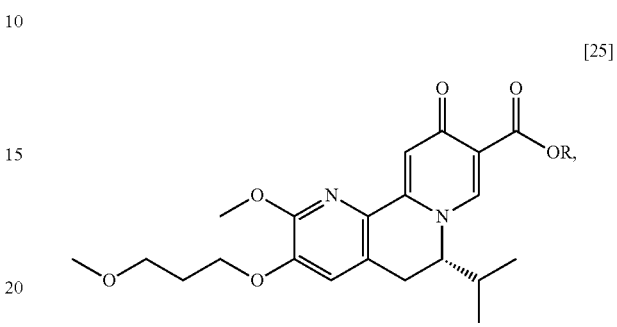

wherein R is $C_1$-$C_6$ alkyl, $C_3$-$C_8$ cycloalkyl, or benzyl.

In certain embodiments, [26] can be prepared according to the illustrative synthetic methods outlined in Scheme 1:

Scheme 1.

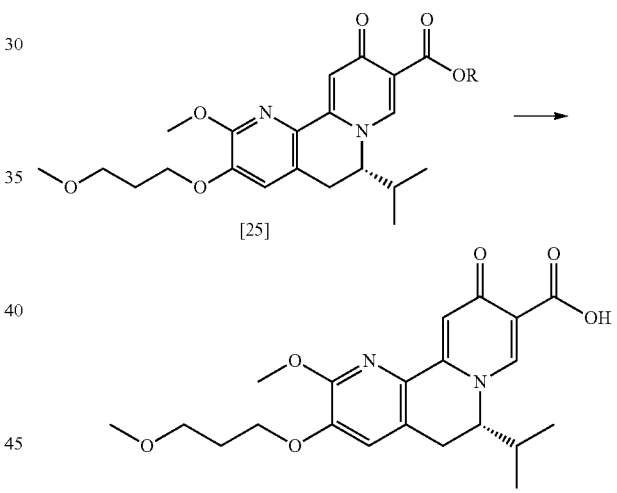

In certain embodiments, the invention provides a method of preparing [26], the method comprising a process of hydrolyzing (S)-6-isopropyl-2-methoxy-3-(3-methoxypropoxy)-10-oxo-5,10-dihydro-6H-pyrido[1,2-h][1,7]naphthyridine-9-carboxylic ester [25], or a salt or solvate thereof:

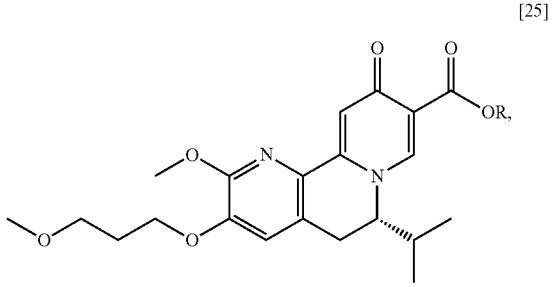

wherein R can be, in non-limiting instances, $C_1$-$C_6$ alkyl, $C_3$-$C_8$ cycloalkyl, or benzyl.

In certain embodiments, [25] is hydrolyzed by contacting that compound with at least one acid or at least one base. In other embodiments, the at least one acid comprises at least one of hydrochloric acid, sulfuric acid, trifluoroacetic acid, and phosphoric acid. In other embodiments, the at least one base comprises at least one of LiOH, NaOH, and KOH. In yet other embodiments, [25] is hydrolyzed by contacting that compound with the at least one acid or at least one base in a molar ratio of about 1:1 to about 1:3.

In certain embodiments, [25] is hydrolyzed in a solution comprising at least one solvent. In other embodiments, the solvent comprises at least one of methanol, water, ethanol, tetrahydrofuran (THF), dichloromethane (DCM), and 2-methyl-tetrahydrofuran (2-Me THF).

In certain embodiments, [26] is isolated by extracting that compound into an organic solvent to form an organic solution, washing the organic solution with an aqueous solvent, adjusting the pH of the solution to about pH 5-6, removing at least a portion of the organic solvent, and recrystallizing [26] in a solution comprising at least one alcohol. In other embodiments, [26] is extracted into ethyl acetate and recrystallized in ethanol.

b. Synthesis of (S)-6-isopropyl-2-methoxy-3-(3-methoxypropoxy)-10-oxo-5,10-dihydro-6H-pyrido[1,2-h][1,7]naphthyridine-9-carboxylic ester [25]

In one aspect, the invention provides methods of preparing [25] from protected (S)-1-(2-X-6-methoxy-5-(3-methoxypropoxy)pyridin-3-yl)-3-methylbutan-2-amine [20], or a salt or solvate thereof:

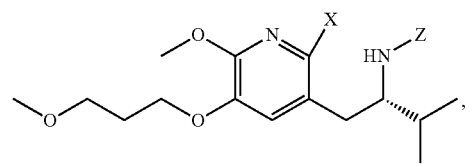

[20]

wherein X is selected from the group consisting of Cl, Br, and I, and Z is an amine protecting group.

In certain embodiments, [25] is prepared according to the synthetic methods outlined in Scheme 2:

Scheme 2.

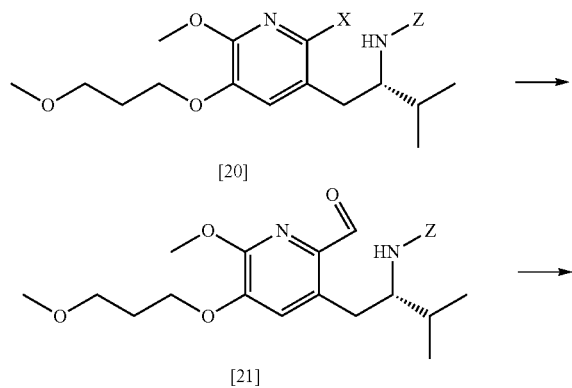

Synthesis of [25], according to Scheme 2:

In certain embodiments, [25] is prepared by a process comprising oxidizing and/or dehydrogenating (6S')-6-isopropyl-2-methoxy-3-(3-methoxypropoxy)-10-oxo-5,10,11,11a-tetrahydro-6H-pyrido[1,2-h][1,7]naphthyridine-9-carboxylic ester [24], or a salt or solvate thereof:

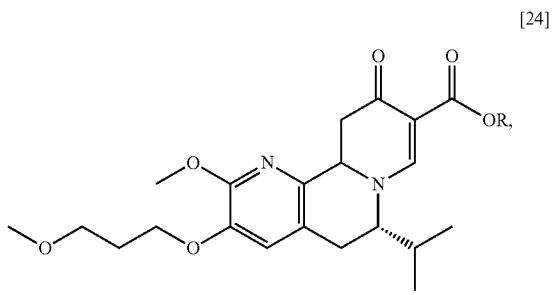

wherein R can be, in a non-limiting example, $C_1$-$C_6$ alkyl, $C_3$-$C_8$ cycloalkyl, or benzyl. In certain embodiments, R is ethyl. In other embodiments, R is tert-butyl.

In certain embodiments, [24] is contacted with a dehydrogenation reagent. In other embodiments, the reaction mixture formed by contacting the dehydrogenation reagent and [24] is further contacted with an acid.

In certain embodiments, the dehydrogenation reagent is contacted with [24] in a solution comprising at least one solvent comprising at least one of 2-methyl tetrahydrofuran and tetrahydrofuran.

In certain embodiments, the dehydrogenation reagent is an oxidizing reagent. In other embodiments, the dehydrogenation reagent comprises at least one of 2,3-dichloro-5,6-dicyano-1,4-benzoquinone (DDQ), p-chloranil, N-bromosuccinimide, iodine, and manganese dioxide.

In certain embodiments, the dehydrogenation reagent is contacted with [24] in a molar ratio of about 1:1 to about 3:1.

In certain embodiments, the dehydrogenation reagent is contacted with [24] at room temperature. In other embodiments, the dehydrogenation reagent is contacted with [24] at a temperature from about 20° C. to about 80° C.

In certain embodiments, the reaction mixture is contacted with the acid about 10 hours to about 30 hours after the dehydrogenation reagent is contacted with [24].

Synthesis of (6S)-6-isopropyl-2-methoxy-3-(3-methoxypropoxy)-10-oxo-5,10,11,11a-tetrahydro-611-pyrido[1,2-h][1,7]naphthyridine-9-carboxylic ester [24] according to Scheme 2

In certain embodiments, [24] is prepared by a process comprising coupling (S)-6-isopropyl-2-methoxy-3-(3-methoxypropoxy)-5,6-dihydro-1,7-naphthyridine [22], or a salt or solvate thereof, with alkyl 2-(ethoxymethylidene)-3-oxobutanoate [23]:

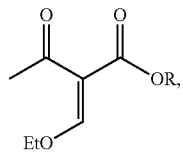

[23]

wherein R can be, in a non-limiting example, $C_1$-$C_6$ alkyl, $C_3$-$C_8$ cycloalkyl, or benzyl. In certain embodiments, R is ethyl. In other embodiments, R is tert-butyl.

In certain embodiments, [24] is prepared by contacting [22] with [23].

In certain embodiments, [22] is contacted with [23] in a solution comprising at least one solvent comprising at least one of water, ethanol, isopropanol, 2-methyl tetrahydrofuran, tetrahydrofuran, and water/ethanol mixture (ranging from 1:20 to 20:1). In other embodiments, [22] is contacted with [23] in a solution selected from the group consisting of 100% water, 100% ethanol, and 50% water/50% ethanol.

In certain embodiments, [22] is contacted with [23] in a molar ratio of about 1:1 to about 1:5.

In certain embodiments, [22] is contacted with [23] at a temperature from about 20° C. to about 100° C.

Synthesis of (S)-6-isopropyl-2-methoxy-3-(3-methoxypropoxy)-5,6-dihydro-1,7-naphthyridine [22], according to Scheme 2

In certain embodiments, [22] is prepared by a process comprising reacting a Grignard or alkyl lithium reagent and a carbonyl source with protected (S)-1-(2-X-6-methoxy-5-(3-methoxypropoxy)pyridin-3-yl)-3-methylbutan-2-amine [20], or a salt or solvate thereof:

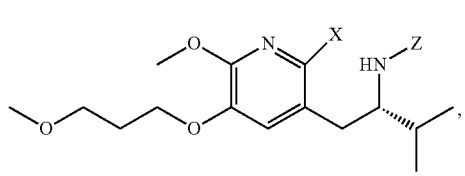

[20]

wherein X is selected from the group consisting of Cl, Br, and I, and Z is an amine protecting group. In certain embodiments, the reaction of the Grignard or alkyl lithium reagent, carbonyl source, and [20] forms protected tert-butyl (S)-(1-(2-formyl-6-methoxy-5-(3-methoxypropoxy) pyridin-3-yl)-3-methylbutan-2-yl) amine [21], or a salt or solvate thereof:

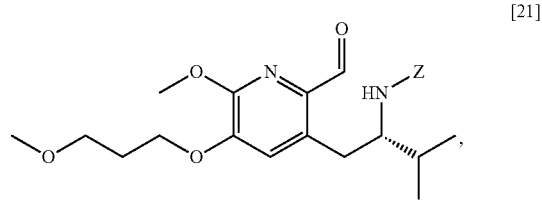

[21]

wherein Z is an amine protecting group.

In certain embodiments, [21] spontaneously cyclizes to [22].

In certain embodiments, [22] is prepared by a process comprising contacting at least one Grignard reagent or alkyl lithium reagent with [20], thereby generating an activated intermediate, and contacting the activated intermediate with a carbonyl source.

In certain embodiments, the carbonyl source comprises at least one of dimethylformamide, formyl-morpholine, formyl-piperidine, and so forth.

In certain embodiments, Z is a protecting group comprising at least one of tert-butyloxycarbonyl (BOC), carbobenzyloxy (Cbz), and optionally substituted benzyl (such as para-methoxybenzyl).

In certain embodiments, the at least one Grignard reagent or alkyl lithium reagent comprises at least one of MeLi, n-BuLi, i-PrMgCl, i-PrMgCl.LiCl, mixture of i-PrMgCl and n-butyl lithium (from about 1:1 to 1:3 ratio, for example 1:2 ratio), MeMgCl, MeMgBr, and cyclohexylmagnesium chloride lithium chloride.

In certain embodiments, the at least one Grignard reagent or alkyl lithium reagent is contacted with [20] in a solution comprising at least one anhydrous, aprotic solvent comprising at least one of diethyl ether, 2-methyl tetrahydrofuran, and tetrahydrofuran.

In certain embodiments, the at least one Grignard reagent or alkyl lithium reagent is contacted with [20] in a molar ratio of about 5:1 to about 2:1. In other embodiments, the activated intermediate is contacted with the carbonyl source in a molar ratio of about 1:1 to about 1:5.

In certain embodiments, the at least one Grignard reagent or alkyl lithium reagent is contacted with [20] at a temperature of about −80° C. to about 0° C. In other embodiments, the activated intermediate is contacted with the carbonyl source (such as dimethylformamide) at a temperature from about −80° C. to about 0° C.

In certain embodiments, [21] spontaneously converts to [22] upon warming to a temperature higher than about 20° C.

In certain embodiments, [25] is prepared according to the synthetic methods outlined in Scheme 3:

Scheme 3.

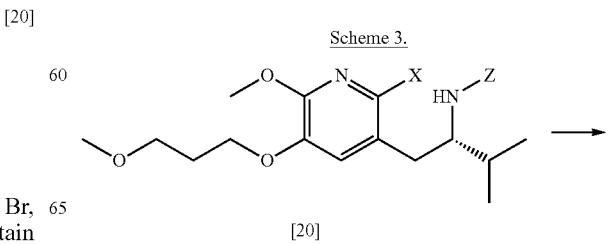

[20]

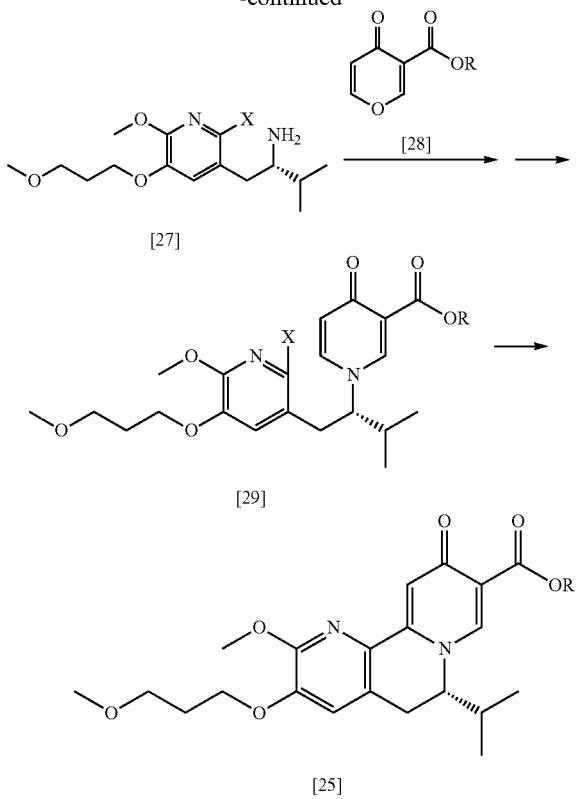

Synthesis of [25], According to Scheme 3:

In certain embodiments, [25] is prepared by a process comprising promoting intramolecular ring formation in (S)-1-(1-(2-X-6-methoxy-5-(3-methoxypropoxy)pyridin-3-yl)-3-methylbutan-2-yl)-4-oxo-1,4-dihydropyridine-3-carboxylic ester [29], or a salt or solvate thereof:

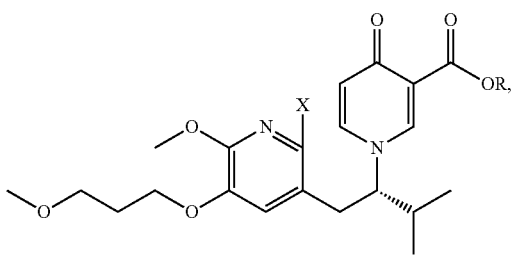

such that the pyridyl halide couples to the 6-position of the pyridinone, wherein X is selected from the group consisting of Cl, Br, and I, and wherein R is, in a non-limiting example, $C_1$-$C_6$ alkyl, $C_3$-$C_8$ cycloalkyl, or benzyl. In certain embodiments, R is tert-butyl. In certain embodiments, R is ethyl. In yet other embodiments, X is bromide.

In certain embodiments, [25] is prepared by a process comprising contacting [29] with a coupling catalyst and at least one base. In certain embodiments, the coupling catalyst comprises a palladium complex. In other embodiments, the coupling catalyst comprises a palladium complex and at least one palladium coordinating ligand. In yet other embodiments, the palladium complex is palladium bromide (PdBr$_2$). In yet other embodiments, the coupling catalyst is contacted with [29] in a molar ratio of about 1:10 to about 1:200, or about 1:20. In yet other embodiments, the at least one base is an acetate salt. In yet other embodiments, the acetate salt is sodium acetate. In yet other embodiments, the at least one base is contacted with [29] in a molar ratio of about 1:1 to about 3:1, or about 2:1.

In certain embodiments, [29] is contacted with the coupling catalyst and the base at a temperature of about 60° C. to about 100° C. In other embodiments, the reaction mixture is contacted with the coupling catalyst at a temperature of about 95° C.

In certain embodiments, [29] is contacted with the coupling catalyst and the base in a solvent. In other embodiments, the solvent comprises dimethylacetamide (DMAc) and/or toluene.

In certain embodiments, [29] is contacted with the coupling catalyst and the base under an inert atmosphere. In other embodiments, the inert atmosphere comprises at least one gas selected from the group consisting of nitrogen and argon.

Synthesis of (S)-1-(1-(2-X-6-methoxy-5-(3-methoxypropoxy)pyridin-3-yl)-3-methylbutan-2-yl)-4-oxo-1,4-dihydropyridine-3-carboxylic ester [29], according to Scheme 3

In certain embodiments, [29] is prepared by a process comprising contacting (S)-1-(2-bromo-6-methoxy-5-(3-methoxypropoxy)pyridin-3-yl)-3-methylbutan-2-amine [27], or a salt or solvate thereof, with 4-oxo-4H-pyran-3-carboxylic ester [28], or a salt or solvate thereof, in a reaction mixture:

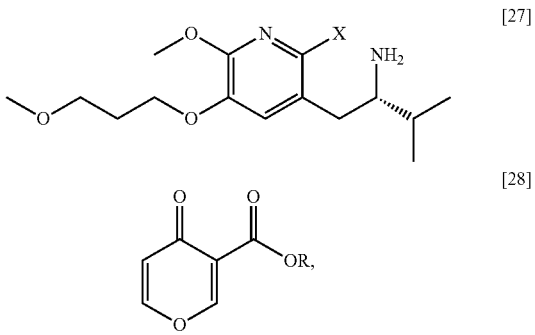

wherein X is selected from the group consisting of Cl, Br, and I, and wherein R is, in a non-limiting example, $C_1$-$C_6$ alkyl, $C_3$-$C_8$ cycloalkyl, or benzyl. In certain embodiments, R is tert-butyl. In other embodiments, R is ethyl. In yet other embodiments X is bromide.

In certain embodiments, the reaction mixture further comprises a solvent. In other embodiments, the solvent comprises ethanol and acetic acid in a molar ratio of about 3:1.

In certain embodiments, the reaction mixture is contacted with [28] at a temperature of about 20° C. to about 100° C. In other embodiments, the reaction mixture is heated to about 80° C. before being allowed to cool to room temperature.

Synthesis of (S)-1-(2-bromo-6-methoxy-5-(3-methoxypropoxy)pyridin-3-yl)-3-methylbutan-2-amine [27] according to Scheme 3

In certain embodiments, [27] is prepared by a process comprising removing the protecting group Z from protected (S)-1-(2-X-6-methoxy-5-(3-methoxypropoxy)pyridin-3-yl)-3-methylbutan-2-amine [20], or a salt or solvate thereof:

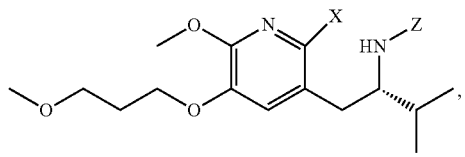

wherein X is selected from the group consisting of Cl, Br, and I, and Z is an amine protecting group. In certain embodiments, Z is a protecting group comprising at least one of tert-butyloxycarbonyl (BOC), carbobenzyloxy (Cbz), and optionally substituted benzyl (such as para-methoxybenzyl).

In certain embodiments, [20] is contacted with at least one acid to form a reaction mixture. In other embodiments, [20] is contacted with HCl, HBr, HI, trifluoroacetic acid (TFA), or sulfuric acid. In yet other embodiments, [20] is contacted with the acid (such as HCl) in a molar ratio of about 1:1 to about 1:3. In yet other embodiments, the method further comprises contacting the reaction mixture with at least one base after the reaction mixture has been allowed to react. In yet other embodiments, the at least one base is sodium bicarbonate.

c. Synthesis of protected (S)-1-(2-X-6-methoxy-5-(3-methoxypropoxy)pyridin-3-yl)-3-methylbutan-2-amine [20]

In one aspect, the invention provides methods of preparing [20] from protected (S)-1-(6-methoxy-5-(3-methoxypropoxy)pyridin-3-yl)-3-methylbutan-2-amine [11], or a salt or solvate thereof:

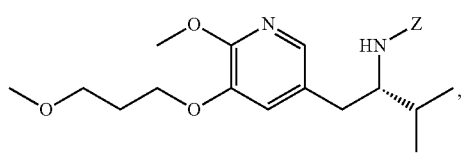

wherein Z is an amine protecting group.

In certain embodiments, [20] is prepared according to the synthetic methods outlined in Scheme 4:

Scheme 4.

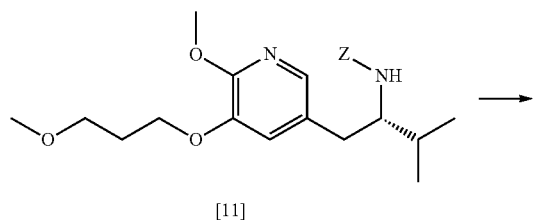

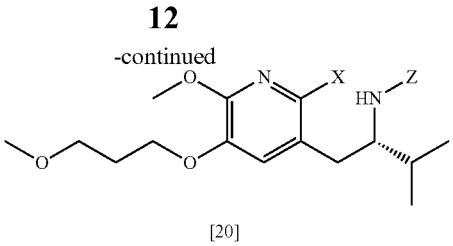

In certain embodiments, [20] is prepared by a process comprising contacting a halogenating agent with [11], wherein X is selected from the group consisting of Cl, Br, and I.

In certain embodiments, Z is a protecting group comprising at least one of tert-butyloxycarbonyl (BOC), carbobenzyloxy (Cbz), and optionally substituted benzyl.

In certain embodiments, the halogenating agent comprises at least one of N-bromosuccinimide (NBS), $Br_2$/AcOH, pyridinium tribromide/DMF, N-iodosuccinimide (NIS), and N-chlorosuccinimide (NCS).

In certain embodiments, the halogenating agent is contacted with [11] in a solution comprising at least one solvent comprising at least one of dichloromethane, chloroform, cyclopentyl methyl ether, and dimethylformamide. In certain embodiments, the halogenating agent is contacted with [11] at a temperature of about 20° C. to about 40° C.

In certain embodiments, the halogenating agent is contacted with [11] in a molar ratio of about 1:1 to about 3:2.

d. Synthesis of protected (S)-(1-(6-methoxy-5-(3-methoxypropoxy)pyridin-3-yl)-3-methylbutan-2-yl)amine [11]

In certain embodiments, the invention provides methods of preparing protected (S)-(1-(6-methoxy-5-(3-methoxypropoxy)pyridin-3-yl)-3-methylbutan-2-yl)amine [11] from 5-X-2-methoxy-3-(3-methoxypropoxy)pyridine [4], or a salt or solvate thereof:

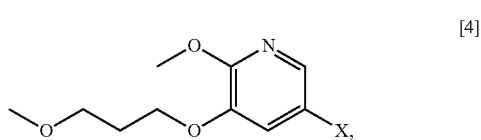

wherein X is selected from the group consisting of Cl, Br, and I.

In certain embodiments, [11] is prepared according to the synthetic method outlined in Scheme 5:

Scheme 5.

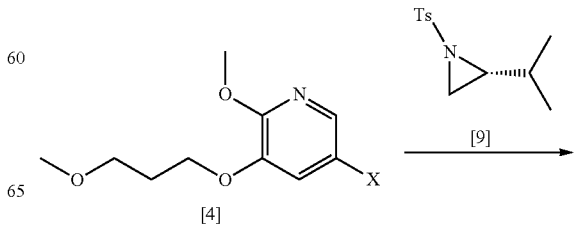

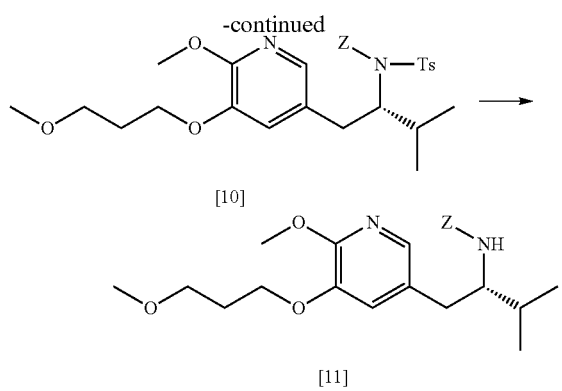

Synthesis of protected (S)-(1-(6-methoxy-5-(3-methoxypropoxy)pyridin-3-yl)-3-methylbutan-2-yl) amine [11] according to Scheme 5

In certain embodiments, [11] is prepared by a process comprising reacting [4] with a Grignard reagent to form a magnesium halide intermediate, which is then reacted with a reactant having an electrophilic carbon. Alternatively, [11] is prepared by a process comprising reacting [4] with an alkyl lithium reagent to form a reactive lithiated intermediate, which is then reacted with a reactant having an electrophilic carbon.

In certain embodiments, [4] is contacted with a Grignard reagent, thereby forming a reactive magnesium halide intermediate. In other embodiments, [4] is contacted with an alkyl lithium reagent, thereby forming a reactive lithiated intermediate. In yet other embodiments, the reactive intermediate is contacted with (R)-2-isopropyl-1-tosylaziridine and at least one copper salt, thereby forming (S)-N-(1-(6-methoxy-5-(3-methoxypropoxy)pyridin-3-yl)-3-methylbutan-2-yl)-4-methylbenzenesulfonamide [10], Z=H. In yet other embodiments, the (S)-N-(1-(6-methoxy-5-(3-methoxypropoxy)pyridin-3-yl)-3-methylbutan-2-yl)-4-methylbenzenesulfonamide is contacted with an amine protecting group precursor, thereby forming a protected (S)-N-(1-(6-methoxy-5-(3-methoxypropoxy)pyridin-3-yl)-3-methylbutan-2-yl)-4-methyl benzenesulfonamide [10]:

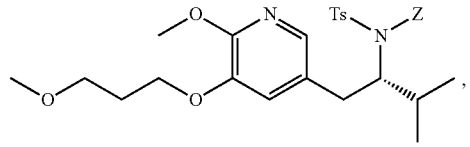

wherein Z is an amine protecting group.

In yet other embodiments, the tosylate (Ts) group is removed.

In certain embodiments, the Grignard or alkyl lithium reagent comprises at least one of MeLi, t-BuLi, i-PrMgCl, i-PrMgCl.LiCl, mixture of i-PrMgCl and n-butyl lithium (1:1 to 1:3 ratio, for example 1:2 ratio), MeMgCl, MeMgBr, and cyclohexylmagnesium chloride lithium chloride.

In certain embodiments, the at least one copper salt comprises at least one of CuI, CuBr, CuBr.Me$_2$S, and CuCN.

In certain embodiments, the amine protecting group precursor comprises at least one of tert-butyloxycarbonyl (BOC) anhydride, carbobenzyloxy (Cbz) anhydride, and optionally substituted benzyl chloride. In other embodiments, Z is a protecting group comprising at least one of tert-butyloxycarbonyl (BOC), carbobenzyloxy (Cbz), and optionally substituted benzyl.

In certain embodiments, [4] and the Grignard/alkyl lithium reagent are contacted in a molar ratio of about 1:1.1 to about 1:2.

In certain embodiments, [4] and the Grignard/alkyl lithium reagent are contacted at a temperature of about −10° C. to about 60° C.

In certain embodiments, the reactive intermediate and the (R)-2-isopropyl-1-tosylaziridine [9] are contacted in a molar ratio of about 1:0.50 to about 1:1.

In certain embodiments, the reactive intermediate and the at least one copper salt are contacted in a molar ratio of about 20:1 to about 10:1.

In certain embodiments, the reactive intermediate, the (R)-2-isopropyl-1-tosylaziridine, and the at least one copper salt are contacted at a temperature of about 10° C. to about 50° C.

In certain embodiments, the (S)-N-(1-(6-methoxy-5-(3-methoxypropoxy)pyridin-3-yl)-3-methylbutan-2-yl)-4-methylbenzenesulfonamide [10], Z=H, is contacted with the amine protecting group precursor in a molar ratio of about 1:1 to about 1:4. In other embodiments, the (S)-N-(1-(6-methoxy-5-(3-methoxypropoxy)pyridin-3-yl)-3-methylbutan-2-yl)-4-methylbenzenesulfonamide [10], Z=H, is contacted with the amine protecting group precursor at a temperature of about 20° C. to about 40° C.

In certain embodiments, any of the steps in Scheme 5 can take place in a solution independently comprising at least one solvent comprising at least one of diethyl ether, 2-methyl tetrahydrofuran, tetrahydrofuran, and any other non-protic organic solvent.

In certain embodiments, the tosylate group in [10] is removed by contacting the protected (S)-N-(1-(6-methoxy-5-(3-methoxypropoxy)pyridin-3-yl)-3-methylbutan-2-yl)-4-methyl benzenesulfonamide [10] with iodine and magnesium metal.

In certain embodiments, [11] is prepared according to the synthetic method outlined in Scheme 6:

Scheme 6.

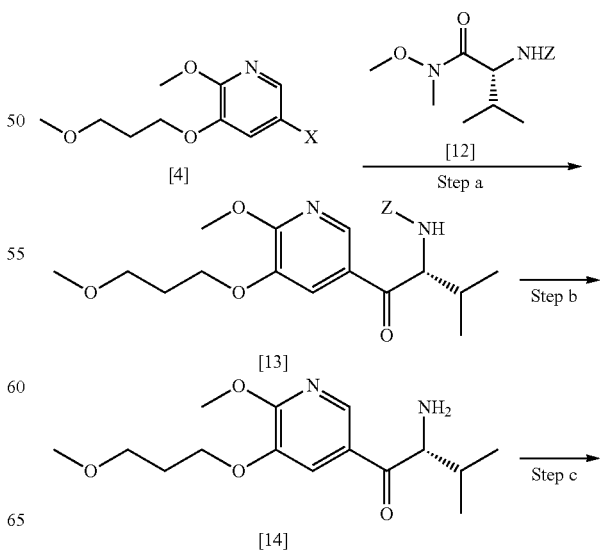

-continued

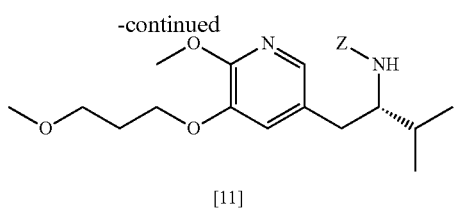

[11]

Synthesis of protected (S)-(1-(6-methoxy-5-(3-methoxypropoxy)pyridin-3-yl)-3-methylbutan-2-yl) amine [11], according to Scheme 6

In certain embodiments, in step (a) of Scheme 6 [4] is contacted with a first Grignard or alkyl lithium reagent, thereby forming a first reactive intermediate. In other embodiments, in step (a) of Scheme a second Grignard or alkyl lithium reagent is contacted with a protected (R)-2-amino-N-methoxy-N,3-dimethylbutanamide [12]:

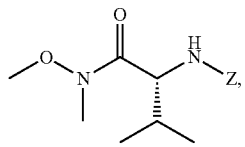

wherein Z is an amine protecting group, thereby forming a second reactive intermediate. In yet other embodiments, in step (a) of Scheme the first reactive intermediate and the second reactive intermediate are contacted, thereby forming protected N-[(2R)-1-[6-methoxy-5-(3-methoxypropoxy) pyridin-3-yl]-3-methyl-1-oxobutan-2-yl]amine [13]:

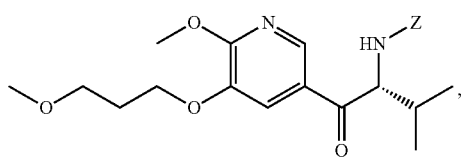

wherein Z is an amine protecting group. In yet other embodiments, in step (d) at least one reducing reagent is contacted with [13].

In certain embodiments, the first Grignard or alkyl lithium reagent comprises at least one of MeLi, t-BuLi, i-PrMgCl, i-PrMgCl.LiCl, mixture of i-PrMgCl and n-butyl lithium (1:1 to 1:3 ratio, for example 1:2 ratio), MeMgCl, MeMgBr, and cyclohexylmagnesium chloride lithium chloride. In other embodiments, the second Grignard or alkyl lithium reagent comprises at least one of MeLi, t-BuLi, i-PrMgCl, i-PrMgCl.LiCl, mixture of i-PrMgCl and n-butyl lithium (1:1 to 1:3 ratio, for example 1:2 ratio), MeMgCl, MeMgBr, and cyclohexylmagnesium chloride lithium chloride.

In certain embodiments, any of the substeps in step (a) independently takes place in an aprotic, anhydrous solution comprising at least one of diethyl ether, 2-methyl tetrahydrofuran, and tetrahydrofuran.

In certain embodiments, [4] is contacted with the first Grignard or alkyl lithium reagent in a molar ratio of about 1:1 to about 1:2.

In certain embodiments, [12] is contacted with the second Grignard or alkyl lithium reagent in a molar ratio of about 1:1 to about 1:2.

In certain embodiments, the at least one reducing reagent comprises a gallium (III) salt and a silyl hydride, any source of palladium, or any source of platinum.

In certain embodiments, step (b) takes place in a solution comprising at least one of dichloromethane, dichloroethane, and chloroform.

In certain embodiments, step (b) takes place at a temperature of about 20° C. to about 100° C.

In certain embodiments, step (b) yields (S)-1-(6-methoxy-5-(3-methoxypropoxy)pyridin-3-yl)-3-methylbutan-2-amine [14]. In other embodiments, in step (c) an amine protecting group precursor is contacted with [14].

In certain embodiments, the amine protecting group precursor is a protecting group precursor selected from the group consisting of tert-butyloxycarbonyl (BOC) anhydride and carbobenzyloxy (Cbz) anhydride.

In certain embodiments, 1111 is prepared according to the synthetic method outlined in Scheme 7:

Scheme 7.

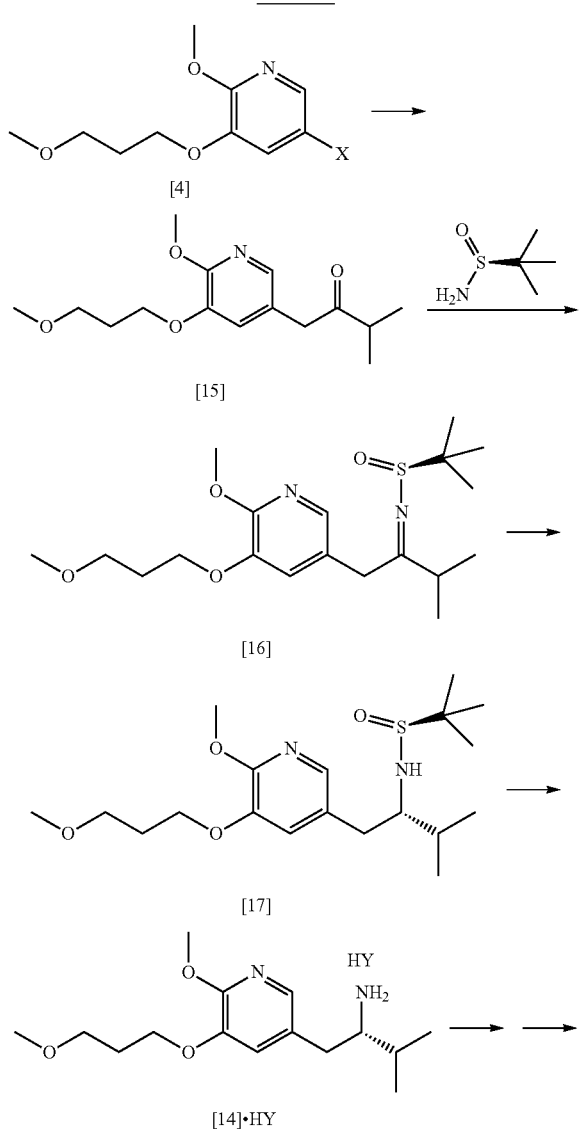

-continued

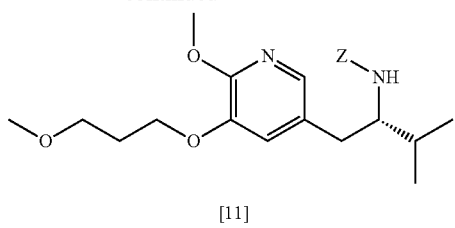

[11]

In certain embodiments, 1111 is prepared according to the synthetic method outlined in Scheme 8:

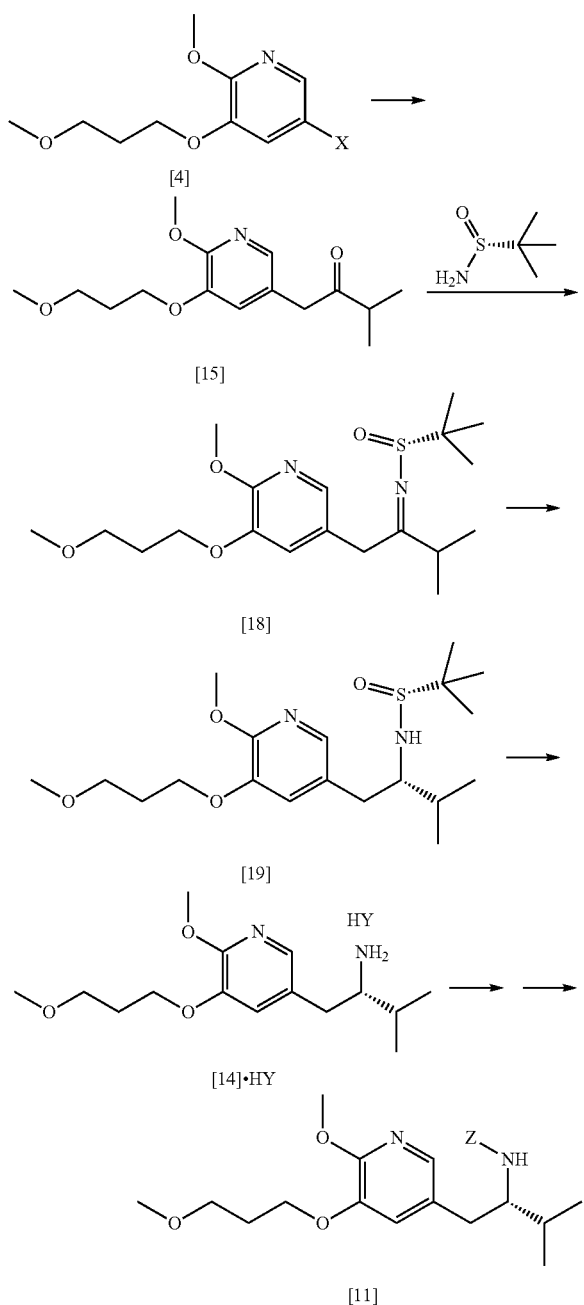

Synthesis of 1-(6-methoxy-5-(3-methoxypropoxy)pyridin-3-yl)-3-methylbutan-2-one [15], according to Schemes 7-8

In certain embodiments, [15] is prepared by a process comprising contacting [4] with 3-methylbutan-2-one and a strong base to form a reaction mixture. In other embodiments, the reaction mixture is contacted with a coupling catalyst.

In certain embodiments, the strong base is at least one alkoxide, such as but not limited to a tert-butoxide.

In certain embodiments, the coupling catalyst comprises a palladium complex. In other embodiments, the coupling catalyst comprises a palladium complex and at least one palladium coordinating ligand. In yet other embodiments, the coupling catalyst comprises $Pd_2(dba)_3$ and at least one chelating phosphine ligand, such as but not limited to 4,5-bis(diphenylphosphino)-9,9-dimethylxanthene (Xantphos). In yet other embodiments, the palladium complex is contacted to the reaction mixture in a molar ratio (with respect to [4]) of about 1:10 to about 1:200.

In certain embodiments, [4] and the 3-methylbutan-2-one are contacted in a molar ratio of about 1:1 to about 1:4. In other embodiments, [4] and the strong base are contacted in a molar ratio of about 1:2 to about 1:5.

In certain embodiments, [4] is contacted with 3-methylbutan-2-one and the strong base at a temperature of about 20° C. to about 40° C. In other embodiments, the reaction mixture is contacted with the coupling catalyst at a temperature of about 60° C. to about 100° C.

Synthesis of (S)-N-(1-(6-methoxy-5-(3-methoxypropoxy)pyridin-3-yl)-3-methyl butan-2-ylidene)-2-methylpropane-2-sulfinamide [16], and (R)-N-(1-(6-methoxy-5-(3-methoxypropoxy)pyridin-3-yl)-3-methylbutan-2-ylidene)-2-methylpropane-2-sulfinamide [18], according to Schemes 7-8

In certain embodiments, (S)-N-(1-(6-methoxy-5-(3-methoxypropoxy)pyridin-3-yl)-3-methylbutan-2-ylidene)-2-methylpropane-2-sulfinamide [16] and (R)-N-(1-(6-methoxy-5-(3-methoxypropoxy)pyridin-3-yl)-3-methylbutan-2-ylidene)-2-methylpropane-2-sulfinamide 1181 are prepared from [15] through analogous methods.

In certain embodiments, [16] or [18] is prepared by a process comprising contacting [15] with at least one Lewis acid and one 2-methylpropane-2-sulfinamide selected from (S)-2-methylpropane-2-sulfinamide and (R)-2-methylpropane-2-sulfinamide.

In certain embodiments, the at least one Lewis acid is at least one s of $Ti(OEt)_4$, $Ti(OiPr)_4$, $TiCl_4$, $TiCl_2(OCH(CH_3)_2)_2$, and $TiCl(OCH(CH_3)_2)_3$.

In certain embodiments, [15], the at least one Lewis acid, and the 2-methylpropane-2-sulfinamide are contacted at a temperature of about 60° C. to about 100° C.

In certain embodiments, [15] is contacted with the at least one Lewis acid in a molar ratio of about 1:2 to about 1:4. In certain embodiments, [15] is contacted with the 2-methylpropane-2-sulfinamide in a molar ratio of about 1:1 to about 1:2.

Synthesis of (S)-N-((S)-1-(6-methoxy-5-(3-methoxypropoxy)pyridin-3-yl)-3-methylbutan-2-yl)-2-methylpropane-2-sulfinamide [17], according to Scheme 7

In certain embodiments, (S)-N-((S)-1-(6-methoxy-5-(3-methoxypropoxy)pyridin-3-yl)-3-methylbutan-2-yl)-2- methylpropane-2-sulfinamide [17] is prepared by a process comprising contacting [16] with at least one reducing reagent.

In certain embodiments, the at least one reducing reagent is diisobutylaluminum hydride (DIBAL-H).

In certain embodiments, [16] is contacted with the at least one reducing reagent in a solution comprising at least one of diethyl ether, 2-methyl tetrahydrofuran, and tetrahydrofuran.

In certain embodiments, [16] is contacted with the at least one reducing reagent in a molar ratio of about 1:2 to about 1:4. In certain embodiments, [16] is contacted with the at least one reducing reagent at a temperature below about −20° C.

Synthesis of (R)-N-((S)-1-(6-methoxy-5-(3-methoxypropoxy)pyridin-3-yl)-3-methylbutan-2-yl)-2-methylpropane-2-sulfinamide [19], according to Scheme 8

This synthesis can be performed using a similar procedure to that exemplified elsewhere herein for the transformation of [16] to [17].

Synthesis of protected (S)-(1-(6-methoxy-5-(3-methoxypropoxy)pyridin-3-yl)-3-methylbutan-2-yl) amine [11] from (S)-N-((S)-1-(6-methoxy-5-(3-methoxypropoxy)pyridin-3-yl)-3-methylbutan-2-yl)-2-methylpropane-2-sulfinamide [17] or (R)-N-((S)-1-(6-methoxy-5-(3-methoxypropoxy)pyridin-3-yl)-3-methylbutan-2-yl)-2-methylpropane-2-sulfinamide [19]

In certain embodiments, [11] is prepared by a process comprising contacting [17] or [19] with at least one acid, thereby forming (2S)-1-[6-methoxy-5-(3-methoxypropoxy)pyridin-3-yl]-3-methylbutan-2-amine acid addition salt [14].HY. In certain embodiments, the contacting is carried out in a solution comprising at least one of diethyl ether, 2-methyl tetrahydrofuran, tetrahydrofuran, dioxane, dichloromethane, and chloroform. In other embodiments, [14].HY is contacted with at least one base, thereby forming [14]. In yet other embodiments, [14] is contacted with an amine protecting group precursor.

In certain embodiments, the at least one acid is an acid halide, selected from the group consisting of HCl, HBr, and HI. In other embodiments, [14].HY is an acid addition salt wherein Y is selected from the group consisting of Cl, Br, and I.

In certain embodiments, the amine protecting group precursor is selected from the group consisting of tert-butyloxycarbonyl (BOC) anhydride and carbobenzyloxy (Cbz) anhydride.

e. Synthesis of 5-bromo-2-methoxy-3-(3-methoxypropoxy)pyridine [4]

In one aspect, the invention provides methods of preparing 5-X-2-methoxy-3-(3-methoxypropoxy)pyridine [4], or a salt or solvate thereof:

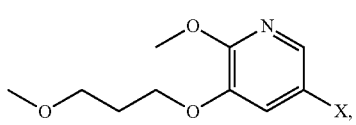

wherein X is selected from the group consisting of Cl, Br, and I. In certain embodiments, X is Br.

In certain embodiments, [4] can be prepared according to the synthetic methods outlined in Schemes 9-10:

Scheme 9.

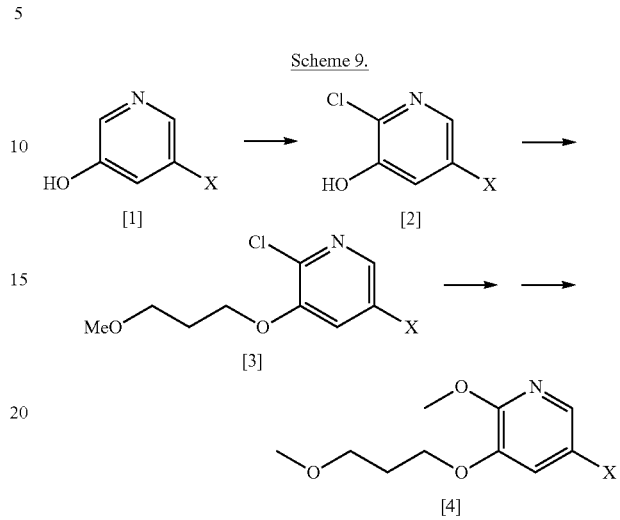

Scheme 10.

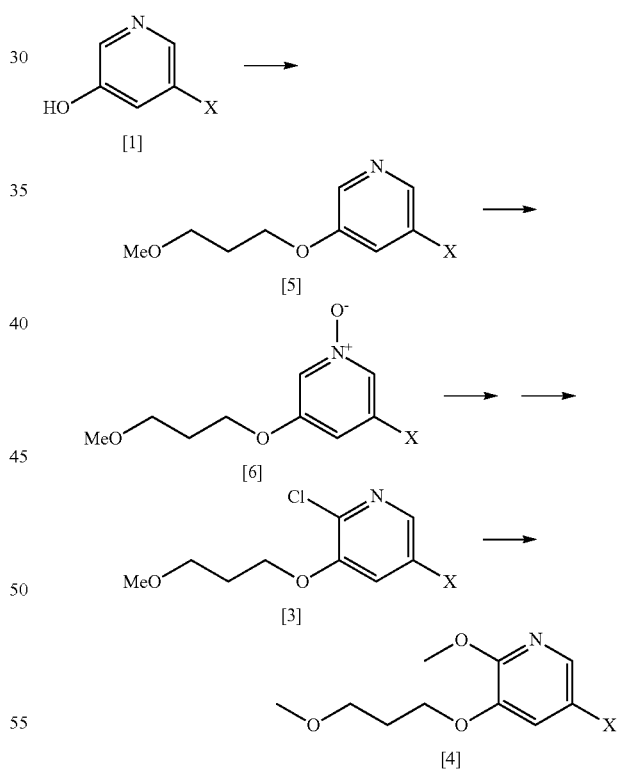

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It should be contemplated that the invention includes each and every one of the synthetic schemes described and/or depicted herein.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in pharmaceutical science, separation science, and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is $(C_1-C_3)$alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1-C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is $(C_1-C_6)$alkyl, such as, but not limited to, ethyl, methyl, isopropyl, isobutyl, n-pentyl, n-hexyl and cyclopropylmethyl.

As used herein, a "carbonyl source" refers to a reagent comprising a formyl group [—C(=O)H] attached to a leaving group (such as, for example, a phenoxide, a thiphenoxide, an alkoxide, a thioalkoxide, or an amine anion), whereby nucleophilic attack of a nucleophile on the carbonyl source leads to formylation (carbonylation) of the nucleophile and departure of the leaving group. Non-limiting examples of carbonyl sources include, but are not limited to, dimethylformamide, formyl-morpholine, and formyl-piperidine.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, the term "substituted" refers to that an atom or group of atoms has replaced hydrogen as the substituent attached to another group.

As used herein, the term "substituted alkyl" or "substituted cycloalkyl" refers to alkyl or cycloalkyl, as defined elsewhere herein, substituted by one, two or three substituents independently selected from the group consisting of halogen, —OH, alkoxy, tetrahydro-2-H-pyranyl, —$NH_2$, —NH($C_1$-$C_6$ alkyl), —N($C_1$-$C_6$ alkyl)$_2$, 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C≡N, —C(=O)$NH_2$, —C(=O)NH($C_1$-$C_6$)alkyl, —C(=O)N(($C_1$-$C_6$)alkyO$_2$, —$SO_2NH_2$, —$SO_2$NH($C_1$-$C_6$ alkyl), —$SO_2$N($C_1$-$C_6$ alkyl)$_2$, —C(=NH)$NH_2$, and —$NO_2$, in certain embodiments containing one or two substituents independently selected from halogen, —OH, alkoxy, —$NH_2$, trifluoromethyl, —N($CH_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For benzyl and aryl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, $C_3$-$C_8$ cycloalkyl, —OH, $C_1$-$C_6$ alkoxy, halo, amino, acetamido, and nitro. As used herein, where a substituent is an alkyl or alkoxy group, the carbon chain may be branched, straight or cyclic.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

The following non-limiting abbreviations are used herein: AcOH, acetic acid; Boc, tert-Butyloxycarbonyl; CPME, cyclopentyl methyl ether; Dba, dibenzylideneacetone; DCM, dichloromethane; DMAC or DMAc, dimethylacetamide; DMAP, 4-dimethylaminopyridine; DMF, dimethylformamide; EtOAc, ethyl acetate; EtOH, ethanol; Et$_3$N, trimethylamine; HBV, hepatitis B virus; HDV, hepatitis D virus; HPLC, high performance liquid chromatography; LC-MS, liquid chromatography-mass spectrometry; MTBE, methyl tert-butyl ether; THF, tetrahydrofuran; 2-MeTHF, 2-methyl tetrahydrofuran; RBF, round bottom flask; UPLC, Ultra Performance Liquid Chromatography; Xantphos, 4,5-Bis(diphenylphosphino)-9,9-dimethylxanthene.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

It should be noted in certain protocols the term/unit "Vol" or "volume" or "volumes" is used to denote a relative amount of solvent volume to be used, and does not limit the scope of the invention in any manner.

Example 1: Synthesis of 5-bromo-2-methoxy-3-(3-methoxypropoxy)pyridine [4], according to Schemes 9-10

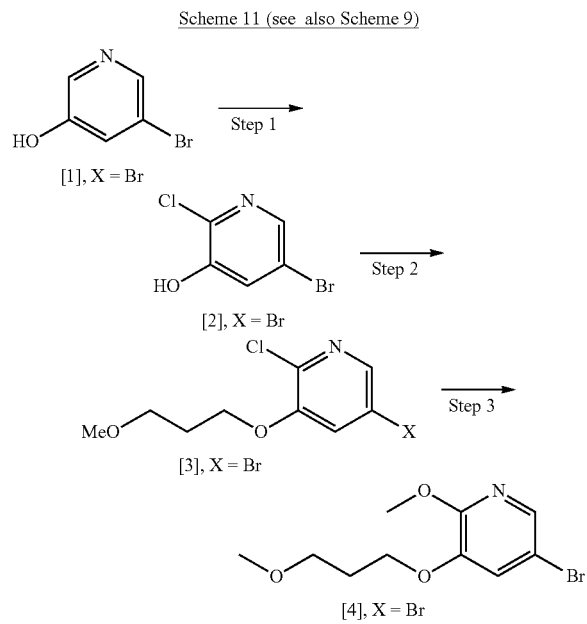

Step 1: Synthesis of 5-bromo-2-chloropyridin-3-ol [2], X=Br

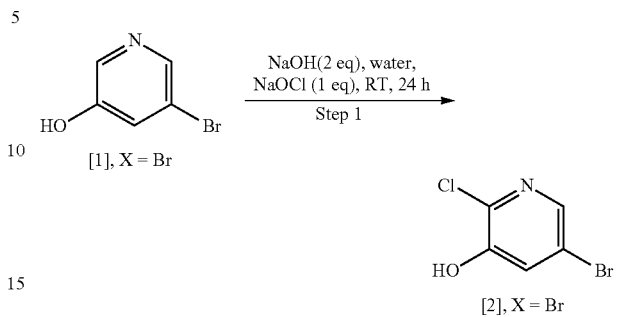

To a stirred solution of [1], X=Br (1 wt, 1 mol eq.) in water (1.2 vol.) was added NaOH (0.468 wt, 2 mol eq.) portionwise at room temperature. After a while, 11-13 wt % NaOCl aqueous solution (4.276 vol., 1.0 mol eq.) was added dropwise to the reaction mixture at room temperature, and the resulting reaction mixture was stirred for 24 h at the same temperature. The reaction was monitored by TLC and analyzed by LC-MS. The resultant reaction mixture was diluted with water (2 vol.), and then the cooled reaction crude mixture was gradually acidified with AcOH (~1.4 vol.) to produce the solid, which was filtered and collected. The solid cake was washed twice with water (2×0.25 vol.) to obtain 1.12 wt of crude solid product. To isolate pure product, the crude solid was recrystallized in MeOH:H$_2$O solvent mixture [60:40] (3.0 vol.) to produce desired 5-bromo-2-chloropyridin-3-ol [2], X=Br (pale yellow solid). $^1$H NMR [300 MHz, DMSO-d$_6$]: δ 8.05 (d, 1H, J=2.1 Hz), 7.49 (d, 1H, J=1.8 Hz).

Step 2: Synthesis of 5-bromo-2-chloro-3-(3-methoxypropoxy) pyridine [3], X=Br

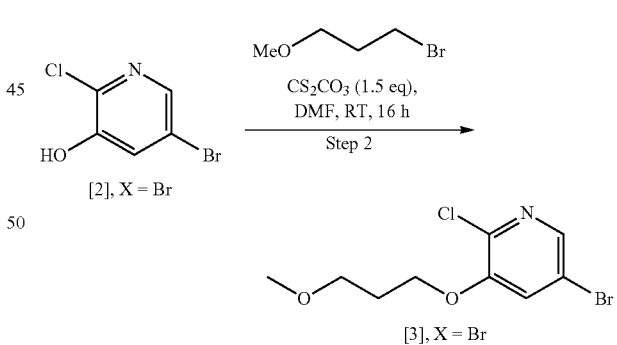

To a stirred solution of [2], X=Br (1 wt, 1 mol eq.) in DMF (5 vol.) was added portionwise Cs$_2$CO$_3$ (2.34 wt, 1.5 mol eq.) at room temperature, and then the reaction mixture was continued on stirring for 10 min. Then, 1-bromo-3-methoxy-propane (0.65 wt, 1.2 mol eq.) was added dropwise to the reaction mixture at room temperature and stirred for 16 h at the same temperature. The reaction was monitored by TLC. After completion of reaction, the resultant reaction mixture was diluted with water (3.2 vol.), and stirring was continued for 30 min to produce the solid, which was filtered, washed with water and dried under reduced pressure to obtain the product 5-bromo-2-chloro-3-(3-methoxypropoxy)pyridine

[3], X=Br as off-white solid. ¹H-NMR [300 MHz, DMSO-d$_6$]: δ 8.10 (d, 1H, J=1.5 Hz), 7.87 (d, 1H, J=1.5 Hz), 4.15 (t, 2H, J=6.0 Hz), 3.45 (t, 2H, J=6.4 Hz), 3.22 (s, 3H), 1.95 (quint, 2H, J=6.4, 12.4 Hz).

Step 3: Synthesis of
5-bromo-2-methoxy-3-(3-methoxypropoxy) pyridine
[4], X=Br

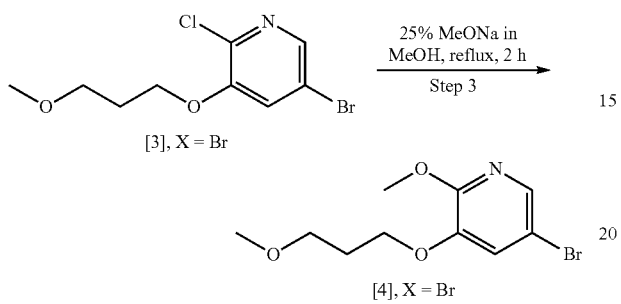

Procedure I: Compound [3], X=Br (1.0 wt, 1 mol eq.) was added to a solution of 25 w/v % sodium methoxide in methanol (7.68 vol., 10 mol eq.) at room temperature under inert atmosphere. The resulting reaction mixture was heated to reflux condition and maintained for 2 h. The reaction was monitored by LC-MS. After completion of reaction, the reaction was quenched with water (4.0 vol.). The resulting reaction mixture was concentrated under reduced pressure to yield reaction crude, which was extracted with EtOAc (3×10 vol.). The combined organic layers were dried over sodium sulphate, filtered, and concentrated under reduced pressure to get the crude residue, which was purified by silica-gel [60-120 mesh] column chromatography [1-2% of EtOAc in hexanes as a eluent] furnished target product 5-bromo-2-methoxy-3-(3-methoxypropoxy)pyridine [4], X=Br, as a light yellow liquid, which solidified on long standing. ¹H-NMR [300 MHz, DMSO-d$_6$]: δ 7.79 (d, 1H, J=2.1 Hz), 7.49 (d, 1H, J=1.8 Hz), 4.05 (t, 2H, J=6.3 Hz), 3.85 (s, 3H), 3.44 (t, 2H, J=6.3 Hz), 3.24 (s, 3H), 1.94 (quint, 2H, J=6.3, 12.6 Hz).

Procedure II: To a stirred solution of [3], X=Br (10 kg, 1.0 eq.) in toluene (55 L, 5.5 vol) was added 25% sodium methoxide in MeOH solution (25 L, 3.25 eq) at 25-30° C. After the addition, the reaction mixture was stirred for 16-20 h at 68-73° C. The reaction was monitored by LC-MS. After completion of the reaction, the reaction mixture was cooled to 30-35° C., and the reaction mass was poured into water (10 L) slowly at 35-40° C. and stirred for 30 min. The organic layer was separated and the aqueous layer was extracted with toluene (10 L). Toluene was evaporated under reduced pressure at <60° C. to get crude residue, which was co-distilled with ethyl acetate (5 L) to remove any traces of toluene. Further, the residue was diluted with ethyl acetate (20 L) and cooled to 40-45° C., and charcoal (1 kg) was added and stirred for 1 h at 40-45° C. The reaction mass was filtered through CELITE® bed and washed with ethyl acetate (5 L). The organic layer was evaporated under reduced pressure at <45° C. The reaction mass was dried until the solvent traces were removed (monitored by GC/¹H NMR). The resulting compound was further kept in trays at 10-20° C. for 4-8 h, yielding flake-type solid. The flakes were crushed and air dried for 4-5 h to afford 5-bromo-2-methoxy-3-(3-methoxypropoxy) pyridine [4], X=Br (7.3 kg, 75.0%) as a white crystalline solid.

Scheme 12 (see also Scheme 10).

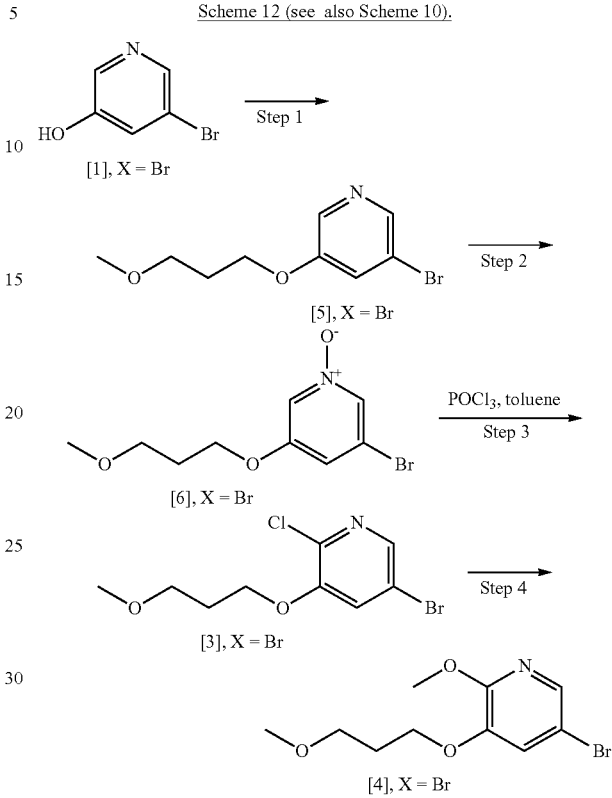

Step 1: Synthesis of
3-bromo-5-(3-methoxypropoxy)pyridine [5], X=Br

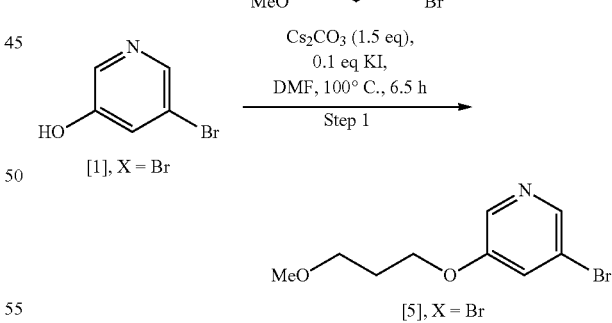

To a solution of 5-bromopyridin-3-ol [1], X=Br (40 g, 230 mmol) in DMF (400 mL) was added 1-bromo-3-methoxypropane (30.8 mL, 276 mmol), Cs$_2$CO$_3$ (112 g, 345 mmol), and KI (3.8 g 23 mmol). The reaction mixture was then heated to 100° C. for 6.5 hours. The reaction mixture was cooled to room temperature before diluting with EtOAc (400 mL). The organic layer was washed with water (3×250 mL), brine (200 mL), dried over MgSO$_4$ and concentrated under reduced pressure to give 3-bromo-5-(3-methoxypropoxy) pyridine [5], X=Br (39.9 g, 71% yield) as a brown oil. ¹H NMR (400 MHz, DMSO-$d_6$): 8.24 (m, 2H), 7.67 (m, 1H), 4.08 (t, 2H), 3.42 (t, 2H), 3.21 (s, 3H), 1.92 (p, 2H).

Step 2: Synthesis of 3-bromo-5-(3-methoxypropoxy)pyridine 1-oxide [6], X=Br

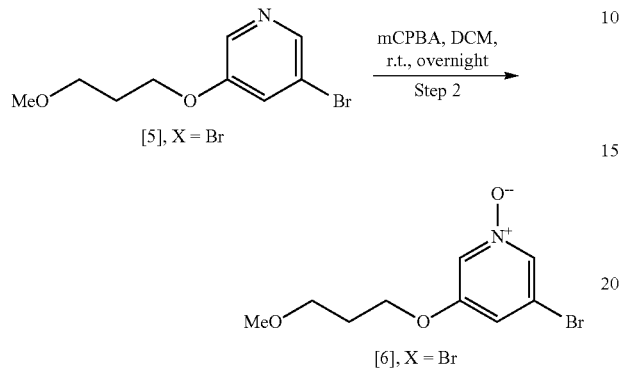

To a solution of 3-bromo-5-(3-methoxypropoxy)pyridine [5], X=Br (39.9 g, 162.1 mmol) in $CH_2Cl_2$ (400 mL) was added 3-chloroperoxybenzoic acid, 50-55%, cont. ca 10% 3-chlorobenzoic acid, balance water (101.7 g, 324.2 mmol). The mixture was stirred at room temperature overnight. The reaction mixture was partitioned between $CH_2Cl_2$ and saturated sodium hydrogen carbonate solution. The organics were then washed with $H_2O$ and brine and concentrated under reduced pressure to give 3-bromo-5-(3-methoxypropoxy)pyridine 1-oxide [6], X=Br (41.9 g, 99% yield) as a yellow oil that solidified upon standing. $^1$H NMR (300 MHz, $CDCl_3$): 7.97 (s, 1H), 7.87 (s, 1H), 7.02 (s, 1H), 4.04 (t, 2H), 3.49 (t, 2H), 3.33 (s, 3H), 2.02 (p, 2H).

Alternately oxidation of [5] to [6] can be performed with hydrogen peroxide/acetic acid.

Step 3: Synthesis of 5-bromo-2-chloro-3-(3-methoxypropoxy)pyridine [4], X=Br

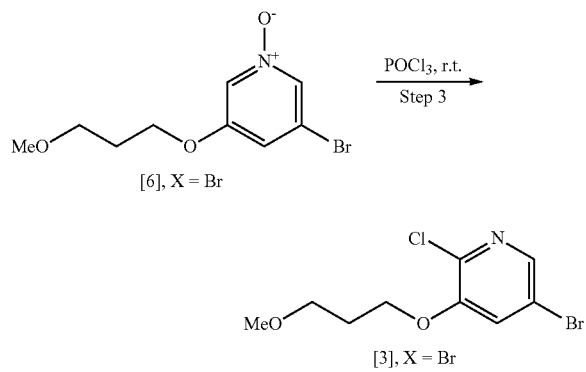

To 3-bromo-5-(3-methoxypropoxy)pyridine 1-oxide [6], X=Br (38 g, 145 mmol) was added $POCl_3$ (270 mL, 2.90 mol). The reaction mixture was then stirred at room temperature for 16 h. The excess $POCl_3$ was removed under reduced pressure at 60° C. The remaining residue was diluted with $CH_2Cl_2$ (100 mL) before quenching with saturated sodium hydrogen carbonate solution (200 mL), while maintaining the temperature at ~10° C. The layers were separated and the aqueous layer was extracted with $CH_2Cl_2$ (3×100 mL). The combined organic layers were washed with brine (150 mL), dried over $MgSO_4$, and concentrated under reduced pressure to give 5-bromo-2-chloro-3-(3-methoxypropoxy)pyridine [3], X=Br (36.6 g) as a crude orange solid. The residue was recrystallized from hot isopropanol (70 mL) to give 5-bromo-2-chloro-3-(3-methoxypropoxy)pyridine [3] (22.2 g, 55% [MH]$^-$=281.9. $^1$H NMR (400 MHz, $CDCl_3$): 8.04 (d, 1H), 7.35 (d, 1H), 4.10 (t, 2H), 3.59 (t, 2H), 3.35 (s, 3H), 2.11 (p, 2H).

Example 2: Synthesis of (R)-2-isopropyl-1-tosylaziridine [9]

Scheme 13.

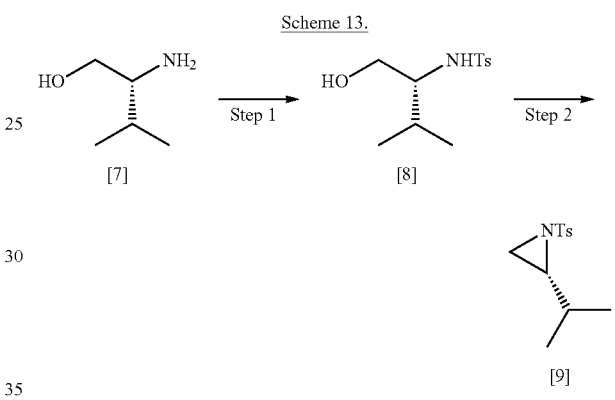

Step 1: Synthesis of (R)-N-(1-hydroxy-3-methylbutan-2-yl)-4-methylbenzenesulfonamide [8]

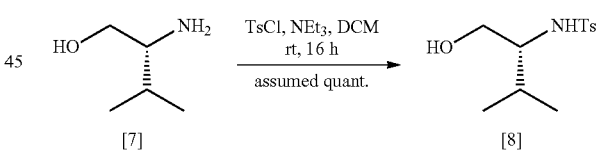

To a stirred solution of D-valinol [7] (150 g, 1.454 mol) in dichloromethane (3 L) cooled to 0° C. was added tosyl chloride (277 g, 1.454 mol), and the mixture was stirred for 10 min at 0° C. Triethylamine (365 mL, 2.617 mol) was added dropwise to the reaction mixture at 0° C. After complete addition, the reaction mixture was allowed to warm up to room temperature and stirred for 16 hours. The reaction mixture was quenched by addition of water (5 L). The layers were separated, and the aqueous layer was further extracted with dichloromethane (2×2.5 L). The combined organic layers were dried over sodium sulfate, filtered and concentrated under reduced pressure to give (R)-N-(1-hydroxy-3-methylbutan-2-yl)-4-methylbenzenesulfonamide [8] (390 g, assumed quantitative) as a pale yellow solid. [MH]+=258.1. $^1$H NMR (300 MHz, $CDCl_3$): 7.77 (d, 2H), 7.29 (d, 2H), 3.55 (m, 2H), 3.03 (brs, 1H), 2.42 (s, 3H), 1.77 (m, 1H), 0.79 (d, 6H).

Step 2: Synthesis of (R)-2-isopropyl-1-tosylaziridine [9]

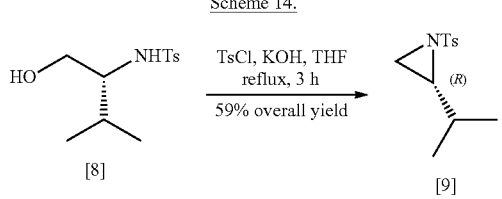

Scheme 14.

To a suspension of potassium hydroxide (128 g, 2.273 mol) in tetrahydrofuran (3 L) was added a solution of (R)-N-(1-hydroxy-3-methylbutan-2-yl)-4-methylbenzenesulfonamide [8] (195 g, 0.758 mol) in tetrahydrofuran (1 L), followed by tosyl chloride (159 g, 0.834 mol) in portions. The reaction mixture was then stirred under reflux for 3 hours, cooled to room temperature and diluted with water (4 L). The mixture was extracted with ethyl acetate (3×2 L). The combined organic layers were dried over sodium sulfate, filtered and concentrated under reduced pressure to give 353 g of a crude pale orange solid. The residue was dissolved in hot isopropyl alcohol (2.3 L). The solution was left to cooled down to room temperature over a period of 2 hours. The resulting solid was then collected by filtration, washed with cooled isopropyl alcohol (400 mL), and dried under reduced pressure to give (R)-2-isopropyl-1-tosylaziridine [9] (204 g, 59% over 2 steps) as a white solid. $^1$H NMR (300 MHz, CDCl$_3$): 7.82 (d, 2H), 7.32 (d, 2H), 2.60 (d, 1H), 2.49 (td, 1H), 2.43 (s, 3H), 2.09 (d, 1H), 1.40 (m, 1H), 0.89 (d, 3H), 0.78 (d, 3H).

Example 3: Synthesis of tert-butyl (S)-(1-(6-methoxy-5-(3-methoxypropoxy)pyridin-3-yl)-3-methylbutan-2-yl)carbamate [11], according to Schemes 5-8

Scheme 15 (see also Scheme 5).

Synthesis of tert-butyl (S)-(1-(6-methoxy-5-(3-methoxypropoxy)pyridin-3-yl)-3-methylbutan-2-yl) carbamate [11], according to Scheme 15

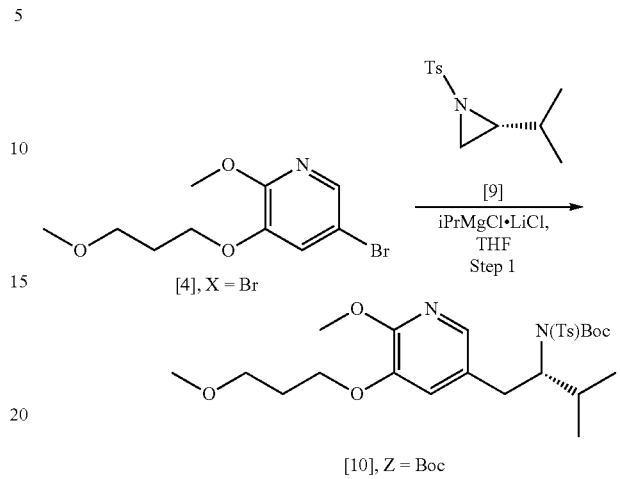

Step 1: To a stirred solution of 5-bromo-2-methoxy-3-(3-methoxypropoxy)pyridine [4], X=Br (20.0 g, 72.43 mmol) in THF (200 mL) was added i-PrMgCl.LiCl (67.0 mL, 1.2 eq, 1.3 M in THF). The contents were allowed to stir at 33° C. for 8 h. The reaction mixture was cooled to 30° C. 9 (13.0 g, 54.32 mmol), and CuI (1.38 g, 7.24 mmol) were then added under nitrogen atmosphere in order. Alternatively, 9 and CuI can be added as part of a solution or slurry. The mixture was stirred at 30° C. until completion as determined by UPLC in about 10 h. The reaction mixture was cooled to 20° C., charged with Boc anhydride (Boc$_2$O) (23.71, 108.64 mmol) and stirred at 25° C. until completion as determined by UPLC in about 2 h. Toluene (100 mL) was added, and the reaction was quenched by adding 10% NH$_4$Cl (200 mL) while maintaining the internal temperature below 25° C. The contents were stirred for 30 min and then the layers were allowed to separate. The organic layer was then washed with 10% NH$_4$Cl (100 mL) followed by water (100 mL). The organic layer was filtered through a pad of Celite. The organic layer was concentrated under reduced pressure to approximately 2-3 volumes solution of [10], Z=Boc, and used in the next step without further purification. Alternatively, CuBr.Me$_2$S or CuCN can be used as catalysts in place of CuI.

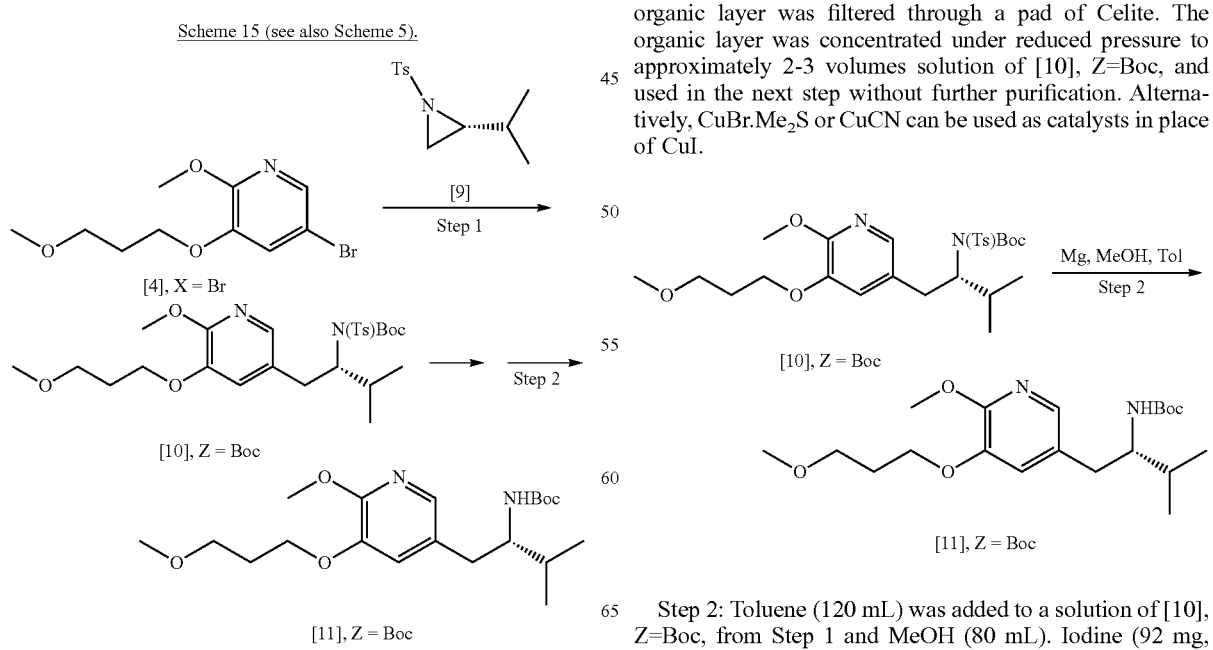

Step 2: Toluene (120 mL) was added to a solution of [10], Z=Boc, from Step 1 and MeOH (80 mL). Iodine (92 mg, 362.48 mmol) was added to the mixture followed by Mg turnings (1.76 g, 72.43 mmol). The contents were heated to 40° C. until the magnesium turnings were dissolved and then additional Mg turnings (3.5 g, 144.86 mmol) were added. The contents were heated at 40° C. until the reaction was deemed complete by UPLC (>95% conversion, 5 to 6 h). Additional Mg can be added if the reaction is not complete. The reaction mixture was cooled to 20° C. and was transferred slowly to another flask containing 50% aqueous citric acid (300 mL) with vigorous stirring. Additional 50% aqueous citric acid may be added to adjust to pH 5-6. Alternatively, 10% NH$_4$Cl/CELITE® mixture can be used in place of citric acid to quench the reaction. The contents were stirred for 30 min and filtered to remove solids. The layers were separated and the aqueous layer was back extracted with EtOAc (100 mL). The combined organic layer was washed with water (100 mL) and concentrated under reduced pressure to 2 volumes. n-Heptane (100 mL) was added and concentrated to 2 volumes. The mixture was cooled to room temperature, at which a slurry formed. The slurry was then cooled to 0° C. and aged for 4 h. The slurry was then filtered and rinsed into the flask with n-heptane (40 mL). The damp cake was dried under vacuum at 40° C. to give product [11], Z=Boc, as off-white solid (11.1 g, 55.5% yield). $^1$H NMR (400 MHz, CDCl$_3$) δ 7.49 (s, 1H), 6.97 (s, 1H), 4.32 (d, J=9.8 Hz, 1H), 4.09 (t, J=6.5 Hz, 2H), 3.97 (s, 3H), 3.68 (m, 1H), 3.56 (t, J=6.1 Hz, 2H), 3.35 (s, 3H), 2.70 (dd, J=14.2, 6.1 Hz, 1H), 2.56 (dd, J=14.2, 8.3 Hz, 1H), 2.11 (p, J=6.3 Hz, 2H), 1.79-1.66 (m, 1H), 1.36 (s, 9H),), 0.96 (d, J=6.8 Hz, 3H), 0.91 (d, J=6.8 Hz, 3H).

Scheme 16 (see also Scheme 6).

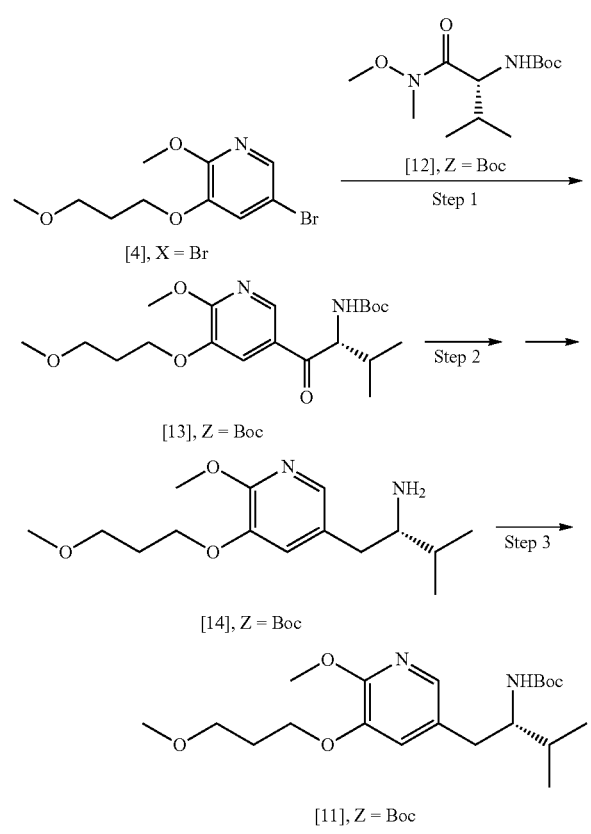

Synthesis of tert-butyl (S)-(1-(6-methoxy-5-(3-methoxypropoxy)pyridin-3-yl)-3-methylbutan-2-yl) carbamate [11], according to Scheme 16

Tert-butyl N-[(2R)-1-[6-methoxy-5-(3-methoxypropoxy)pyridin-3-yl]-3-methyl-1-oxobutan-2-yl] carbamate [13], Z=Boc

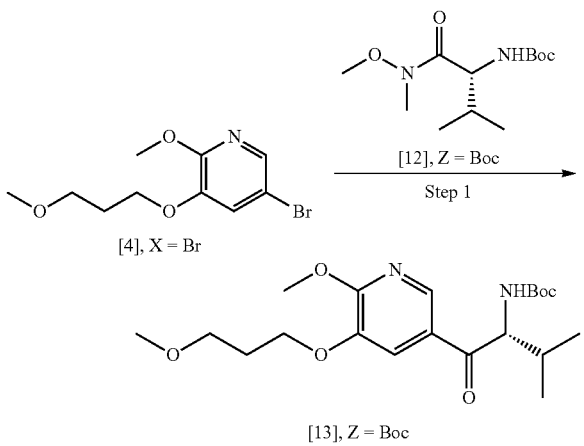

Step 1: To a first flask containing a solution of 5-bromo-2-methoxy-3-(3-methoxypropoxy)pyridine [4], X=Br (20.70 g, 74.95 mmol) in THF (80 mL), i-PrMgCl.LiCl (66.53 mL, 12.56 g, 86.49 mmol) was added over 10 min and the mixture was stirred for 8 h. In a second flask, to a solution of tert-butyl N-[(1R)-1-[methoxy(methyl)carbamoyl]-2-methylpropyl]carbamate [12], Z=Boc (15.01 g, 57.66 mmol) in THF (60 mL), i-PrMgCl (28.83 mL, 5.93 g, 57.66 mmol) was added over 60 min with intermittent external cooling, and the mixture was stirred for 15 min. The solution in the second flask was transferred to the solution in the first flask, and the mixture was allowed to stir at 20° C. for 18 h. LCMS indicated >80% desired product with some remaining starting materials. The reaction mixture was cooled to 0° C., and 3N HCl (~50 mL) was slowly added, keeping the internal temperature <3° C., until the mixture reached ~pH 4-5. 30 mL water and 60 mL n-heptane were then added. The mixture was warmed to ambient temperature with stirring over ~20 min. The aqueous and organic layer were then separated. The organic layer was washed with 80 mL water. The organic layer was then evaporated to a reduced volume until the desired material precipitated out of solution. The material was then redissolved by adding 40 mL heptane, 120 mL MTBE and heating at 50° C. The solution was allowed to cool to 40° C., slowly evaporated, and then cooled in an ice bath while stirred with a stir bar. The product then crystallized out of solution. The product was filtered, washed with n-heptane 100 mL, and dried to give product [13], Z=Boc, as a white solid (17.2 g, 73.5%). $^1$H NMR (400 MHz, CDCl$_3$) δ 8.42 (s, 1H), 7.60 (d, J=2.0 Hz, 1H), 5.39 (d, J=8.9 Hz, 1H), 5.12 (dd, J=9.0, 4.2 Hz, 1H), 4.16 (t, J=6.5 Hz, 2H), 4.08 (s, 3H), 3.56 (t, J=6.0 Hz, 2H), 3.36 (s, 3H), 2.13 (m, 3H), 1.45 (s, 9H), 1.04 (d, J=6.8 Hz, 3H), 0.78 (d, J=6.8 Hz, 3H).

Tert-butyl (S)-(1-(6-methoxy-5-(3-methoxypropoxy)pyridin-3-yl)-3-methylbutan-2-yl)carbamate [11], Z=Boc

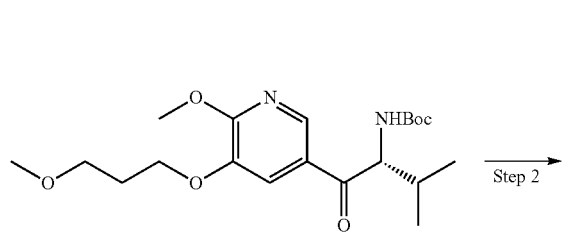

[13], Z = Boc

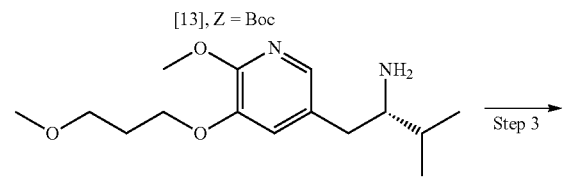

[14]

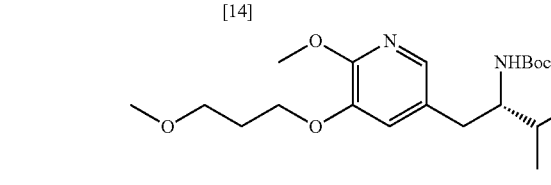

[11], Z = Boc

Step 2: Tert-butyl (R)-(1-(6-methoxy-5-(3-methoxypropoxy)pyridin-3-yl)-3-methyl-1-oxobutan-2-yl)carbamate [13], Z=Boc (800 mg, 2.02 mmol) and Ga(OTf)$_3$ (1033 mg, 2.02 mmol) were dissolved in DCE (10 ml) followed by addition of chlorodimethylsilane (576 mg, 6 mmol). The reaction was sealed and stirred at 80° C. for 6 hours. The reaction was quenched by adding saturated aqueous NaHCO$_3$ (until pH=8-9). The aqueous layer was extracted with DCM (3×10 mL). The organic layers were combined, dried over Na$_2$SO$_4$, and concentrated under vacuum to give crude (S)-1-(6-methoxy-5-(3-methoxypropoxy)pyridin-3-yl)-3-methylbutan-2-amine [14] which was used as-is in Step 3.

Step 3: Crude [14] (crude product from step 2), Boc$_2$O (654 mg, 3 mmol) and Et$_3$N (303 mg, 3 mmol), DMAP (25 mg) were dissolved in DCM (10 mL). The reaction was stirred at room temperature overnight. The reaction was quenched by addition of water (5 mL). The reaction was washed with water (5 mL), brine (5 mL) and dried over Na$_2$SO$_4$. The organic phase was concentrated under vacuum to give crude product which was purified via silica gel chromatography (0-5% MeOH/DCM) to yield tert-butyl (S)-(1-(6-methoxy-5-(3-methoxypropoxy)pyridin-3-yl)-3-methylbutan-2-yl)carbamate [11], Z=Boc (195 mg, 25% two steps).

Scheme 17 (see also Scheme 7).

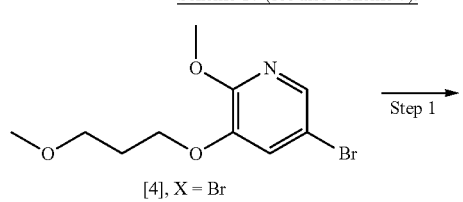

[4], X = Br

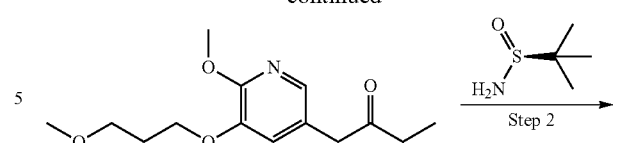

[15]

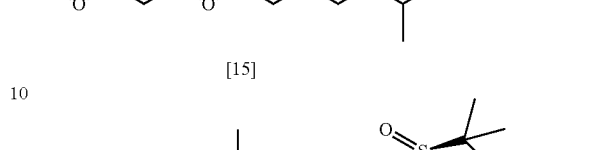

[16]

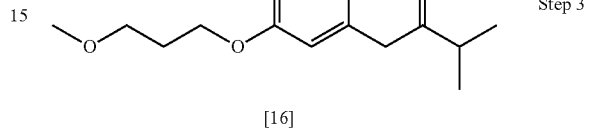

[17]

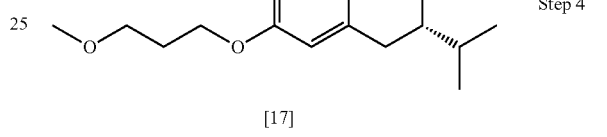

[14]·HCl

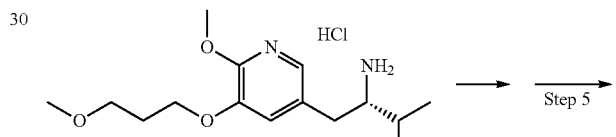

[11], Z = Boc

Scheme 18 (see also Scheme 8).

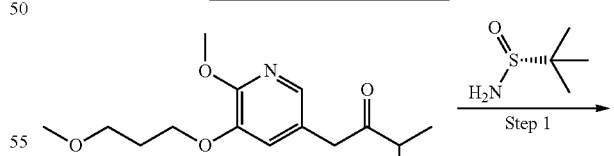

[15]

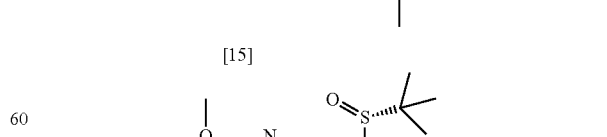

[18]

-continued

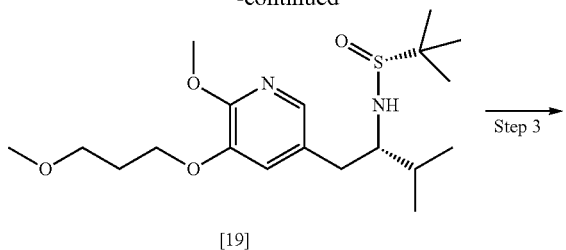

Synthesis of tert-butyl (S)-(1-(6-methoxy-5-(3-methoxypropoxy)pyridin-3-yl)-3-methylbutan-2-yl) carbamate [11], according to Schemes 17-18

1-(6-Methoxy-5-(3-methoxypropoxy)pyridin-3-yl)-3-methylbutan-2-one [15]

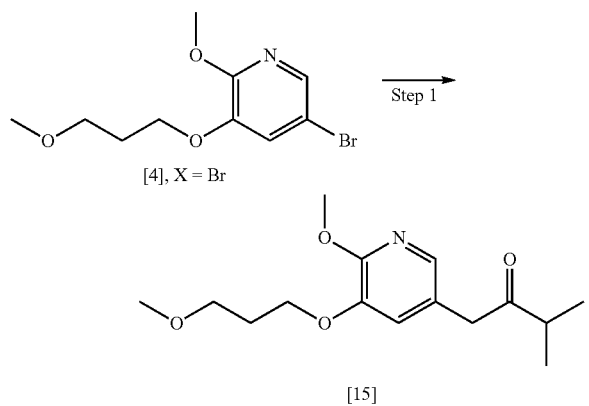

To a 1-L jacketed reactor equipped with an overhead stirrer, thermocouple, vacuum and nitrogen inlet and condenser was charged 2-methyltetrahydrofuran (MeTHF) (680 mL), 5-Bromo-2-methoxy-3-(3-methoxypropoxy)pyridine [4], X=Br (68.0 g; 246 mmol), and 3-methylbutan-2-one (80.2 mL; 750 mmol) followed by sodium tert-butoxide (78.2 g; 814 mmol) at room temperature. The sodium tert-butoxide did not completely dissolve at room temperature. The reaction mixture was degassed three times alternating between vacuum and nitrogen at room temperature (foaming observed during vacuum). Xantphos (3.06 g; 5.29 mmol) was added to the reaction followed by Pd$_2$(dba)$_3$ (2.24 g; 2.45 mmol) at room temperature. The reaction was heated to 80° C. under nitrogen for 2 hours (color change observed when heated). The reaction was monitored by LCMS. The reaction mixture was cooled to room temperature and DI water (350 mL) was slowly added, exotherm observed and the reaction was cooled to maintain temperature between 20-30° C. The reaction was stirred 15 min, agitation stopped and the phases were split (thick rag layer observed). The aqueous was back extracted with 2-methyltetrahydrofuran (MeTHF) (350 mL). The organic layers were combined, treated with activated carbon and filtered through a plug of silica gel and Celite to remove solids. The filtrate was concentrated under vacuum at 30-40° C. to a dark brown oil of [15] (67.4 g; 97.3% yield of crude product).

(S)-N-(1-(6-methoxy-5-(3-methoxypropoxy)pyridin-3-yl)-3-methylbutan-2-ylidene)-2-methylpropane-2-sulfinamide [16]

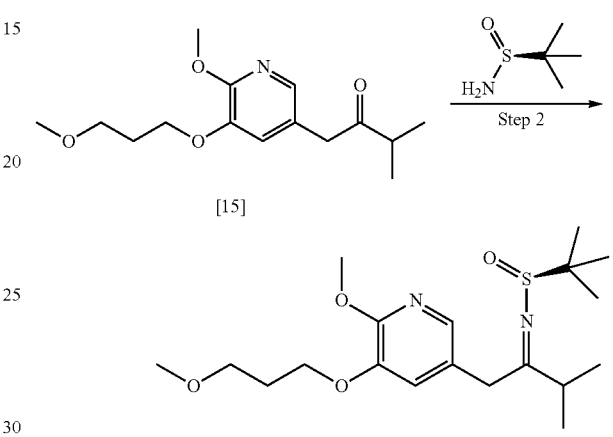

1-[6-methoxy-5-(3-methoxypropoxy)pyridin-3-yl]-3-methylbutan-2-one [15] (1.00 g, 3.55 mmol) and (S)-2-methylpropane-2-sulfinamide (0.65 g, 5.33 mmol) were dissolved in anhydrous THF (20 mL) in a 100 ml sealed tube. Tetraethoxytitanium (2.03 g, 8.89 mmol) was added, and the vessel was flushed with nitrogen gas, then sealed and heated to 80° C. for 18 h. After cooling to room temperature, the reaction mixture was added to water and the resulting solution was filtered through CELITE®. The filtrate was extracted with EtOAc (3×50 ml), and the combined organics was washed with brine, dried (sodium sulfate), filtered, and concentrated. Crude product was purified by silica gel column, eluting with 5-50% EtOAc gradient in hexane to afford (S)-N-{1-[6-methoxy-5-(3-methoxypropoxy)pyridin-3-yl]-3-methylbutan-2-ylidene}-2-methylpropane-2-sulfinamide [16] (1.07 g, 78.3%) as a yellow oil. MS obsd. (ESI$^+$) [(M+H)$^+$]: 385.4

(S)-N-((S)-1-(6-methoxy-5-(3-methoxypropoxy) pyridin-3-yl)-3-methylbutan-2-yl)-2-methylpropane-2-sulfinamide [17]

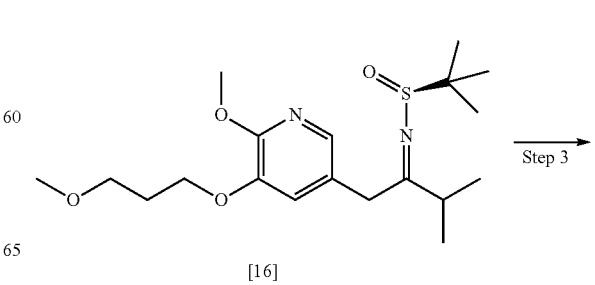

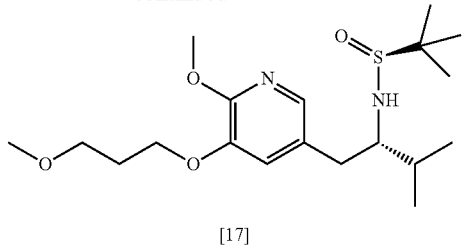

[17]

(S)-N-{1-[6-methoxy-5-(3-methoxypropoxy)pyridin-3-yl]-3-methylbutan-2-ylidene}-2-methylpropane-2-sulfinamide [16] (200.00 mg, 0.52 mmol) was dissolved in 3 ml anhydrous THF, and the mixture was cooled to −78° C. under nitrogen atmosphere. DIBAL-H (1560.31 μL, 1.56 mmol) (1.0 M solution in THF) was added dropwise over 3 minutes, and the resulting solution was stirred at −78° C. for 3 hours. Subsequently, the reaction was quenched at −78° C. by addition of brine solution (3 ml). After the solution was warmed to room temperature, the solution was further diluted with 10 ml water and extracted with EtOAc (2×20 ml). The combined organic phase was washed with brine (2×20 ml), dried over $Na_2SO_4$, then filtered and concentrated. Crude product was purified by silica gel column, eluting with 15-100% EtOAc gradient in hexane to afford (S)-N-[(2S)-1-[6-methoxy-5-(3-methoxypropoxy)pyridin-3-yl]-3-methylbutan-2-yl]-2-methylpropane-2-sulfinamide [17] (143.00 mg, 71.1%) as a clear oil, which solidified upon standing. $^1$H NMR (400 MHz, $CDCl_3$) δ 7.50 (d, J=1.9 Hz, 1H), 6.94 (d, J=2.0 Hz, 1H), 4.12-4.03 (m, 2H), 3.97 (d, J=0.4 Hz, 3H), 3.56 (t, J=6.0 Hz, 2H), 3.36 (d, J=0.4 Hz, 4H), 3.14 (d, J=7.0 Hz, 1H), 2.73 (dd, J=14.2, 5.5 Hz, 1H), 2.59 (dd, J=14.2, 8.8 Hz, 1H), 2.11 (p, J=6.3 Hz, 2H), 1.98 (qd, J=6.9, 4.0 Hz, 1H), 1.07 (d, J=0.5 Hz, 9H), 1.01 (dd, J=11.8, 6.9 Hz, 6H). MS obsd. (ESI$^+$) [(M+H)$^+$]: 387.4

(2S)-1-[6-methoxy-5-(3-methoxypropoxy)pyridin-3-yl]-3-methylbutan-2-amine hydrochloride [14.HCl]

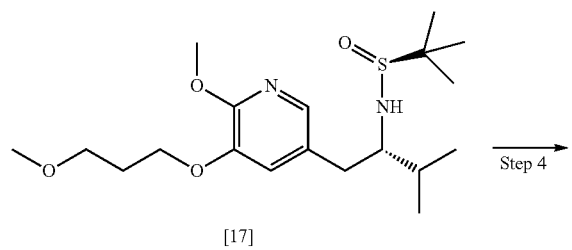

[17]

[14]

(S)-N-1[(2S)-1-[6-methoxy-5-(3-methoxypropoxy)pyridin-3-yl]-3-methylbutan-2-yl]-2-methylpropane-2-sulfinamide [17] (2.04 g, 5.28 mmol) was dissolved in 30 ml anhydrous DCM and hydrogen chloride solution (5277.45 μL, 0.77 g, 21.11 mmol) (4M in dioxane) was added. The reaction mixture was stirred at room temperature for 1 hour, then the solvent was evaporated. The crude solid was suspended in 30 ml EtOAc and the resulting slurry was filtered, washed with 2×20 ml EtOAc, then dried to afford (2S)-1-[6-methoxy-5-(3-methoxypropoxy) pyridin-3-yl]-3-methylbutan-2-amine hydrochloride [14].HCl (1.60 g, 95.1%) as a white solid. $^1$H NMR (400 MHz, DMSO-d$_6$) δ 7.89 (s, 2H), 7.57 (d, J=1.9 Hz, 1H), 7.28 (d, J=1.9 Hz, 1H), 4.01 (t, J=6.5 Hz, 2H), 3.82 (s, 3H), 3.45 (t, J=6.2 Hz, 2H), 3.23 (s, 4H), 2.78 (dd, J=14.4, 5.5 Hz, 1H), 2.68 (dd, J=14.3, 8.4 Hz, 1H), 2.00-1.80 (m, 3H), 0.96 (dd, J=10.2, 6.9 Hz, 6H). MS obsd. (ESI$^+$) [(M+H)$^+$]: 283.4

(R)-N-(1-(6-methoxy-5-(3-methoxypropoxy)pyridin-3-yl)-3-methylbutan-2-ylidene)-2-methylpropane-2-sulfinamide [18]

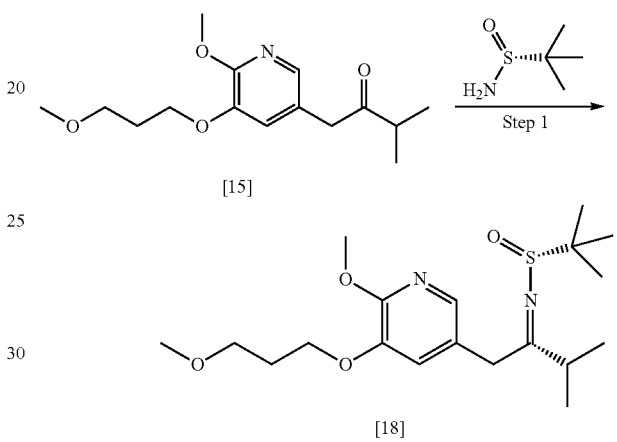

[15]

[18]

1-[6-methoxy-5-(3-methoxypropoxy)pyridin-3-yl]-3-methylbutan-2-one [15] (1.00 g, 3.55 mmol) and (R)-2-methylpropane-2-sulfinamide (0.65 g, 5.33 mmol) were dissolved in anhydrous THF (20 mL) in a 100 ml sealed tube. Tetraethoxytitanium (2.03 g, 8.89 mmol) was added, and the vessel was flushed with nitrogen gas, then sealed and heated to 80° C. for 18 h. After cooling to room temperature, the reaction was added to water and the resulting solution was filtered through CELITE®. The filtrate was extracted with EtOAc (3×50 ml) and the combined organics were washed with brine, dried (sodium sulfate), filtered, and concentrated. Crude product was purified by silica gel column, eluting with 5-50% EtOAc gradient in hexane to afford (R)-N-{1-[6-methoxy-5-(3-methoxypropoxy)pyridin-3-yl]-3-methylbutan-2-ylidene}-2-methylpropane-2-sulfinamide [18] (0.93 g, 68.3%) as a yellow oil. MS obsd. (ESI$^+$) [(M+H)$^+$]: 385.4

(R)-N-((S)-1-(6-methoxy-5-(3-methoxypropoxy) pyridin-3-yl)-3-methylbutan-2-yl)-2-methylpropane-2-sulfinamide [19]

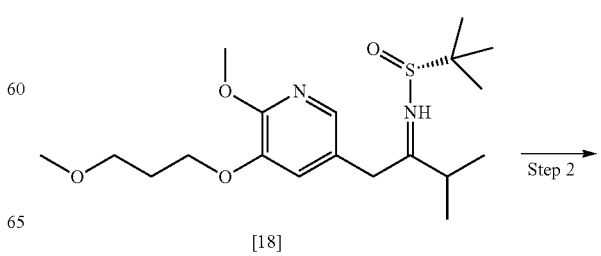

[18]

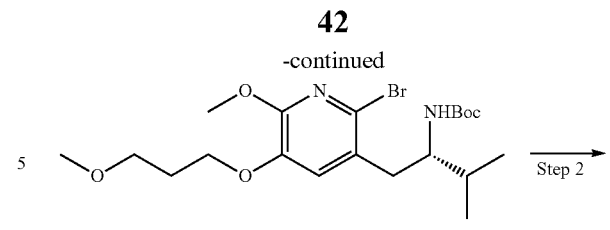

[20], X = Br, Z = Boc

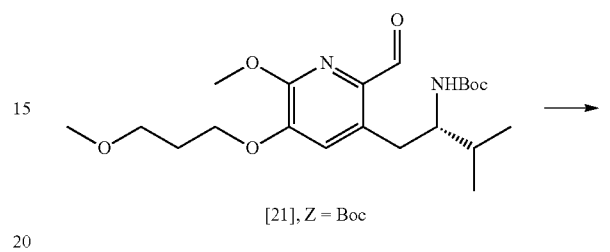

[21], Z = Boc

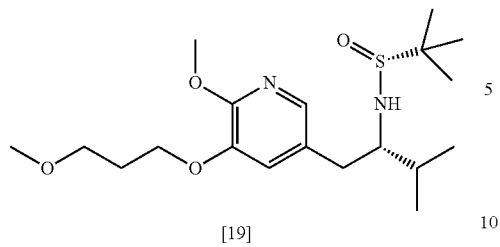

[19]

Conversion of [18] to [19] is performed using the same general procedure outlined for the transformation of [16] to [17], but using L-selectride.

Synthesis of tert-butyl (S)-(1-(6-methoxy-5-(3-methoxypropoxy)pyridin-3-yl)-3-methylbutan-2-yl) carbamate [11]

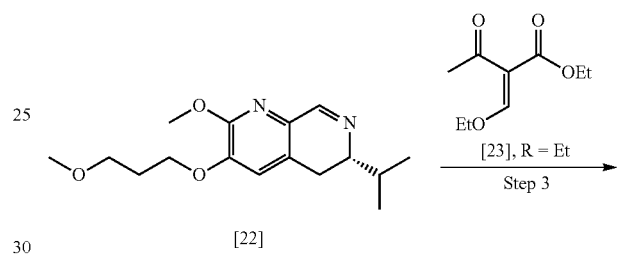

[22]

[23], R = Et
Step 3

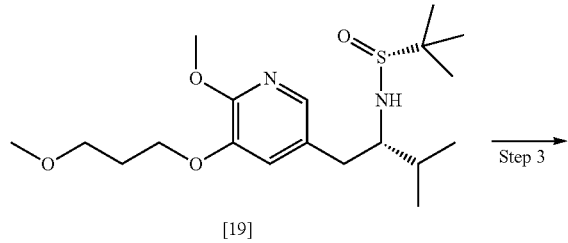

[19]

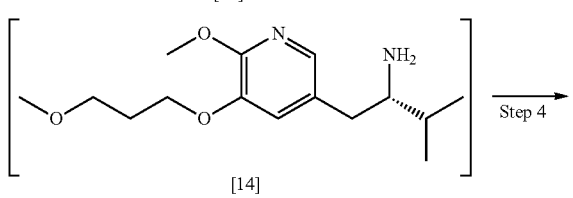

[14]

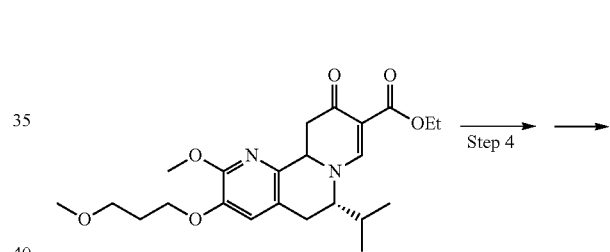

[24], R = Et

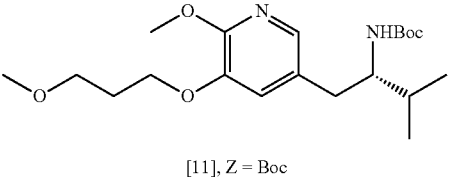

[11], Z = Boc

This conversion can be accomplished with procedures described elsewhere herein.

Example 4: Synthesis of (S)-6-isopropyl-2-methoxy-3-(3-methoxypropoxy)-10-oxo-5,10-dihydro-6H-pyrido[1,2-h] [1,7]naphthyridine-9-carboxylic acid [26], according to Schemes 2 and 4

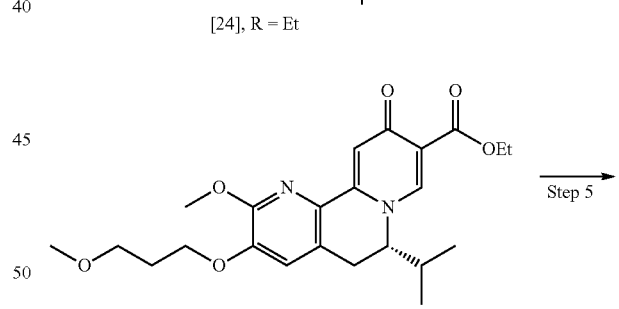

[25], R = Et

Scheme 19.

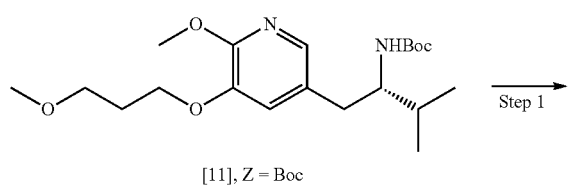

[11], Z = Boc

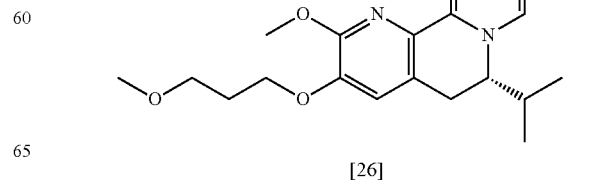

[26]

Synthesis of tert-butyl (S)-(1-(2-bromo-6-methoxy-5-(3-methoxypropoxy)pyridin-3-yl)-3-methylbutan-2-yl)carbamate [20], X=Br, Z=Boc

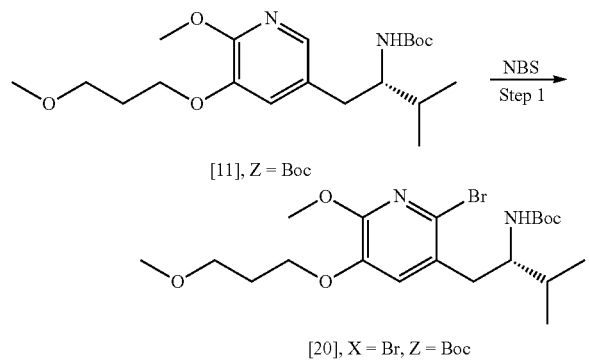

Step 1: A flask was charged with [11], Z=Boc (5.67 g, 14.8 mmol) and N-bromosuccinimide (NBS) (2.9 g, 16.2 mmol). Dichloromethane (180 mL) was then added to the mixture, and the mixture was allowed to stir at 25° C. until reaction completion as determined by UPLC (2 to 3 h). The reaction mixture was washed with 9.3% aqueous NaHCO₃ two times (40 mL each). The organic layer was washed with water (40 mL). The organic layer concentrated to ~2 volumes and then charged with cyclopentyl methyl ether (CPME) (60 mL). The mixture was concentrated under reduced pressure to ~5 volumes, and a slurry was formed. The slurry was stirred at 20° C. for 1 h and filtered. The flask was rinsed with CPME (2×15 mL). The solids were dried in vacuum to give product [20], X=Br, Z=Boc (5.5 g, 91% yield) as a white solid. Alternatively, bromination of [11] to yield [20] can be carried out using Br₂/AcOH or pyridiniumtribromide/DMF under appropriate conditions. ¹H NMR (400 MHz, chloroform-d) δ 7.02 (s, 1H), 4.43 (d, J=10.1 Hz, 1H), 4.08 (t, J=6.5 Hz, 2H), 3.96 (s, 3H), 3.76 (m, 1H), 3.54 (td, J=6.2, 1.4 Hz, 2H), 3.34 (s, 3H), 2.82 (dd, J=14.6, 4.5 Hz, 1H), 2.63 (dd, J=14.5, 10.5 Hz, 1H), 2.09 (p, J=6.3 Hz, 2H), 1.81 (m, 1H), 1.32 (s, 9H), 0.98 (dd, J=6.8, 5.1 Hz, 6H).

Synthesis of (S)-6-isopropyl-2-methoxy-3-(3-methoxypropoxy)-5,6-dihydro-1,7-naphthyridine [22]

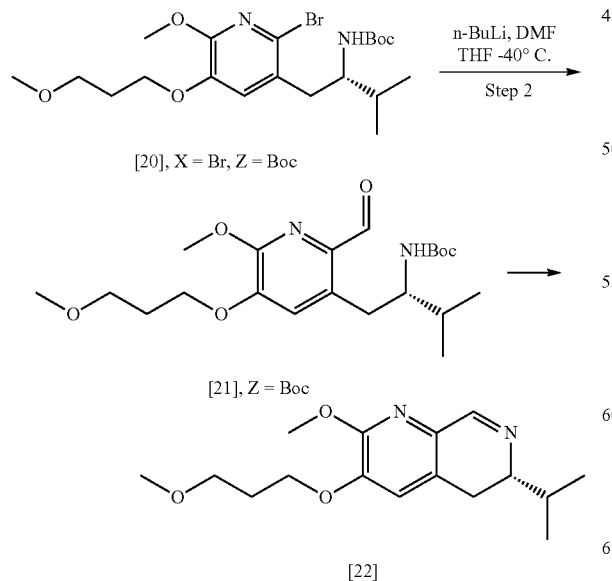

Step 2: In a dry round bottom flask, [20], X=Br, Z=Boc (2.50 g, 5.42 mmol) was added followed by anhydrous THF (65 mL) under nitrogen gas. The contents were heated (40 to 50° C.) to give a clear solution. The solution was cooled to −40° C. (internal). A 1.6M solution of n-BuLi in n-hexane (7.45 mL, 11.92 mmol, 1.6 M solution) was then added while maintaining the internal temperature below −35° C., with caution being taken due to the exothermic reaction. The mixture was stirred at −40° C. for 30 min, and then a solution of DMF (0.50 mL, 0.48 g, 6.50 mmol) in THF (15 mL) was added while maintaining the internal temperature below −35° C. The mixture was stirred at −40° C. temperature for 30 min. LCMS indicated formation of [21], Z=Boc. The mixture was allowed to warm to 25° C. and stirred for 18 h. LCMS indicated formation of [22]. EtOAc (2.5 mL) was then added and the mixture was evaporated to about 10 mL. Additional EtOAc (25 mL) was added and the mixture was washed with aq. 1N HCl solution (3×15 mL). The combined aqueous layers were neutralized by adding NaHCO₃ solid slowly with stirring until pH 7 to 8. The aqueous phase was extracted with DCM (3×15 mL). The combined DCM layer was dried over Na₂SO₄ and concentrated to give [22] as clear yellow oil (830 mg, 52.0% yield). Alternatively, conversion of [20] to [22] can be performed using other alkyl lithium and/or Grignard reagents, such as, but not limited to a mixture of n-BuLi/i-PrMgCl. ¹H NMR (400 MHz, chloroform-d) δ 8.27 (s, 1H), 6.87 (s, 1H), 4.13 (t, J=6.5 Hz, 2H), 4.01 (s, 3H), 3.56 (t, J=6.0 Hz, 2H), 3.35 (s, 3H), 3.34-3.25 (m, 1H), 2.65-2.57 (m, 2H), 2.18-1.98 (m, 2H),), 1.08 (d, J=6.7 Hz, 3H), 1.05 (d, J=6.7 Hz, 3H).

Synthesis of ethyl (S)-6-isopropyl-2-methoxy-3-(3-methoxypropoxy)-10-oxo-5,10-dihydro-6H-pyrido[1,2-h][1,7]naphthyridine-9-carboxylate [25], R=Et

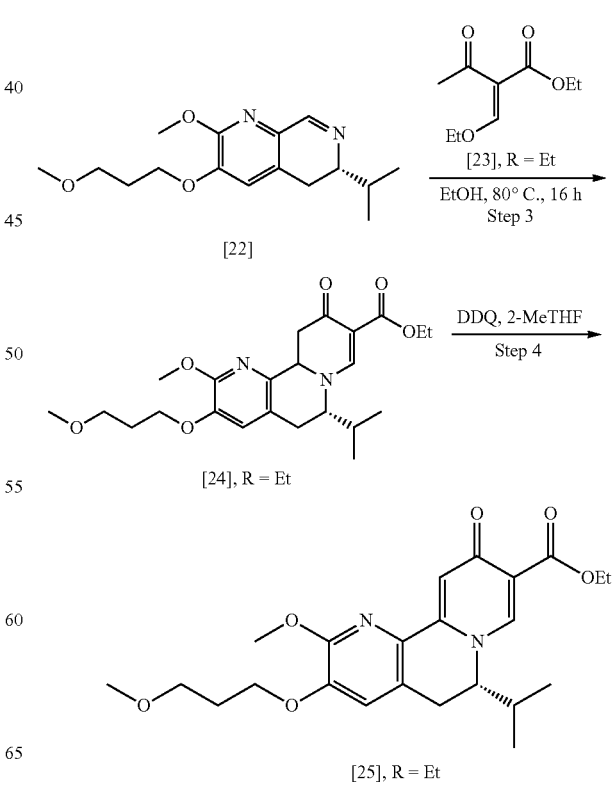

Step 3: [22] (52.40 g, 125.45 mmol) was dissolved in absolute ethanol (850 mL, 16 Vol). Ethyl 2-(ethoxymethylidene)-3-oxobutanoate [23] (70.78 g, 380.11 mmol) was added and the mixture was heated at 80° C. for 36 h. The reaction become dark brown. The reaction was deemed complete. The solvent was evaporated to ~0.5 to 1 Vol, 2-MeTHF was added and solvent swapped twice (2×100 mL). The 2-Me THF solution was taken to the next step. The purity of the [24] mixture was estimated to be ~35%. Alternatively, conversion of [22] to [24] can be performed using water or 50% aqueous ethanol solution in place of absolute ethanol.

Step 4: The solution of [24], R=Et, in 2-MeTHF was diluted with additional 2-MeTHF (400 mL, 8 Vol). 2,3-Dichloro-5,6-dicyano-1,4-benzoquinone (DDQ) (31.7 g, 139.6 mmol) was added and the mixture was stirred at ambient temperature (~22-25° C.) for 20 h. The reaction mixture was washed with 1N HCl (3×200 mL). The acidic aqueous washings were basified with NaHCO$_3$ to pH 7-8 and extracted with EtOAc (3×200 mL). The EtOAc layer was washed with 10% sodium bisulfate (200 mL) and saturated Na$_2$CO$_3$ (200 mL), dried over Na$_2$SO$_4$ and evaporated to minimum volume. The residue was triturated with MTBE to obtain product [25], R=Et, as light brown solid (18.25 g, 24.5%). $^1$HNMR (400 MHz, CDCl$_3$) δ 8.15 (s, 1H), 7.42 (s, 1H), 6.87 (s, 1H), 4.39 (qd, J=7.1, 2.1 Hz, 2H), 4.22-4.08 (m, 2H), 4.04 (s, 3H), 3.75 (dd, J=9.5, 4.8 Hz, 1H), 3.57 (td, J=6.1, 1.7 Hz, 2H), 3.36 (s, 3H), 3.39-3.29 (m, 1H), 3.00 (dd, J=16.4, 1.6 Hz, 1H), 2.13 (p, J=6.2 Hz, 2H), 1.98-1.84 (m, 1H), 1.39 (t, J=7.1 Hz, 3H), 0.95 (d, J=6.7 Hz, 3H), 0.83 (d, J=6.7 Hz, 3H). Alternatively conversion of [24] to [25], R=Et, can be performed with p-chloranil, NBS, and air.

Synthesis of (S)-6-isopropyl-2-methoxy-3-(3-methoxypropoxy)-10-oxo-5,10-dihydro-6H-pyrido[1,2-h][1,7]naphthyridine-9-carboxylic acid [26]

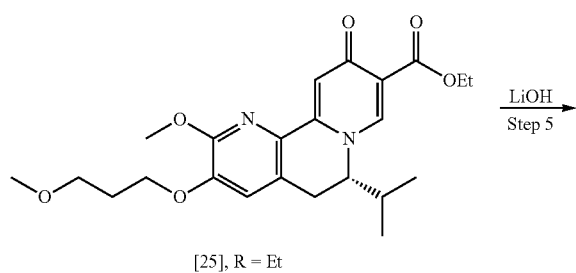

[25], R = Et

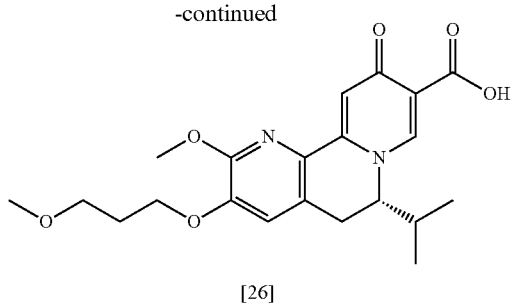

[26]

Step 5: [25], R=Et (15.40 g, 35.77 mmol) was added to a 500 mL RBF. MeOH (70 mL, 4.5 Vol) was added and the mixture allowed to stir to obtain a clear solution. A solution of LiOH.H$_2$O (3.00 g, 71.54 mmol) in H$_2$O (23 mL, 1.5 Vol) was added to the methanolic solution slowly over 1 h keeping the temperature 25-30° C. After the addition was complete, the reaction mixture was allowed to stir for an additional 2 h, at which point the reaction was deemed complete by LCMS. Methanol was evaporated. H$_2$O (70 mL) and ethyl acetate (175 mL) were added. 4N HCl was added with stirring to adjust the pH to ~5-6. The ethyl acetate layer was separated, and the aqueous layer was washed with additional 50 mL ethyl acetate. The ethyl acetate layers were pooled, washed with H$_2$O (75 mL), and evaporated to ~2-3 Vol. Absolute ethanol (70 mL) was added and the mixture evaporated to solvent swap to ~2-3 Vol. Ethanol (70 mL) was again added and evaporated to ~2-3 Vol. Ethanol (70 mL) was again added and evaporated to 5-6 Vol and transferred to a 250 mL jacketed reactor. The suspension was heated at 80° C. for about 60 min to obtain a clear solution. The solution was ramp-cooled over 12 h to 15° C. The suspension was stirred at 15° C. for 4 h and then at 0° C. for 1 h. The suspension was filtered and washed with ~20 mL of cold ethanol. The solids were dried at 40° C. in a vacuum oven for 20 h to give 12.5 g, 80% of [26] as beige colored crystalline solid (>99% purity, >99% chiral purity). $^1$H NMR (400 MHz, DMSO-d$_6$) δ 8.81 (s, 1H), 7.42 (s, 1H), 7.36 (s, 1H), 4.67-4.34 (m, 1H), 4.11 (m, 2H), 3.95 (s, 3H), 3.45 (t, J=6.2 Hz, 2H), 3.36 (dd, J=16.8, 5.7 Hz, 1H), 3.23 (s, 3H), 3.19 (d, J=16.5 Hz, 1H), 1.98 (p, J=6.4 Hz, 2H), 1.85-1.62 (m, 1H), 0.87 (d, J=6.6 Hz, 3H), 0.68 (d, J=6.7 Hz, 3H).

Example 5: Synthesis of (S)-6-isopropyl-2-methoxy-3-(3-methoxypropoxy)-10-oxo-5,10-dihydro-6H-pyrido[1,2-h] [1,7]naphthyridine-9-carboxylic acid [26], according to Scheme 3

Scheme 20.

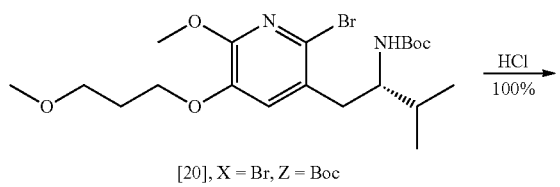

[20], X = Br, Z = Boc

-continued

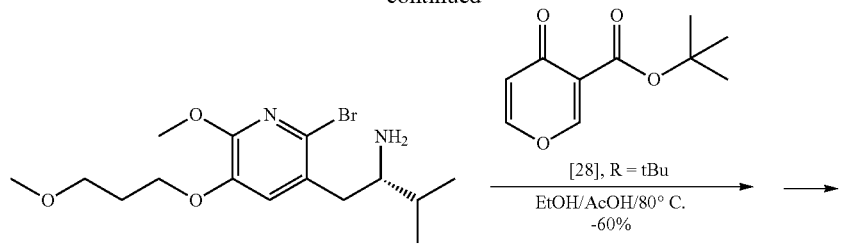

[27], X = Br

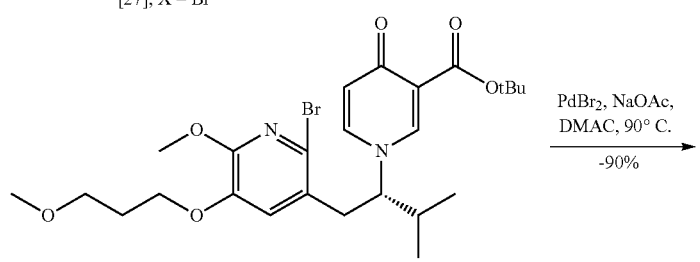

[29], X = Br, R = tBu

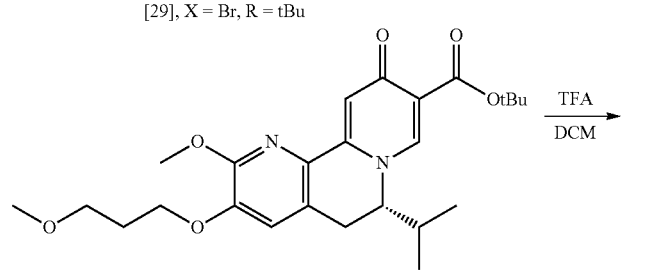

[25], R = tBu

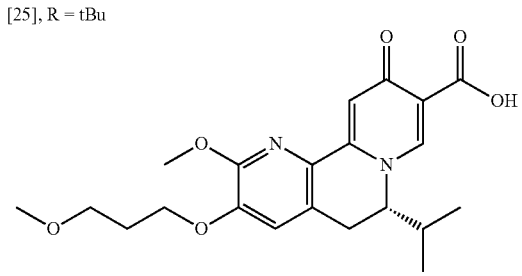

[26]

Synthesis of tert-butyl (S)-(1-(2-bromo-6-methoxy-5-(3-methoxypropoxy)pyridin-3-yl)-3-methylbutan-2-yl)carbamate [20], X=Br, Z=Boc

[20], X=Br, Z=Boc, can be synthesized from [11] as described elsewhere herein.

Synthesis of (S)-1-(2-bromo-6-methoxy-5-(3-methoxypropoxy)pyridin-3-yl)-3-methylbutan-2-amine [27], X=Br

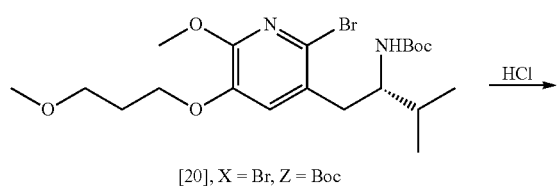

[20], X = Br, Z = Boc

-continued

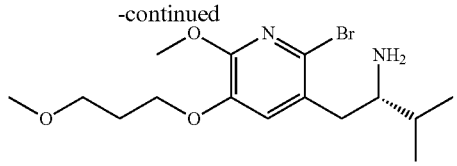

[27], X = Br

To a suspension of [20], X=Br, Z=Boc, in DCM (60 mL), 4N HCl in dioxane (2.0 eq, 6 mL) was added and the suspension was allowed to stir at rt for 24 h. LCMS indicated ~85% product and 15% SM. Another 1.5 mL of 4N HCl were added and the system was allowed to stir for 20 h at room temperature. LCMS indicated 99% product. 25 mL of saturated NaHCO₃ solution was added to make free base [27], X=Br. The DCM layer was separated, washed with water, dried over Na₂SO₄, and evaporated by solvent swapping to n-Heptane (20 mL). The solution was evaporated to dryness to obtain [27], X=Br, as a colorless oil (4.2 g, 97.5% yield). ¹H NMR (400 MHz, chloroform-d) δ 6.99 (s, 1H), 4.07 (td, J=6.5, 1.8 Hz, 2H), 3.97 (s, 3H), 3.70 (s, 2H), 3.54 (t, J=6.0 Hz, 2H), 3.34 (s, 3H), 2.92-2.81 (m, 2H), 2.46-2.33 (m, 1H), 2.08 (p, J=6.3 Hz, 2H), 1.70 (pd, J=6.8, 4.6 Hz, 1H), 1.35-1.15 (m, 4H), 0.99 (dd, J=6.8, 2.5 Hz, 6H).

Synthesis of tert-butyl (S)-1-(1-(2-bromo-6-methoxy-5-(3-methoxypropoxy)pyridin-3-yl)-3-methylbutan-2-yl)-4-oxo-1,4-dihydropyridine-3-carboxylate [29], R=tBu

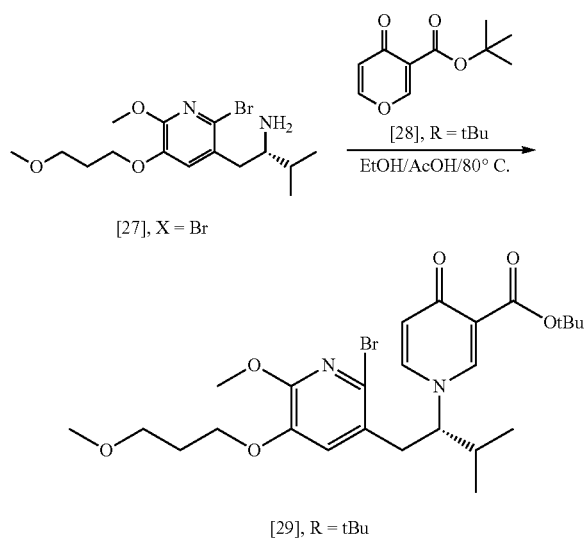

A solution of [27], X=Br, and tert-butyl 4-oxo-4H-pyran-3-carboxylate [28], R=tBu, in EtOH/AcOH 3:1 (v/v, 40 mL) was heated at 80° C. in a 200 mL RBF with a condenser for 3 h and then at room temperature for 18 h. LCMS indicated relatively clean desired product. The solvent was evaporated and then azeotroped once with 20 mL EtOH. MTBE (50 mL) was added and the mixture was washed with NaHCO₃ solution (2×30 mL) and with water (30 mL), and evaporated to give a red-brown residue. The residue was taken up in CPME/n-heptane (100 mL, 3:1 v/v), heated to 70° C. to make a clear solution, slowly cooled to 45° C. (held for 3 h), then slowly cooled to 20° C. and stirred overnight. The solution was then cooled in an ice-bath and filtered. The wet filter cake was washed with CPME/n-heptane (30 mL, 3:1 v/v). The material was dried in an oven at 35° C. with vacuum for 18 h to give product [29], R=tBu, as yellow-orange solid (3.7 g, 60.3% yield). ¹H NMR (400 MHz, chloroform-d) δ 7.82 (d, J=2.3 Hz, 1H), 7.09-7.02 (m, 1H), 6.49 (s, 1H), 6.37 (d, J=7.6 Hz, 1H), 3.95 (s, 3H), 3.93-3.87 (m, 1H), 3.83-3.61 (m, 2H), 3.56-3.38 (m, 3H), 3.30 (s, 3H), 2.69 (dd, J=14.6, 11.5 Hz, 1H), 2.19-2.05 (m, 1H), 1.98 (p, J=6.4, 2H), 1.50 (s, 9H), 1.24 (d, J=6.6 Hz, 3H), 0.89 (t, J=7.0 Hz, 3H).

Synthesis of tert-butyl (S)-6-isopropyl-2-methoxy-3-(3-methoxypropoxy)-10-oxo-5,10-dihydro-6H-pyrido[1,2-h][1,7]naphthyridine-9-carboxylate [25], R=tBu

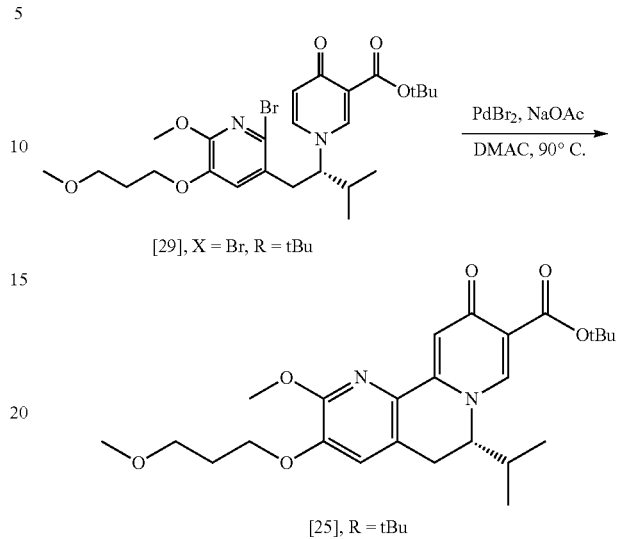

A solution of [29], X=Br, R=tBu (500 mg, 0.93 mmol) in dimethylacetamide (DMAc) was degassed and purged with nitrogen twice. Sodium acetate (152 mg, 1.82 mmol) and palladium bromide (13.0 mg, 0.05 mmol) were added, degassed, and purged with nitrogen. The reaction mixture was heated at 95° C. for 36 h to obtain >95% conversion by LCMS. The reaction mixture was allowed to cool to 20° C., diluted with water (10 mL), and extracted with ethyl acetate (3×10 mL). The ethyl acetate layer was washed with water and evaporated to dryness to give [25], R=tBu, as red colored oily crude residue that was taken to the next step without additional purification. ¹H NMR (400 MHz, chloroform-d) δ 8.05 (s, 1H), 7.41 (s, 1H), 6.87 (s, 1H), 4.17-4.09 (m, 2H), 4.04 (s, 3H), 3.77-3.65 (m, 1H), 3.57 (td, J=6.0, 1.7 Hz, 2H), 3.38-3.31 (m, 5H), 2.15 (p, J=6.4, 2H), 1.57 (m, 10H), 0.95 (m, 3H), 0.83 (d, J=6.7 Hz, 3H).

Synthesis of (S)-6-isopropyl-2-methoxy-3-(3-methoxypropoxy)-10-oxo-5,10-dihydro-6H-pyrido[1,2-h][1,7]naphthyridine-9-carboxylic acid [26]

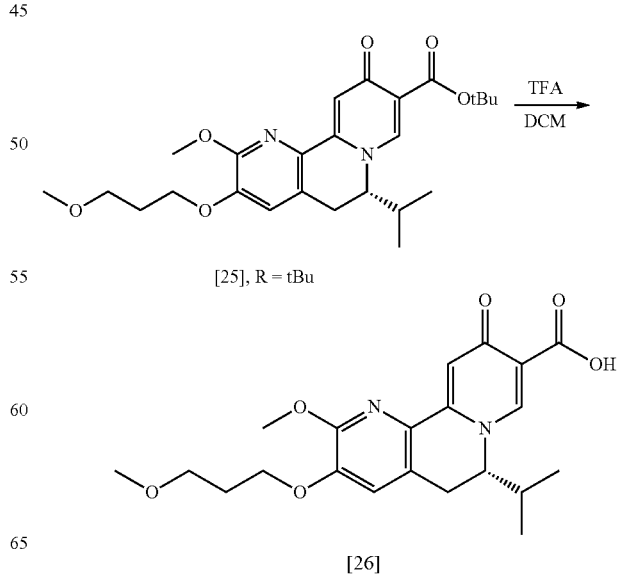

To a solution of [25], R=tBu (650 mg, 1.2 mmol) in methylene chloride (7.0 mL), trifluoracetic acid (2.0 mL) was added and the mixture was stirred at 20° C. for 20 h. LCMS indicated >98% product. The reaction mixture was concentrated and the residue was taken up in ethyl acetate (15 mL). An aqueous NaHCO₃ solution was added until pH 5-6 was reached, and then separated. The ethyl acetate layer was washed with water (5 mL) and evaporated, and the solvent swapped to ethanol (2×2 mL). The product was crystallized from ethanol to give [26] (100 mg, 21%).

Example 6: Synthesis of (S)-6-isopropyl-2-methoxy-3-(3-methoxypropoxy)-10-oxo-5,10-dihydro-6H-pyrido[1,2-h] [1,7]naphthyridine-9-carboxylic acid [26], according to Scheme 3

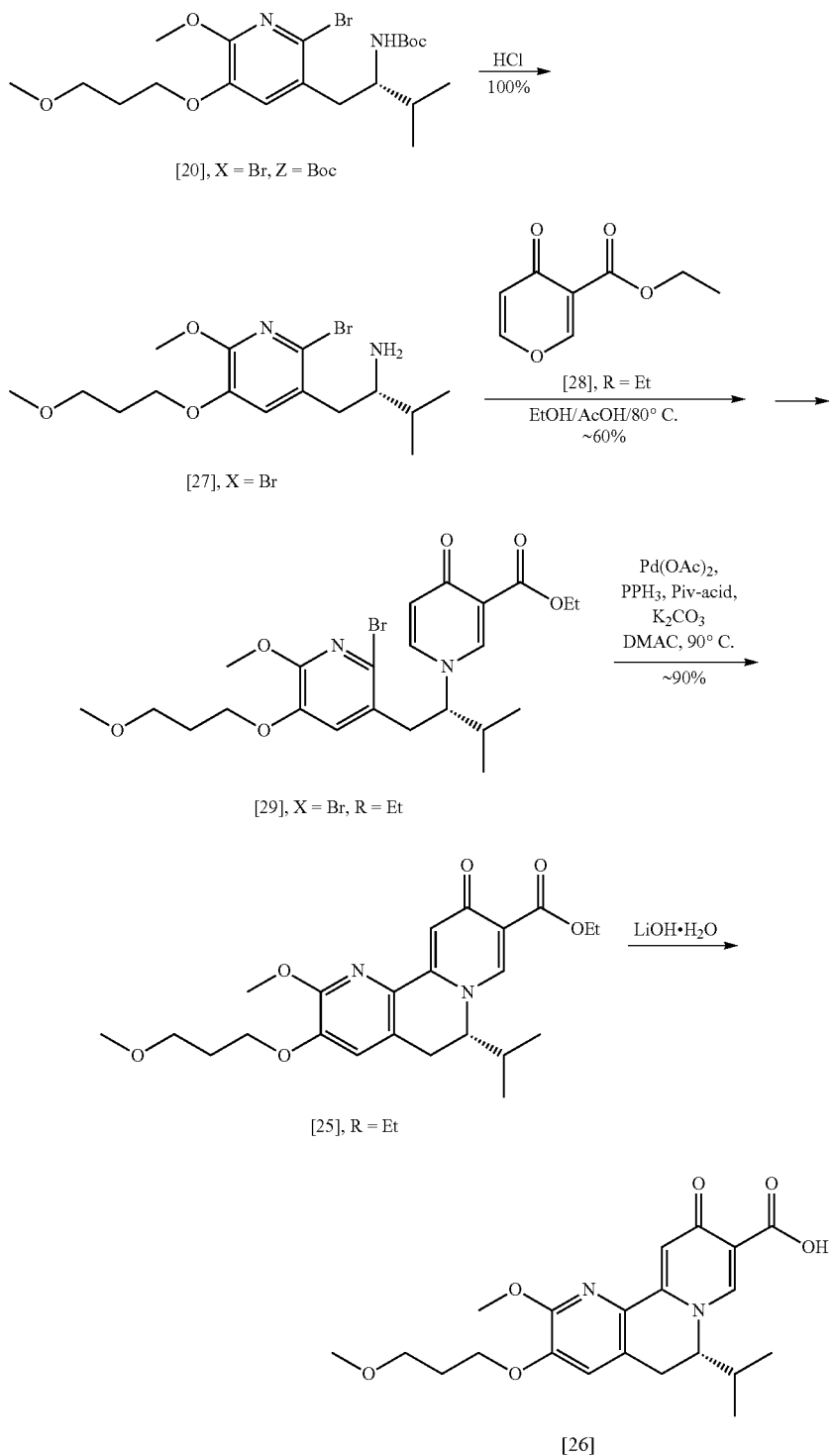

Ethyl (S)-1-(1-(2-bromo-6-methoxy-5-(3-methoxypropoxy)pyridin-3-yl)-3-methylbutan-2-yl)-4-oxo-1,4-dihydropyridine-3-carboxylate [29], X=Br, R=Et A solution of [27], X=Br (16.0 g, 44.3 mmol) and ethyl 4-oxo-4H-pyran-3-carboxylate [28], R=Et (9.01 g, 53.5 mmol) in EtOH/AcOH 7:3 (160 mL) was heated at 80° C. in a 200 mL RBF with condenser for 2 hours and then cooled to room temperature. LCMS indicated clean desired product. The reaction mixture was evaporated and azeotroped twice with 25 mL EtOH. The residue was dissolved in ethyl acetate (120 mL) and the mixture washed with NaHCO$_3$ solution (2×40 mL) and with water (40 mL), and evaporated. Solvent was swapped to MTBE (300 mL), heated to 70° C. to make clear solution and slowly cooled to 45° C. (held for 3 h), then slowly cooled to 20° C. and stirred overnight. The system was cooled in ice-bath and filtered. The filtrate was washed with MTBE and dried in oven at 35° C. with vacuum for 18 h to give product [29], X=Br, R=Et, as light-orange solid (15.0 g, 62.3% yield). $^1$H NMR (400 MHz, CDCl$_3$) δ 7.97 (s, 1H), 7.06 (d, J=7.7 Hz, 1H), 6.50 (s, 1H), 6.40 (d, J=7.7 Hz, 1H), 4.34 (q, J=7.1 Hz, 2H), 3.95 (s, 3H), 3.93-3.87 (m, 1H), 3.83-3.62 (m, 2H), 3.54-3.37 (m, 3H), 3.33 (s, 3H), 2.73 (dd, J=14.7, 11.5 Hz, 1H), 2.14 (m, 1H), 1.97 (m, 2H), 1.36 (t, J=7.1 Hz, 3H), 1.25 (d, J=6.5 Hz, 3H), 0.89 (d, J=6.6 Hz, 3H).

Ethyl (S)-6-isopropyl-2-methoxy-3-(3-methoxypropoxy)-10-oxo-5,10-dihydro-6H-pyrido[1,2-h][1,7]naphthyridine-9-carboxylate [25], R=Et A solution of [29], R=Et (500 mg, 0.93 mmol) in DMAc was degassed and purged with nitrogen twice. Potassium carbonate (149 mg, 1.08 mmol), palladium acetate (5.0 mg, 0.02 mmol), triphenyl phospine (25 mg, 0.1 mmol), and pivalic acid (30 mg, 0.29 mmol) were added, and the system was degassed and purged with nitrogen. The reaction mixture was heated at 65° C. for 40 h to obtain >95% conversion by LCMS. Water (0.5 mL) and N-acetyl cysteine (100 mg) were added and the system was heated at 65° C. for another 2 hours. The reaction mixture was allowed to cool to 20° C., filtered through CELITE®, and washed with toluene. The filtrate was diluted with 10% NaCl solution (50 mL), extracted with toluene 3×8 mL, dried over anhydrous Na$_2$SO$_4$ and evaporated. The residue was triturated with MTBE, filtered and dried to give [25], R=Et, as light-orange solid (0.3 g, 69%).

(S)-6-isopropyl-2-methoxy-3-(3-methoxypropoxy)-10-oxo-5,10-dihydro-6H-pyrido[1,2-h][1,7]naphthyridine-9-carboxylic acid [26]

[25], R=Et, can be hydrolyzed to [26] through sequential treatment with a base (such as but not limited to LiOH) and an acid (which converts the resulting carboxylate salt to carboxylic acid), as described elsewhere herein.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

ENUMERATED EMBODIMENTS

The following enumerated embodiments are provided, the numbering of which is not to be construed as designating levels of importance.

Embodiment 1 provides a method of preparing (S)-6-isopropyl-2-methoxy-3-(3-methoxypropoxy)-10-oxo-5,10-dihydro-6H-pyrido[1,2-h][1,7]naphthyridine-9-carboxylic acid

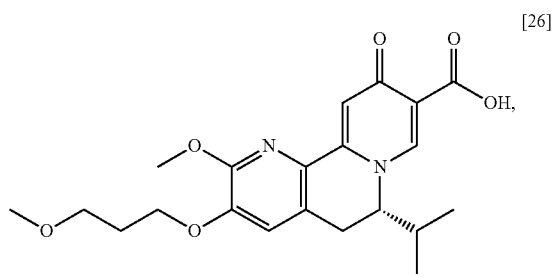 [SMILES: COCCCOc1cc2c(nc1OC)-c1cc(=O)c(C(=O)O)cn1[C@H](C(C)C)C2]

or a salt or solvate thereof, the method comprising hydrolyzing (S)-6-isopropyl-2-methoxy-3-(3-methoxypropoxy)-10-oxo-5,10-dihydro-6H-pyrido[1,2-h][1,7]naphthyridine-9-carboxylic ester

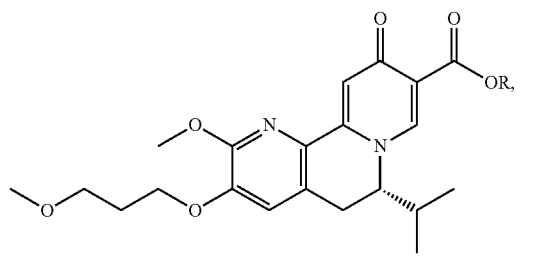

or a salt or solvate thereof, wherein R is C$_1$-C$_6$ alkyl, C$_3$-C$_8$ cycloalkyl, or benzyl.

Embodiment 2 provides the method of Embodiment 1, wherein R is tert-butyl or ethyl.

Embodiment 3 provides the method of any of Embodiments 1-2, wherein [25] is hydrolyzed by contacting [25] with an acid or base.

Embodiment 4 provides the method of Embodiment 3, wherein the acid comprises at least one of hydrochloric acid, sulfuric acid, trifluoroacetic acid, and phosphoric acid, and the base comprises at least one of LiOH, NaOH, and KOH.

Embodiment 5 provides the method of any of Embodiments 3-4, wherein the acid or base is contacted with [25] in a molar ratio of about 1:1 to about 3:1.

Embodiment 6 provides the method of any of Embodiments 1-5, further comprising treating the product of [25] hydrolysis with an acid or base to a pH of about 5 to about 6 so as to isolate free acid [26], and recrystallizing [26] from a solvent comprising at least one alcohol.

Embodiment 7 provides the method of any of Embodiments 1-6, wherein [25] is prepared by a process comprising contacting a dehydrogenation reagent with (6S)-6-isopropyl-2-methoxy-3-(3-methoxypropoxy)-10-oxo-5,10,11,11a-tetrahydro-6H-pyrido[1,2-h][1,7]naphthyridine-9-carboxylic ester

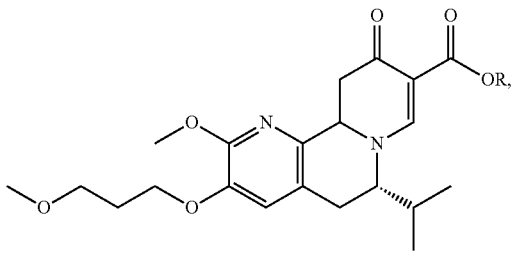

or a salt or solvate thereof, wherein R is $C_1$-$C_6$ alkyl, $C_3$-$C_8$ cycloalkyl, or benzyl.

Embodiment 8 provides the method of Embodiment 7, wherein the dehydrogenation reagent comprises at least one of 2,3-dichloro-5,6-dicyano-1,4-benzoquinone (DDQ), p-chloranil, N-bromosuccinimide, iodine, and manganese dioxide.

Embodiment 9 provides the method of any of Embodiments 7-8, wherein the dehydrogenation reagent is contacted with [24] in a molar ratio of about 1:1 to about 3:1.

Embodiment 10 provides the method of any of Embodiments 7-9, wherein the dehydrogenation reagent is contacted with [24] at a temperature from about 20° C. to about 80° C.

Embodiment 11 provides the method of any of Embodiments 7-10, wherein the reaction mixture is further contacted with an acid about 10 hours to about 30 hours after the dehydrogenation reagent is contacted with [24].

Embodiment 12 provides the method of any of Embodiments 7-11, wherein [24] is prepared by a process comprising contacting (S)-6-isopropyl-2-methoxy-3-(3-methoxypropoxy)-5,6-dihydro-1,7-naphthyridine

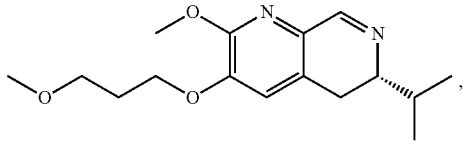

or a salt or solvate thereof, with alkyl 2-(ethoxymethylidene)-3-oxobutanoate

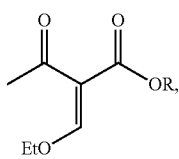

wherein R is $C_1$-$C_6$ alkyl, $C_3$-$C_5$ cycloalkyl, or benzyl.

Embodiment 13 provides the method of Embodiment 12, wherein [22] is contacted with [23] in a molar ratio of about 1:1 to about 1:5.

Embodiment 14 provides the method of any of Embodiments 12-13, wherein [22] is contacted with [23] at a temperature from about 20° C. to about 100° C.

Embodiment 15 provides the method of any of Embodiments 12-14, wherein [22] is prepared by a process comprising at least one of the following steps: contacting a Grignard reagent or alkyl lithium reagent with protected (S)-1-(2-X-6-methoxy-5-(3-methoxypropoxy)pyridin-3-yl)-3-methylbutan-2-amine

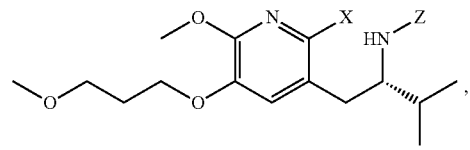

or a salt or solvate thereof, wherein X is selected from the group consisting of Cl, Br, and I, and Z is an amine protecting group, thereby generating an activated intermediate; and contacting the activated intermediate with a carbonyl source.

Embodiment 16 provides the method of Embodiment 15, wherein Z is a protecting group comprising at least one of tert-butyloxycarbonyl (BOC), carbobenzyloxy (Cbz), and optionally substituted benzyl.

Embodiment 17 provides the method of any of Embodiments 15-16, wherein the Grignard reagent or alkyl lithium reagent comprises at least one of MeLi, n-BuLi, i-PrMgCl, i-PrMgCl.LiCl, mixture of i-PrMgCl and n-butyl lithium, MeMgCl, MeMgBr, and cyclohexylmagnesium chloride lithium chloride.

Embodiment 18 provides the method of any of Embodiments 15-17, wherein the carbonyl source comprises at least one of dimethylformamide, formyl-morpholine, and formyl-piperidine.

Embodiment 19 provides the method of any of Embodiments 15-18, wherein the Grignard reagent or alkyl lithium reagent is contacted with [20] in a molar ratio of about 3:2 to about 5:1.

Embodiment 20 provides the method of any of Embodiments 15-19, wherein the activated intermediate is contacted with the carbonyl source in a molar ratio of about 1:1 to about 1:5.

Embodiment 21 provides the method of any of Embodiments 15-20, wherein the Grignard reagent or alkyl lithium reagent is contacted with [20] at a temperature of about −80° C. to about 0° C.

Embodiment 22 provides the method of any of Embodiments 15-21, wherein the activated intermediate is contacted with the carbonyl source at a temperature from about −80° C. to about 0° C.

Embodiment 23 provides the method of any of Embodiments 15-22, wherein contacting the activated intermediate with the carbonyl source forms a secondary intermediate, protected tert-butyl (S)-(1-(2-formyl-6-methoxy-5-(3-methoxypropoxy)pyridin-3-yl)-3-methylbutan-2-yl) amine

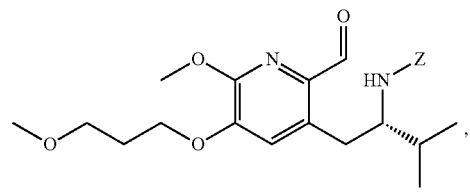

or a salt or solvate thereof, wherein Z is an amine protecting group.

Embodiment 24 provides the method of Embodiment 23, wherein [21] spontaneously converts to [22] upon warming to a temperature higher than about 20° C.

Embodiment 25 provides the method of any of Embodiments 15-24, wherein [25] is prepared by a process comprising contacting a base, a coupling catalyst, and (S)-1-(1-(2-X-6-methoxy-5-(3-methoxypropoxy)pyridin-3-yl)-3-methylbutan-2-yl)-4-oxo-1,4-dihydropyridine-3-carboxylic ester

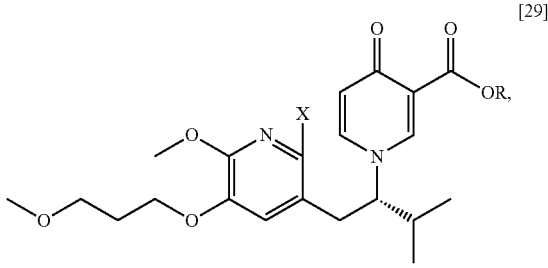

[29]

or a salt or solvate thereof, wherein X is selected from the group consisting of Cl, Br, and I, and R is $C_1$-$C_6$ alkyl, $C_3$-$C_8$ cycloalkyl, or benzyl, thereby generating a reaction mixture.

Embodiment 26 provides the method of Embodiment 25, wherein [29] is contacted with the base and the coupling catalyst in a solution comprising dimethylacetamide.

Embodiment 27 provides the method of any of Embodiments 25-26, wherein the coupling catalyst comprises palladium.

Embodiment 28 provides the method of any of Embodiments 25-27, wherein the coupling catalyst further comprises at least one palladium coordinating ligand.

Embodiment 29 provides the method of any of Embodiments 25-28, wherein the coupling catalyst comprises palladium bromide.

Embodiment 30 provides the method of any of Embodiments 25-29, wherein the coupling catalyst is contacted with [29] in a molar ratio of about 1:10 to about 1:200.

Embodiment 31 provides the method of any of Embodiments 25-30, wherein the base is sodium acetate.

Embodiment 32 provides the method of any of Embodiments 25-31, wherein the base is contacted with [29] in a molar ratio of about 1:1 to about 3:1.

Embodiment 33 provides the method of any of Embodiments 25-32, wherein [29] is contacted with the base and the coupling catalyst at a temperature of about 80° C. to about 100° C.

Embodiment 34 provides the method of any of Embodiments 25-33, wherein [29], the base, and the coupling catalyst are contacted under an inert atmosphere.

Embodiment 35 provides the method of any of Embodiments 25-34, wherein [29] is prepared by a process comprising contacting (S)-1-(2-bromo-6-methoxy-5-(3-methoxypropoxy)pyridin-3-yl)-3-methylbutan-2-amine [27], or a salt or solvate thereof, with 4-oxo-4H-pyran-3-carboxylic ester [28], or a salt or solvate thereof:

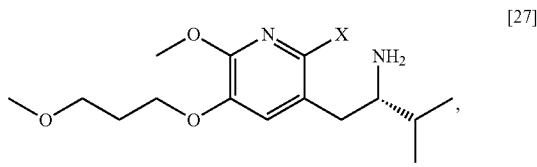

[27]

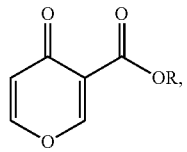

[28]

wherein X is selected from the group consisting of Cl, Br, and I, and R is $C_1$-$C_6$ alkyl, $C_3$-$C_8$ cycloalkyl, or benzyl.

Embodiment 36 provides the method of Embodiment 35, wherein [27] is contacted with [28] in a solvent comprising ethanol and acetic acid in a molar ratio of about 3:1.

Embodiment 37 provides the method of any of Embodiments 35-36, wherein [27] is contacted with [28] at a temperature of about 20° C. to about 100° C.

Embodiment 38 provides the method of any of Embodiments 35-37, wherein [27] is prepared by a process comprising contacting an acid with a protected (S)-1-(2-X-6-methoxy-5-(3-methoxypropoxy)pyridin-3-yl)-3-methylbutan-2-amine

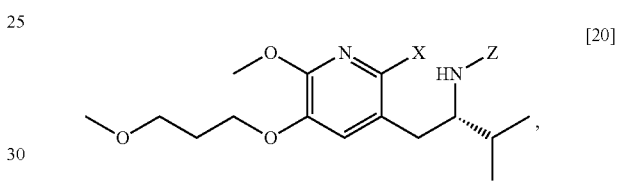

[20]

or a salt or solvate thereof, wherein X is selected from the group consisting of Cl, Br, and I, and Z is an amine protecting group, thereby forming a reaction mixture comprising a salt of [27].

Embodiment 39 provides the method of Embodiment 38, further comprising contacting the reaction mixture with a base so as to generate free base [27].

Embodiment 40 provides the method of any of Embodiments 15-39, wherein [20] is prepared by a process comprising contacting a halogenating agent with protected (S)-1-(6-methoxy-5-(3-methoxypropoxy)pyridin-3-yl)-3-methylbutan-2-amine

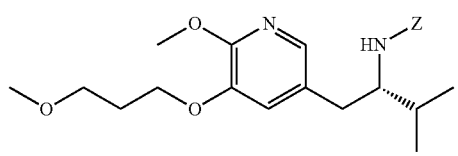

[11], or a salt or solvate thereof, wherein Z is an amine protecting group.

Embodiment 41 provides the method of Embodiment 40, wherein Z is a protecting group comprising at least one of tert-butyloxycarbonyl (BOC), carbobenzyloxy (Cbz), and optionally substituted benzyl.

Embodiment 42 provides the method of any of Embodiments 40-41, wherein the halogenating agent comprises at least one of N-bromosuccinimide (NBS), $Br_2$/AcOH, pyridinium tribromide/DMF, N-iodosuccinimide (NIS), and N-chlorosuccinimide (NCS).

Embodiment 43 provides the method of any of Embodiments 40-42, wherein the halogenating agent is contacted with [11] in a solution comprising at least one of dichloromethane, chloroform, cyclopentyl methyl ether, and dimethylformamide.

Embodiment 44 provides the method of any of Embodiments 40-43, wherein the halogenating agent is contacted with [11] at a temperature of about 20° C. to about 40° C.

Embodiment 45 provides the method of any of Embodiments 40-44, wherein [11] is made by a process comprising at least one of the following steps: contacting 5-X-2-methoxy-3-(3-methoxypropoxy)pyridine

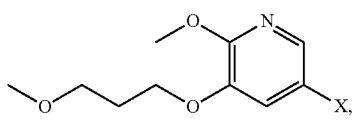

[4]

or a salt or solvate thereof, and a Grignard or alkyl lithium reagent, wherein X is selected from the group consisting of Cl, Br, and I, thereby forming a reactive intermediate; contacting the reactive intermediate, (R)-2-isopropyl-1-tosylaziridine

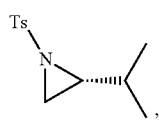

[9]

and a copper salt, thereby forming (S)-N-(1-(6-methoxy-5-(3-methoxypropoxy)pyridin-3-yl)-3-methylbutan-2-yl)-4-methylbenzenesulfonamide

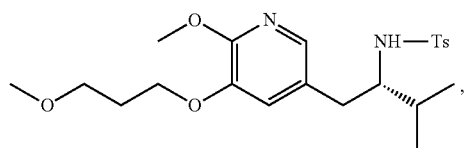

[10]

Z=H; contacting [10], Z=H, and an amine protecting group precursor, thereby forming protected (S)-N-(1-(6-methoxy-5-(3-methoxypropoxy) pyridin-3-yl)-3-methylbutan-2-yl)-4-methylbenzenesulfonamide:

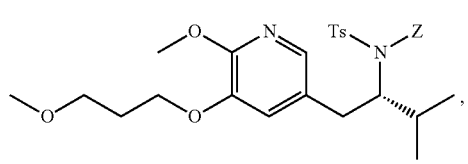

[10]

wherein Z is an amine protecting group; and removing the tosylate (Ts) group from [10] to yield [11].

Embodiment 46 provides the method of Embodiment 45, wherein the Grignard or alkyl lithium reagent comprises at least one of MeLi, t-BuLi, i-PrMgCl, i-PrMgCl.LiCl, mixture of i-PrMgCl and n-butyl lithium, MeMgCl, MeMgBr, and cyclohexylmagnesium chloride lithium chloride.

Embodiment 47 provides the method of any of Embodiments 45-46, wherein the copper salt comprises at least one of CuI, CuBr, CuBr.Me₂S, and CuCN.

Embodiment 48 provides the method of any of Embodiments 45-47, wherein the amine protecting group precursor comprises at least one of tert-butyloxycarbonyl (BOC) anhydride, carbobenzyloxy (Cbz) anhydride, and optionally substituted benzyl chloride.

Embodiment 49 provides the method of any of Embodiments 45-48, wherein Z is a protecting group comprising at least one of tert-butyloxycarbonyl (BOC), carbobenzyloxy (Cbz), and optionally substituted benzyl.

Embodiment 50 provides the method of any of Embodiments 45-49, wherein [4] and the Grignard or alkyl lithium reagent are contacted in a molar ratio of about 1:1.1 to about 1:2. Embodiment 51 provides the method of any of Embodiments 45-50, wherein [4] and the Grignard or alkyl lithium reagent are contacted at a temperature of about 0° C. to about 50° C.

Embodiment 52 provides the method of any of Embodiments 45-51, wherein the reactive intermediate and [9] are contacted in a molar ratio of about 1:0.50 to about 1:1.

Embodiment 53 provides the method of any of Embodiments 45-52, wherein the reactive intermediate and the copper salt are contacted in a molar ratio of about 20:1 to about 10:1.

Embodiment 54 provides the method of any of Embodiments 45-53, wherein the reactive intermediate, [9], and the copper salt are contacted at a temperature of about 20° C. to about 50° C.

Embodiment 55 provides the method of any of Embodiments 45-54, wherein [10], Z=H, is contacted with the amine protecting group precursor in a molar ratio of about 1:1 to about 1:4.

Embodiment 56 provides the method of any of Embodiments 45-55, wherein the tosylate group in [10] is removed by contacting [10] with iodine and magnesium metal.

Embodiment 57 provides the method of any of Embodiments 45-56, wherein [11] is prepared by a process comprising contacting unprotected (S)-1-(6-methoxy-5-(3-methoxypropoxy)pyridin-3-yl)-3-methylbutan-2-amine

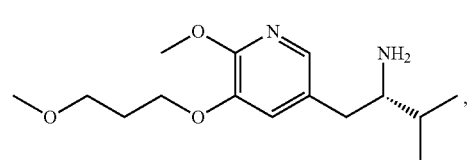

[14]

or a salt or solvate thereof, with an amine protecting group precursor.

Embodiment 58 provides the method of Embodiment 57, wherein the amine protecting group precursor comprises at least one of tert-Butyloxycarbonyl (BOC) anhydride, Carbobenzyloxy (Cbz) anhydride, and optionally substituted benzyl chloride.

Embodiment 59 provides the method of any of Embodiments 57-58, wherein [14] is prepared by a process comprising at least one of the following steps: contacting a first Grignard or alkyl lithium reagent and 5-X-2-methoxy-3-(3-methoxypropoxy)pyridine

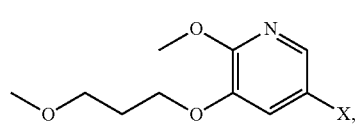

[4]

or a salt or solvate thereof, thereby forming a first reactive intermediate, wherein X is selected from the group consisting of Cl, Br, and I; contacting a second Grignard or alkyl lithium reagent and a protected (R)-2-amino-N-methoxy-N,3-dimethylbutanamide

[12]

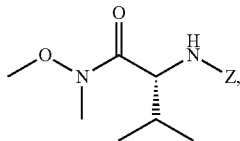

wherein Z is an amine protecting group, thereby forming a second reactive intermediate; contacting the first reactive intermediate and the second reactive intermediate, thereby forming protected N-[(2R)-1-[6-methoxy-5-(3-methoxypropoxy) pyridin-3-yl]-3-methyl-1-oxobutan-2-yl]amine

[13]

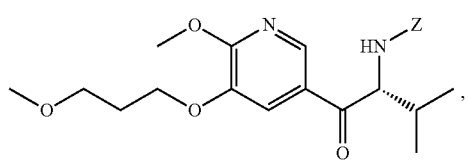

wherein Z is an amine protecting group; and contacting [13] with a reducing reagent to yield [14].

Embodiment 60 provides the method of Embodiment 59, wherein the first Grignard or alkyl lithium reagent and the second Grignard or alkyl lithium reagent independently comprise at least one of MeLi, t-BuLi, i-PrMgCl, i-PrMgCl·LiCl, mixture of i-PrMgCl and n-butyl lithium, MeMgCl, MeMgBr, and cyclohexylmagnesium chloride lithium chloride.

Embodiment 61 provides the method of any of Embodiments 59-60, wherein [4] is contacted with the first Grignard or alkyl lithium reagent in a molar ratio of about 1:1 to about 1:2.

Embodiment 62 provides the method of any of Embodiments 59-61, wherein [12] is contacted with the second Grignard or alkyl lithium reagent in a molar ratio of about 1:1 to about 1:2.

Embodiment 63 provides the method of any of Embodiments 59-62, wherein the reducing reagent comprises at least one of a gallium salt and a silyl hydride, a palladium source, and a platinum source.

Embodiment 64 provides the method of any of Embodiments 59-63, wherein the contacting of [13] with a reducing reagent takes place at a temperature of about 20° C. to about 100° C.

Embodiment 65 provides the method of any of Embodiments 57-58, wherein [14] is prepared by a process comprising at least one of the following steps: (a) contacting 1-(6-methoxy-5-(3-methoxypropoxy)pyridin-3-yl)-3-methylbutan-2-one

[15]

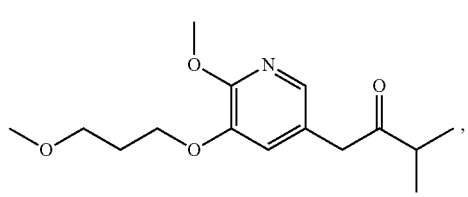

or a salt or solvate thereof, (R)-2-methylpropane-2-sulfinamide

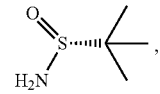

and a Lewis acid under conditions that allow for formation of (R)-N-(1-(6-methoxy-5-(3-methoxypropoxy)pyridin-3-yl)-3-methylbutan-2-ylidene)-2-methylpropane-2-sulfinamide

[18]

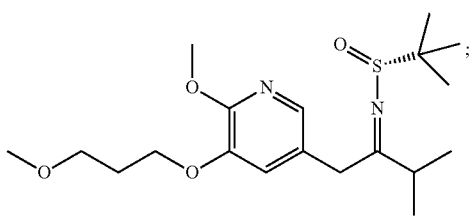

contacting [18] with a reducing agent under conditions that allow for formation of (R)-N-((S)-1-(6-methoxy-5-(3-methoxypropoxy)pyridin-3-yl)-3-methylbutan-2-yl)-2-methylpropane-2-sulfinamide

[19]

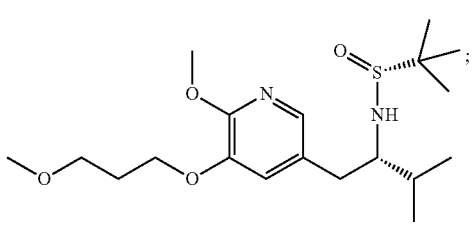

contacting [19] with an acid, thus forming [14], or a salt or solvate thereof; or (b) contacting 1-(6-methoxy-5-(3-methoxypropoxy)pyridin-3-yl)-3-methylbutan-2-one

[15]

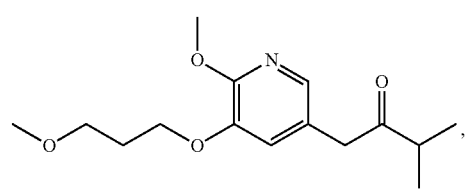

or a salt or solvate thereof, (S)-2-methylpropane-2-sulfinamide

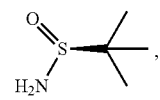

and a Lewis acid under conditions that allow for formation of (S)-N-(1-(6-methoxy-5-(3-methoxypropoxy)pyridin-3-yl)-3-methylbutan-2-ylidene)-2-methylpropane-2-sulfinamide

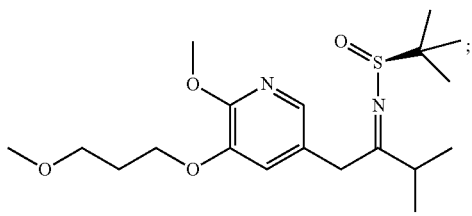

contacting [16] with a reducing agent under conditions that allow for formation of (S)-N-((S)-1-(6-methoxy-5-(3-methoxypropoxy)pyridin-3-yl)-3-methylbutan-2-yl)-2-methylpropane-2-sulfinamide

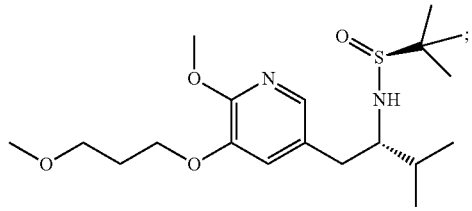

contacting [17] with an acid, thus forming [14], or a salt or solvate thereof.

Embodiment 66 provides the method of Embodiment 65, wherein the reducing reagent comprises diisobutylaluminum hydride (DIBAL-H).

Embodiment 67 provides the method of any of Embodiments 65-66, wherein the acid is a solution comprising HCl.

Embodiment 68 provides the method of any of Embodiments 65-67, wherein [16] or [18] is contacted with the reducing reagent in a molar ratio of about 1:2 to about 1:4.

Embodiment 69 provides the method of any of Embodiments 65-68, wherein [16] or [18] is contacted with the reducing reagent at a temperature below about −20° C.

Embodiment 70 provides the method of any of Embodiments 65-69, wherein [15], or a salt or solvate thereof, is prepared by contacting 5-X-2-methoxy-3-(3-methoxypropoxy)pyridine

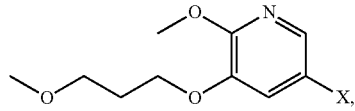

or a salt or solvate thereof, with 3-methylbutan-2-one, and a base, wherein X is selected from the group consisting of Cl, Br, and I.

Embodiment 71 provides the method of Embodiment 70, wherein the base comprises an alkoxide.

Embodiment 72 provides the method of any of Embodiments 70-71, wherein [4], or a salt or solvate thereof, 3-methylbutan-2-one, and the base are further contacted with a coupling catalyst.

Embodiment 73 provides the method of any of Embodiments 70-72, wherein the coupling catalyst comprises a palladium complex and a palladium coordinating ligand.

Embodiment 74 provides the method of any of Embodiments 70-73, wherein the coupling catalyst comprises $Pd_2(dba)_3$ and 4,5-bis(diphenylphosphino)-9,9-dimethylxanthene (Xantphos).

Embodiment 75 provides the method of any of Embodiments 70-74, wherein the molar ratio of the palladium complex about 1:10 to about 1:200 with respect to [4].

Embodiment 76 provides the method of any of Embodiments 70-75, wherein [4], or a salt or solvate thereof, 3-methylbutan-2-one, and the base are contacted at a temperature of about 20° C. to about 40° C.

Embodiment 77 provides the method of any of Embodiments 70-76, wherein [4], or a salt or solvate thereof, 3-methylbutan-2-one, and the base are contacted with the coupling catalyst at a temperature of about 60° C. to about 100° C.

What is claimed is:

1. A method of preparing (S)-6-isopropyl-2-methoxy-3-(3-methoxypropoxy)-10-oxo-5,10-dihydro-6H-pyrido[1,2-h][1,7]naphthyridine-9-carboxylic acid

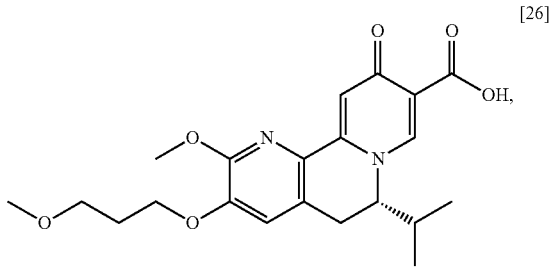 [SMILES: COCCCOc1cc2c(nc1OC)-c1cc(=O)c(C(=O)O)cn1[C@H](C(C)C)C2]

or a salt or solvate thereof, the method comprising hydrolyzing (S)-6-isopropyl-2-methoxy-3-(3-methoxypropoxy)-10-oxo-5,10-dihydro-6H-pyrido[1,2-h][1,7]naphthyridine-9-carboxylic ester

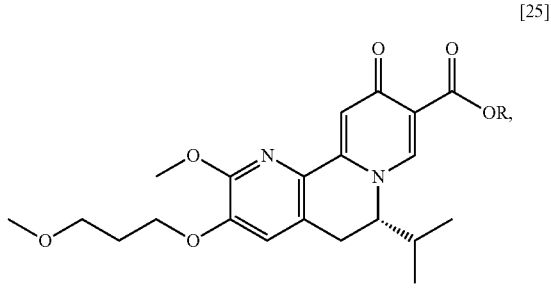

or a salt or solvate thereof, wherein R is $C_1$-$C_6$ alkyl, $C_3$-$C_8$ cycloalkyl, or benzyl.

2. The method of claim 1, wherein R is tert-butyl or ethyl.

3. The method of claim 1, wherein [25] is hydrolyzed by contacting [25] with a first acid or first base,
    optionally the method further comprising treating the product of [25] hydrolysis with a second acid or second base to a pH of about 5 to about 6 so as to isolate free acid [26] and recrystallizing [26] from a solvent comprising at least one alcohol.

4. The method of claim 3, wherein at least one of the following applies:
    (a) the first acid comprises at least one of hydrochloric acid, sulfuric acid, trifluoroacetic acid, and phosphoric acid;
    (b) the first base comprises at least one of LiOH, NaOH, and KOH; and
    (c) the first acid or first base is contacted with [25] in a molar ratio of 1:1 to about 3:1.

5. The method of claim 1, wherein [25] is prepared by a process comprising contacting a dehydrogenation reagent with (6S)-6-isopropyl-2-methoxy-3-(3-methoxypropoxy)-10-oxo-5,10,11,11a-tetrahydro-6H-pyrido[1,2-h][1,7]naphthyridine-9-carboxylic ester

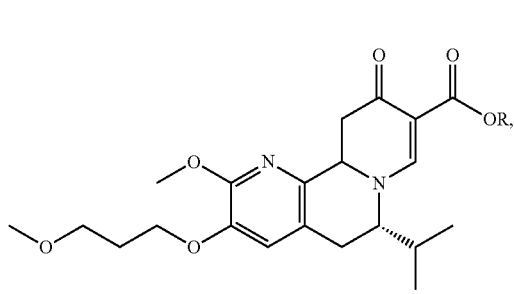

[24]

or a salt or solvate thereof, wherein R is $C_1$-$C_6$ alkyl, $C_3$-$C_8$ cycloalkyl, or benzyl.

6. The method of claim 5, wherein at least one of the following applies:
  (a) the dehydrogenation reagent comprises at least one of 2,3-dichloro-5,6-dicyano-1,4-benzoquinone (DDQ), p-chloranil, N-bromosuccinimide, iodine, and manganese dioxide;
  (b) the dehydrogenation reagent is contacted with [24] in a molar ratio of about 1:1 to about 3:1;
  (c) the dehydrogenation reagent is contacted with [24] at a temperature from about 20° C. to about 80° C.; and
  (d) the reaction mixture is further contacted with an acid about 10 hours to about 30 hours after the dehydrogenation reagent is contacted with [24].

7. The method of claim 5, wherein [24] is prepared by a process comprising contacting (S)-6-isopropyl-2-methoxy-3-(3-methoxypropoxy)-5,6-dihydro-1,7-naphthyridine

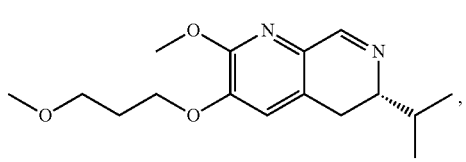

[22]

or a salt or solvate thereof, with alkyl 2-(ethoxymethylidene)-3-oxobutanoate

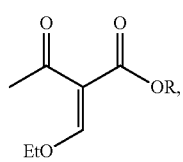

[23]

wherein R is $C_1$-$C_6$ alkyl, $C_3$-$C_8$ cycloalkyl, or benzyl.

8. The method of claim 7, wherein at least one of the following applies:
  (a) [22] is contacted with [23] in a molar ratio of about 1:1 to about 1:5; and
  (b) [22] is contacted with [23] at a temperature from about 20° C. to about 100° C.

9. The method of claim 8, wherein [22] is prepared by a process comprising:
  contacting a Grignard reagent or alkyl lithium reagent with protected (S)-1-(2-X-6-methoxy-5-(3-methoxypropoxy)pyridin-3-yl)-3-methylbutan-2-amine

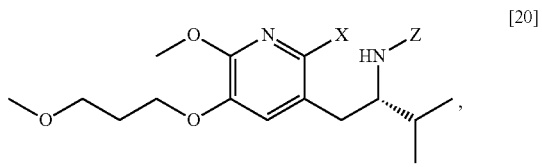

[20]

or a salt or solvate thereof, wherein X is selected from the group consisting of Cl, Br, and I, and Z is an amine protecting group, thereby generating an activated intermediate; and
  contacting the activated intermediate with a carbonyl source.

10. The method of claim 9, wherein at least one of the following applies:
  (a) Z is a protecting group comprising at least one of tert-butyloxycarbonyl (BOC), carbobenzyloxy (Cbz), and optionally substituted benzyl;
  (b) the Grignard reagent or alkyl lithium reagent comprises at least one of MeLi, n-BuLi, i-PrMgCl, i-PrMgCl.LiCl, mixture of i-PrMgCl and n-butyl lithium, MeMgCl, MeMgBr, and cyclohexylmagnesium chloride lithium chloride;
  (c) the carbonyl source comprises at least one of dimethylformamide, formyl-morpholine, and formyl-piperidine;
  (d) the Grignard reagent or alkyl lithium reagent is contacted with [20] in a molar ratio of about 3:2 to about 5:1;
  (e) the activated intermediate is contacted with the carbonyl source in a molar ratio of about 1:1 to about 1:5;
  (f) the Grignard reagent or alkyl lithium reagent is contacted with [20] at a temperature of about −80° C. to about 0° C.; and
  (g) the activated intermediate is contacted with the carbonyl source at a temperature from about −80° C. to about 0° C.

11. The method of claim 9, wherein contacting the activated intermediate with the carbonyl source forms a secondary intermediate, protected tert-butyl (S)-(1-(2-formyl-6-methoxy-5-(3-methoxypropoxy)pyridin-3-yl)-3-methylbutan-2-yl) amine

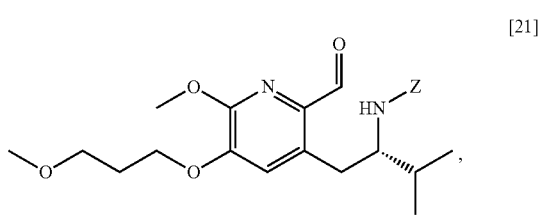

[21]

or a salt or solvate thereof, wherein Z is an amine protecting group.

12. The method of claim 11, wherein [21] spontaneously converts to [22] upon warming to a temperature higher than about 20° C.

13. The method of claim 1, wherein [25] is prepared by a process comprising contacting a base, a coupling catalyst, and (S)-1-(1-(2-X-6-methoxy-5-(3-methoxypropoxy)pyridin-3-yl)-3-methylbutan-2-yl)-4-oxo-1,4-dihydropyridine-3-carboxylic ester

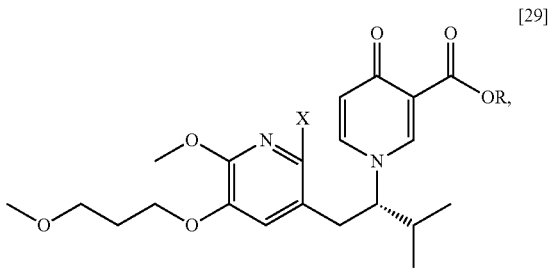

or a salt or solvate thereof, wherein X is selected from the group consisting of Cl, Br, and I, and R is $C_1$-$C_6$ alkyl, $C_3$-$C_8$ cycloalkyl, or benzyl, thereby generating a reaction mixture.

14. The method of claim 13, wherein at least one of the following applies:
    (a) [29] is contacted with the base and the coupling catalyst in a solution comprising dimethylacetamide;
    (b) the coupling catalyst comprises palladium optionally coordinated by at least one ligand or palladium bromide;
    (c) the coupling catalyst is contacted with [29] in a molar ratio of about 1:10 to about 1:200;
    (d) the base is sodium acetate;
    (e) the base is contacted with [29] in a molar ratio of about 1:1 to about 3:1;
    (f) [29] is contacted with the base and the coupling catalyst at a temperature of about 80° C. to about 100° C.; and
    (g) [29], the base, and the coupling catalyst are contacted under an inert atmosphere.

15. The method of claim 13, wherein [29] is prepared by a process comprising contacting (S)-1-(2-bromo-6-methoxy-5-(3-methoxypropoxy)pyridin-3-yl)-3-methylbutan-2-amine [27], or a salt or solvate thereof, with 4-oxo-4H-pyran-3-carboxylic ester [28], or a salt or solvate thereof:

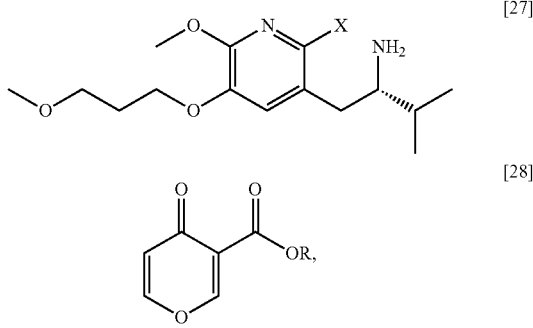

wherein X is selected from the group consisting of Cl, Br, and I, and R is $C_1$-$C_6$ alkyl, $C_3$-$C_8$ cycloalkyl, or benzyl.

16. The method of claim 15, wherein at least one of the following applies:
    (a) [27] is contacted with [28] in a solvent comprising ethanol and acetic acid in a molar ratio of about 3:1; and
    (b) [27] is contacted with [28] at a temperature of about 20° C. to about 100° C.

17. The method of claim 15, wherein [27] is prepared by a process comprising contacting an acid with a protected (S)-1-(2-X-6-methoxy-5-(3-methoxypropoxy)pyridin-3-yl)-3-methylbutan-2-amine

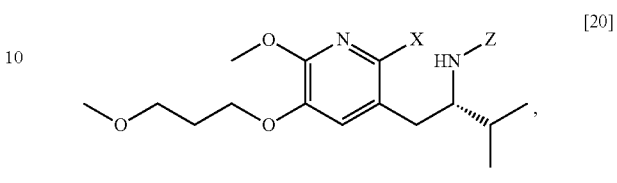

or a salt or solvate thereof, wherein X is selected from the group consisting of Cl, Br, and I, and Z is an amine protecting group, thereby forming a reaction mixture comprising a salt of [27], optionally the method further comprising contacting the reaction mixture with a base as to generate free base [27].

18. The method of claim 9, wherein [20] is prepared by a process comprising contacting a halogenating agent with protected (S)-1-(6-methoxy-5-(3-methoxypropoxy)pyridin-3-yl)-3-methylbutan-2-amine

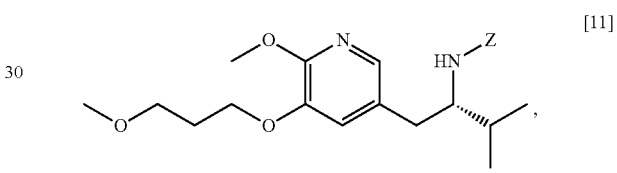

or a salt or solvate thereof, wherein Z is an amine protecting group.

19. The method of claim 18, wherein at least one of the following applies:
    (a) Z is a protecting group comprising at least one of tert-butyloxycarbonyl (BOC), carbobenzyloxy (Cbz), and optionally substituted benzyl;
    (b) the halogenating agent comprises at least one of N-bromosuccinimide (NBS), $Br_2$/AcOH, pyridinium tribromide/DMF, N-iodosuccinimide (NIS), and N-chlorosuccinimide (NCS),
    (c) the halogenating agent is contacted with [11] in a solution comprising at least one of dichloromethane, chloroform, cyclopentyl methyl ether, and dimethylformamide; and
    (d) the halogenating agent is contacted with [11] at a temperature of about 20° C. to about 40° C.

20. The method of claim 18, wherein [11] is made by a process comprising:
    contacting 5-X-2-methoxy-3-(3-methoxypropoxy)pyridine

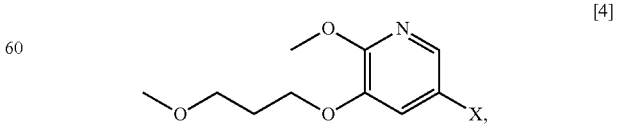

or a salt or solvate thereof, and a Grignard or alkyl lithium reagent, wherein X is selected from the group consisting of Cl, Br, and I, thereby forming a reactive intermediate;

contacting the reactive intermediate, (R)-2-isopropyl-1-tosylaziridine

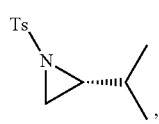

[9]

and a copper salt, thereby forming (S)-N-(1-(6-methoxy-5-(3-methoxypropoxy)pyridin-3-yl)-3-methylbutan-2-yl)-4-methylbenzenesulfonamide

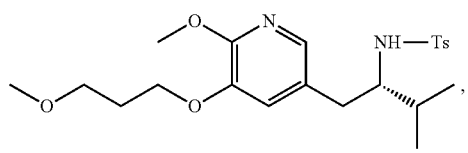

[10]

contacting [10], Z=H, and an amine protecting group precursor, thereby forming protected (S)-N-(1-(6-methoxy-5-(3-methoxypropoxy) pyridin-3-yl)-3-methylbutan-2-yl)-4-methylbenzenesulfonamide:

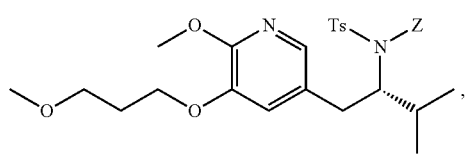

[10]

wherein Z is an amine protecting group; and
removing the tosylate (Ts) group from [10] to yield [11].

21. The method of claim 20, wherein at least one of the following applies:
(a) the Grignard or alkyl lithium reagent comprises at least one of MeLi, t-BuLi, i-PrMgCl, i-PrMgCl.LiCl, mixture of i-PrMgCl and n-butyl lithium, MeMgCl, MeMgBr, and cyclohexylmagnesium chloride lithium chloride;
(b) the copper salt comprises at least one of CuI, CuBr, CuBr.Me₂S, and CuCN;
(c) the amine protecting group precursor comprises at least one of tert-butyloxycarbonyl (BOC) anhydride, carbobenzyloxy (Cbz) anhydride, and optionally substituted benzyl chloride;
(d) Z is a protecting group comprising at least one of tert-butyloxycarbonyl (BOC), carbobenzyloxy (Cbz), and optionally substituted benzyl;
(e) [4] and the Grignard or alkyl lithium reagent are contacted in a molar ratio of about 1:1.1 to about 1:2;
(f) [4] and the Grignard or alkyl lithium reagent are contacted at a temperature of about 0° C. to about 50° C.;
(g) the reactive intermediate and [9] are contacted in a molar ratio of about 1:0.50 to about 1:1;
(h) the reactive intermediate and the copper salt are contacted in a molar ratio of about 20:1 to about 10:1;
(i) the reactive intermediate, [9], and the copper salt are contacted at a temperature of about 20° C. to about 50° C.;
(j) [10], wherein Z=H, is contacted with the amine protecting group precursor in a molar ratio of about 1:1 to about 1:4; and
(k) the tosylate group in [10] is removed by contacting [10] with iodine and magnesium metal.

22. The method of claim 18, wherein [11] is prepared by a process comprising contacting unprotected (S)-1-(6-methoxy-5-(3-methoxypropoxy)pyridin-3-yl)-3-methylbutan-2-amine

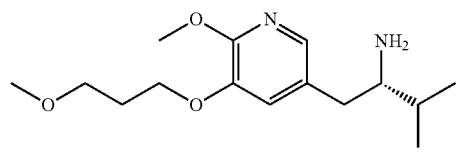

[14]

or a salt or solvate thereof, with an amine protecting group precursor.

23. The method of claim 22, wherein the amine protecting group precursor comprises at least one of tert-Butyloxycarbonyl (BOC) anhydride, Carbobenzyloxy (Cbz) anhydride, and optionally substituted benzyl chloride.

24. The method of claim 22, wherein [14] is prepared by a process comprising:
contacting a first Grignard or alkyl lithium reagent and 5-X-2-methoxy-3-(3-methoxypropoxy)pyridine

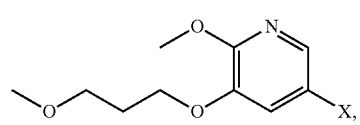

[4]

or a salt or solvate thereof, thereby forming a first reactive intermediate, wherein X is selected from the group consisting of Cl, Br, and I;
contacting a second Grignard or alkyl lithium reagent and a protected (R)-2-amino-N-methoxy-N,3-dimethylbutanamide

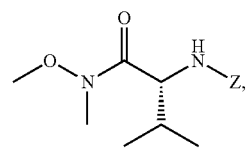

[12]

wherein Z is an amine protecting group, thereby forming a second reactive intermediate;
contacting the first reactive intermediate and the second reactive intermediate, thereby forming protected N-[(2R)-1-[6-methoxy-5-(3-methoxypropoxy) pyridin-3-yl]-3-methyl-1-oxobutan-2-yl]amine

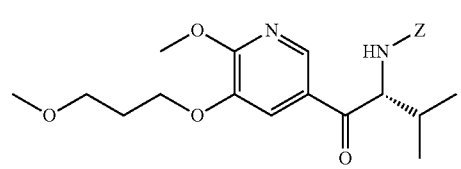

[13]

wherein Z is an amine protecting group; and
contacting [13] with a reducing reagent to yield [14].

25. The method of claim 24, wherein at least one of the following applies:
(a) the first Grignard or alkyl lithium reagent and the second Grignard or alkyl lithium reagent independently comprise at least one of MeLi, t-BuLi, i-PrMgCl, i-PrMgCl.LiCl, mixture of i-PrMgCl and n-butyl lithium, MeMgCl, MeMgBr, and cyclohexylmagnesium chloride lithium chloride;
(b) [4] is contacted with the first Grignard or alkyl lithium reagent in a molar ratio of about 1:1 to about 1:2;
(c) [12] is contacted with the second Grignard or alkyl lithium reagent in a molar ratio of about 1:1 to about 1:2;
(d) the reducing reagent comprises at least one of a gallium salt and a silyl hydride, a palladium source, and a platinum source; and
(e) the contacting of [13] with a reducing reagent takes place at a temperature of about 20° C. to about 100° C.

26. The method of claim 22, wherein [14] is prepared by a process comprising:
(a) contacting 1-(6-methoxy-5-(3-methoxypropoxy)pyridin-3-yl)-3-methylbutan-2-one

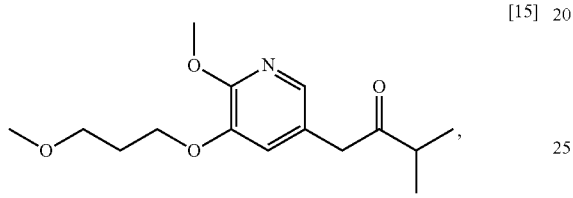

[15]

or a salt or solvate thereof, (R)-2-methylpropane-2-sulfinamide

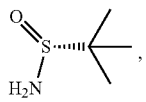

and a Lewis acid under conditions that allow for formation of (R)-N-(1-(6-methoxy-5-(3-methoxypropoxy)pyridin-3-yl)-3-methylbutan-2-ylidene)-2-methylpropane-2-sulfinamide

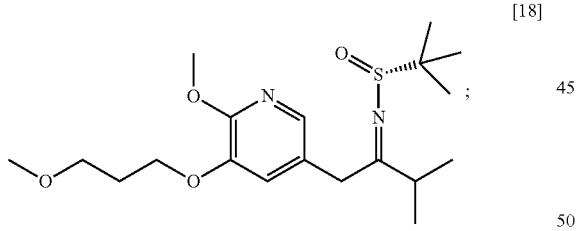

[18]

contacting [18] with a reducing agent under conditions that allow for formation of (R)-N-((S)-1-(6-methoxy-5-(3-methoxypropoxy)pyridin-3-yl)-3-methylbutan-2-yl)-2-methylpropane-2-sulfinamide

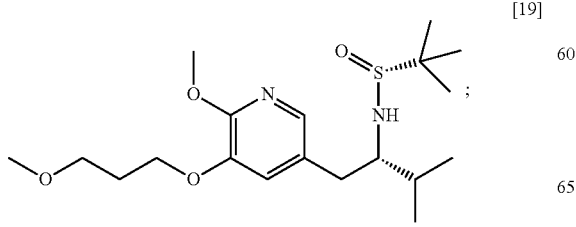

[19]

contacting [19] with an acid, thus forming [14], or a salt or solvate thereof; or
(b) contacting 1-(6-methoxy-5-(3-methoxypropoxy)pyridin-3-yl)-3-methylbutan-2-one

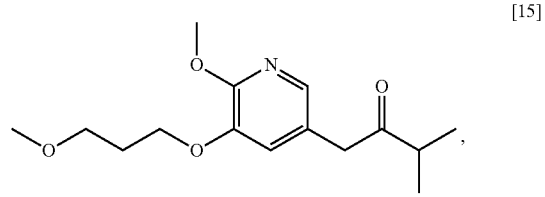 [SMILES: COCCCOc1cc(CC(=O)C(C)C)cnc1OC]

[15]

or a salt or solvate thereof, (S)-2-methylpropane-2-sulfinamide

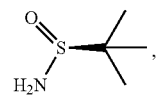

and a Lewis acid under conditions that allow for formation of (S)-N-(1-(6-methoxy-5-(3-methoxypropoxy)pyridin-3-yl)-3-methylbutan-2-ylidene)-2-methylpropane-2-sulfinamide

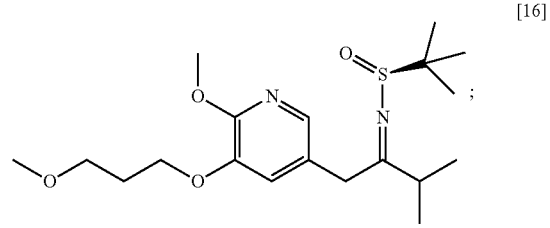 [SMILES: COCCCOc1cc(CC(=N[S@@](=O)C(C)(C)C)C(C)C)cnc1OC]

[16]

contacting [16] with a reducing agent under conditions that allow for formation of (S)-N-((S)-1-(6-methoxy-5-(3-methoxypropoxy)pyridin-3-yl)-3-methylbutan-2-yl)-2-methylpropane-2-sulfinamide

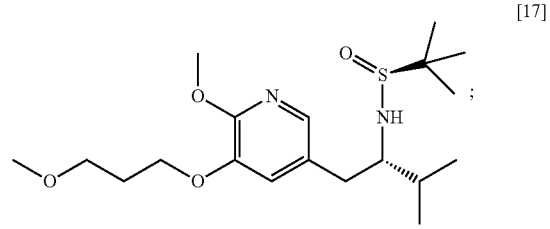 [SMILES: COCCCOc1cc(C[C@H](N[S@@](=O)C(C)(C)C)C(C)C)cnc1OC]

[17]

contacting [17] with an acid, thus forming [14], or a salt or solvate thereof.

27. The method of claim 26, wherein at least one of the following applies:
(a) the reducing reagent comprises diisobutylaluminum hydride (DIBAL-H);
(b) the acid is a solution comprising HCl;
(c) [16] or [18] is contacted with the reducing reagent in a molar ratio of about 1:2 to about 1:4; and
(d) [16] or [18] is contacted with the reducing reagent at a temperature below about −20° C.

28. The method of claim 26, wherein [15], or a salt or solvate thereof, is prepared by contacting 5-X-2-methoxy-3-(3-methoxypropoxy)pyridine

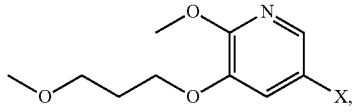

[4]

or a salt or solvate thereof, with 3-methylbutan-2-one, and a base, wherein X is selected from the group consisting of Cl, Br, and I.

29. The method of claim 28, wherein at least one of:
 (a) the base comprises an alkoxide; and
 (b) [4], or a salt or solvate thereof, 3-methylbutan-2-one, and the base are contacted at a temperature of about 20° C. to about 40° C.

30. The method of claim 28, wherein [4], or a salt or solvate thereof, 3-methylbutan-2-one, and the base are further contacted with a coupling catalyst.

31. The method of claim 30, wherein at least one of the following applies:
 (a) the coupling catalyst comprises a palladium complex and a palladium coordinating ligand;
 (b) the coupling catalyst comprises $Pd_2(dba)_3$ and 4,5-bis(diphenylphosphino)-9,9-dimethylxanthene (Xantphos);
 (c) the molar ratio of the palladium complex about 1:10 to about 1:200 with respect to [4]; and
 (d) [4], or a salt or solvate thereof, 3-methylbutan-2-one, and the base are contacted with the coupling catalyst at a temperature of about 60° C. to about 100° C.

* * * * *